United States Patent
United States Patent
Huntington et al.

(10) Patent No.: US 11,904,053 B2
(45) Date of Patent: *Feb. 20, 2024

(54) DRY POWDER FORMULATIONS OF THYMIC STROMAL LYMPHOPOIETIN (TSLP)-BINDING ANTIBODIES AND METHODS OF USE THEREOF

(71) Applicant: MedImmune Limited, Cambridge (GB)

(72) Inventors: Catherine Eugenie Chaillan Huntington, Cambridge (GB); Susan Hoe, San Francisco, CA (US); Prakash Manikwar, Gaithersburg, MD (US); Roland Wilhelm Kolbeck, Gaithersburg, MD (US); Emma Suzanne Cohen, Cambridge (GB); David Lechuga-Ballesteros, San Francisco, CA (US); Kellisa Beth Hansen, San Francisco, CA (US); Dexter Joseph D'Sa, San Francisco, CA (US); Saba Ghazvini, Gaithersburg, MD (US)

(73) Assignee: MEDIMMUNE LIMITED, Cambridge (GB)

( * ) Notice: Subject to any disclaimer, the term of this patent is extended or adjusted under 35 U.S.C. 154(b) by 398 days.

This patent is subject to a terminal disclaimer.

(21) Appl. No.: 17/081,821

(22) Filed: Oct. 27, 2020

(65) Prior Publication Data

US 2021/0121406 A1    Apr. 29, 2021

Related U.S. Application Data

(60) Provisional application No. 62/926,833, filed on Oct. 28, 2019.

(51) Int. Cl.
| | |
|---|---|
| *A61K 9/16* | (2006.01) |
| *A61K 39/00* | (2006.01) |
| *A61K 47/26* | (2006.01) |
| *A61K 9/00* | (2006.01) |
| *C07K 16/24* | (2006.01) |
| *C07K 14/54* | (2006.01) |

(52) U.S. Cl.
CPC ......... *A61K 9/1623* (2013.01); *A61K 9/0075* (2013.01); *A61K 9/1652* (2013.01); *C07K 16/244* (2013.01); *C07K 2317/24* (2013.01); *C07K 2317/55* (2013.01); *C07K 2317/565* (2013.01)

(58) Field of Classification Search
None
See application file for complete search history.

(56) References Cited

U.S. PATENT DOCUMENTS

2017/0066823 A1*  3/2017  Edwards ............... A61K 45/06
2018/0327489 A1  11/2018  Edwards et al.

FOREIGN PATENT DOCUMENTS

| WO | 2001/32144 A1 | 5/2001 |
| WO | 2009/035577 A1 | 3/2009 |
| WO | 2016/142426 A1 | 9/2016 |
| WO | 2017/042696 A1 | 3/2017 |
| WO | WO-2019145897 A1 | 8/2019 |

OTHER PUBLICATIONS

MacCallum et al. (J. Mol. Biol. 1996, 262, 732-745) (Year: 1996).*
Ourdoubadi et al (Int. J. Pharmaceutics, 2021, available online Nov. 2020, doi.org/10.1016/j-ijpharm.2020.120102: 1-14) (Year: 2021).*
Azarmi et al (Int. J. Pharmaceutics, 2006, 319: 155-161) (Year: 2006).*
Darling RJ, et al, Kinetic exclusion assay technology: characterization of molecular interactions, Assay Drug Development Technology, Dec. 2, 2004(6): 647-657.
Gauvreau GM, et al, Effects of an anti-TSLP antibody on allergen-induced asthmatic responses, New England Journal of Medicine, May 29, 2014, 370(22), 2102-10.
Tepper JS, et al, Symposium Summary: Breathe In, Breathe Out, Its Easy: What You Need to Know About Developing Inhaled Drugs, International Journal of Toxicology, Jul. 2016, 35(4), 376-92.
Rennard, SI, et al, Estimation of volume of epithelial lining fluid recovered by lavage using urea as marker of dilution, Journal of Applied Physiology, vol. 60, No. 2, Feb. 1, 1986, 532-538.
Pocket Guide for Asthma Management and Prevention, Global Initiative for Asthma, 2019, 1-38.
Corren J, et al, Tezepelumab in Adults with Uncontrolled Asthma, New England Journal of Medicine, Sep. 7, 2017, 377(10), 936-946.

* cited by examiner

*Primary Examiner* — G. R. Ewoldt
*Assistant Examiner* — Marianne DiBrino
(74) *Attorney, Agent, or Firm* — MARSHALL, GERSTEIN & BORUN LLP

(57) ABSTRACT

The present technology relates generally to dry powder formulations of antibodies specific for thymic stromal lymphopoietin (TSLP), as well as methods of treating asthma, using the dry powder formulations, suitably via pulmonary delivery.

19 Claims, 25 Drawing Sheets

Specification includes a Sequence Listing.

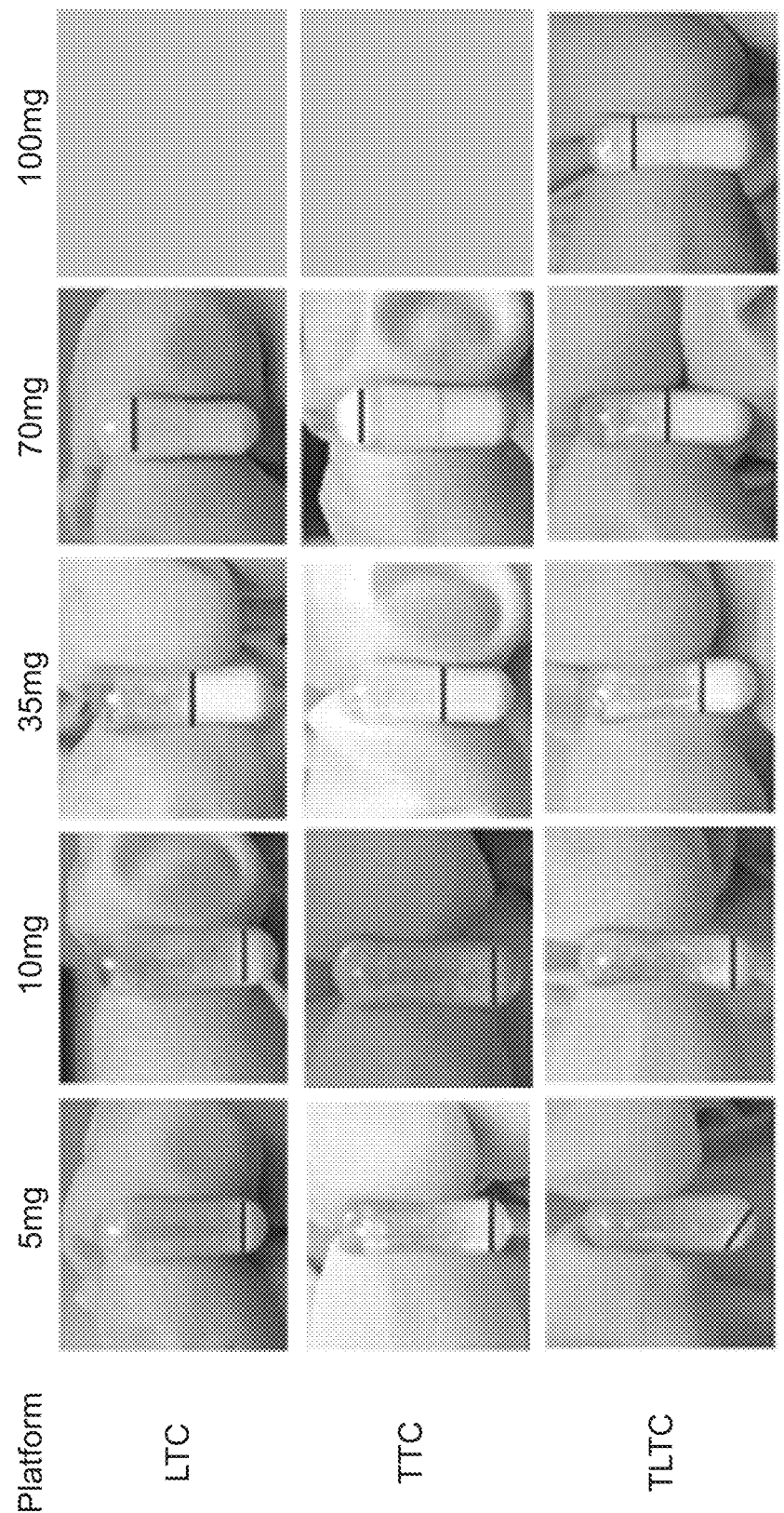

FIG. 11A
| Leu³ | Leu | L:L³ | Treh | cBD | S SA |
|---|---|---|---|---|---|
| 5.7 | 0.6 | 0.3 | 85.2 | 0.54 | 6.03 |
20kV X10,000 1μm 312-039-17
FIG. 11B
| Leu³ | Leu | L:L³ | Treh | cBD | S SA |
|---|---|---|---|---|---|
| 5.7 | 19.9 | 9.5 | 65.8 | 0.50 | 6.59 |
20kV X10,000 1μm 312-039-10
FIG. 11C
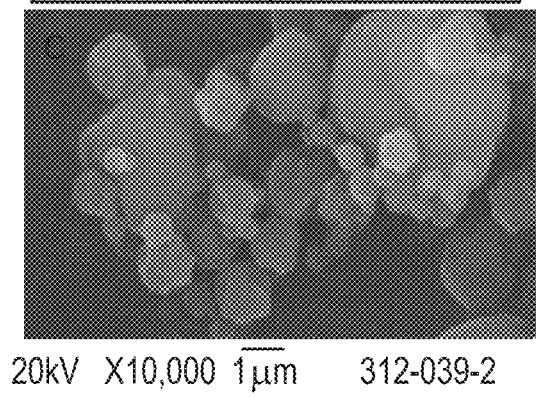
| Leu³ | Leu | L:L³ | Treh | cBD | S SA |
|---|---|---|---|---|---|
| 0.7 | 0.6 | 2.38 | 90.2 | 0.82 | 3.03 |
20kV X10,000 1μm 312-039-2
FIG. 11D
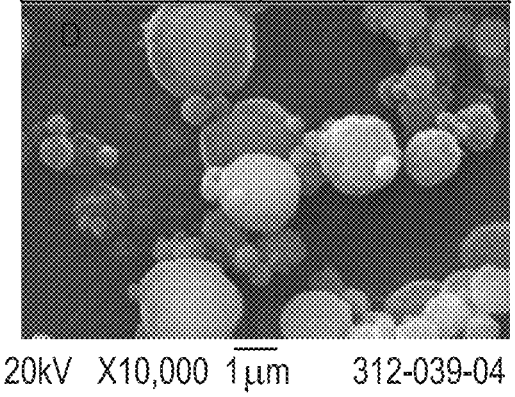
| Leu³ | Leu | L:L³ | Treh | cBD | S SA |
|---|---|---|---|---|---|
| 0.7 | 19.9 | 76.0 | 70.8 | 0.77 | 3.44 |
20kV X10,000 1μm 312-039-04

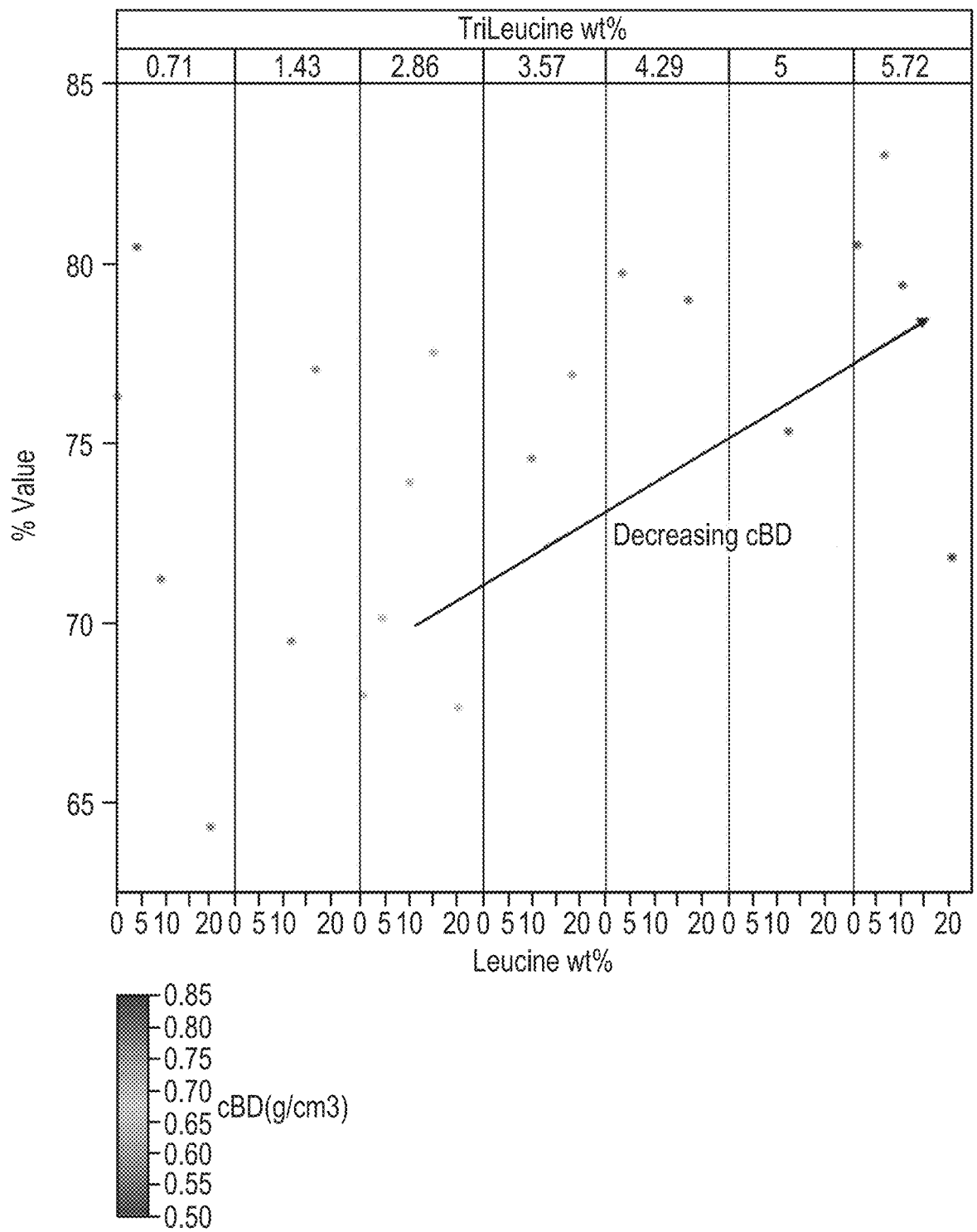

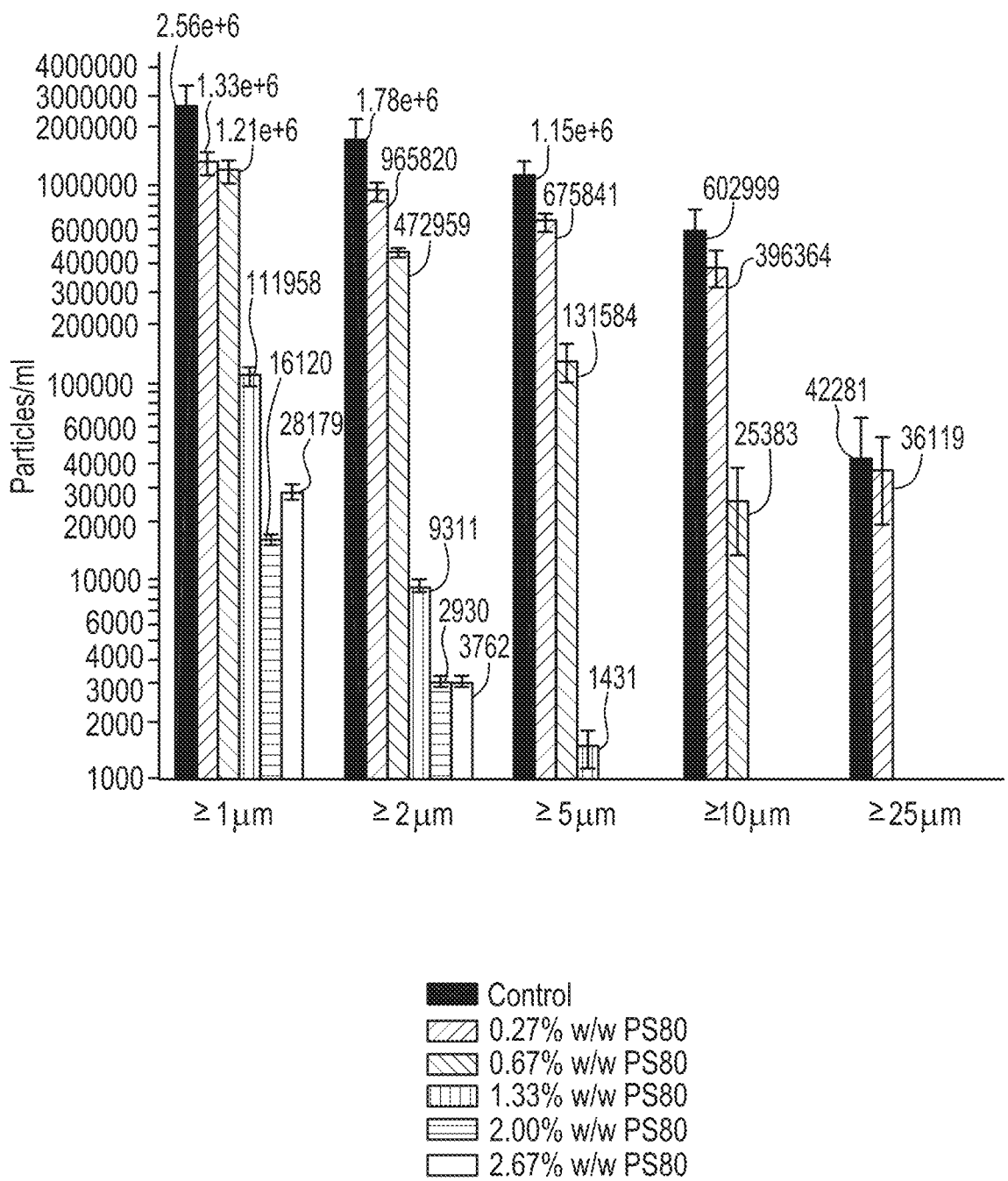

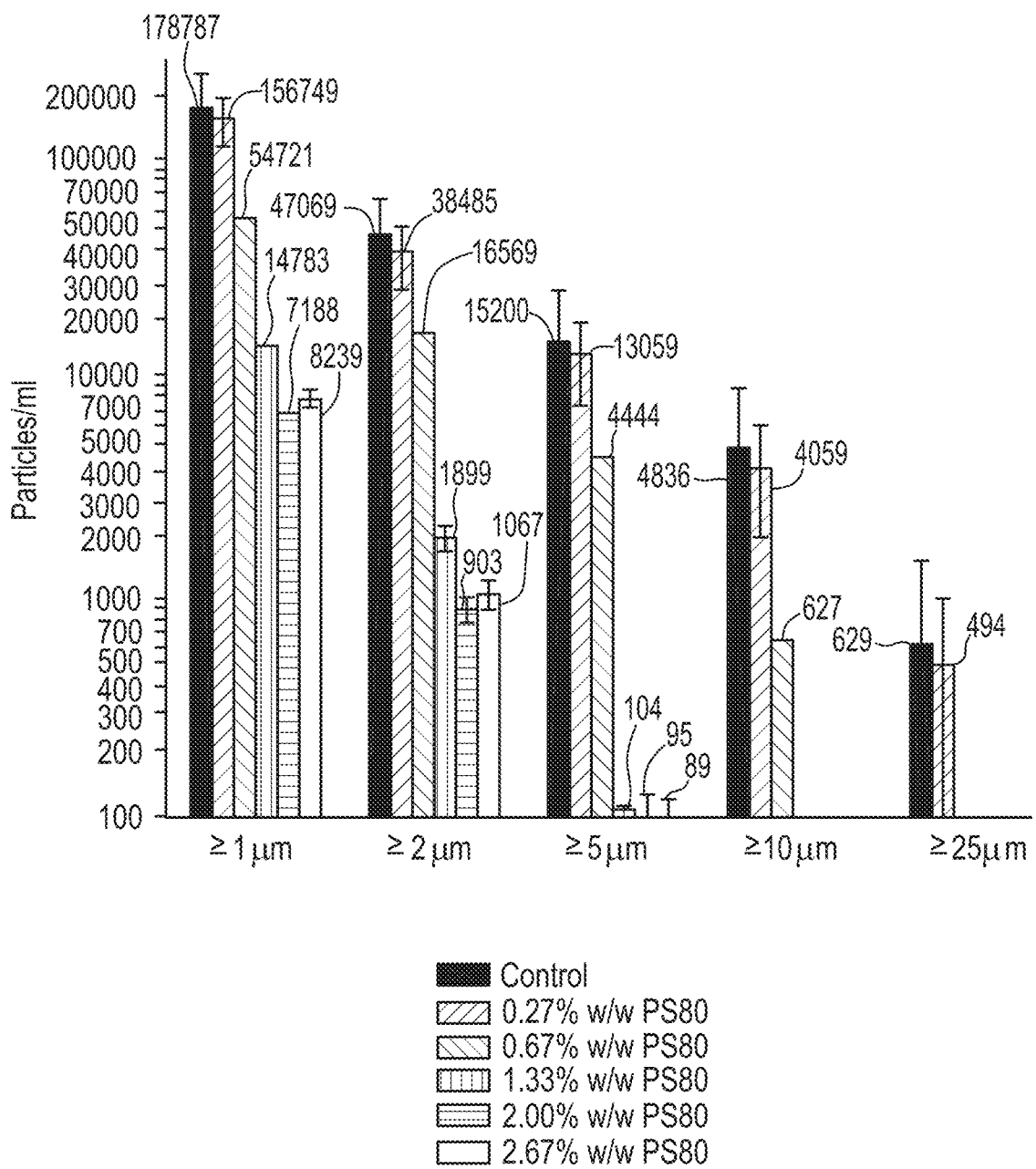

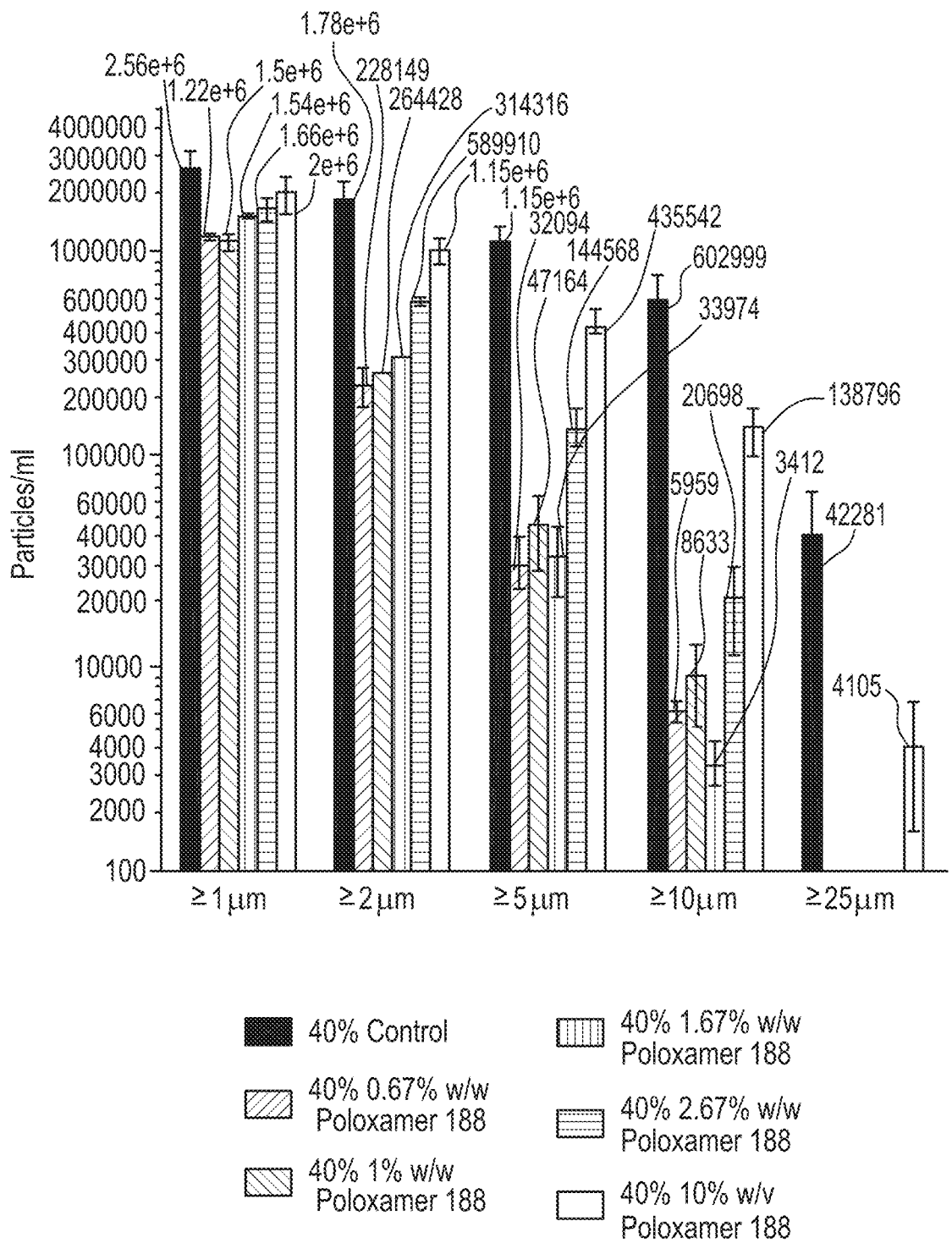

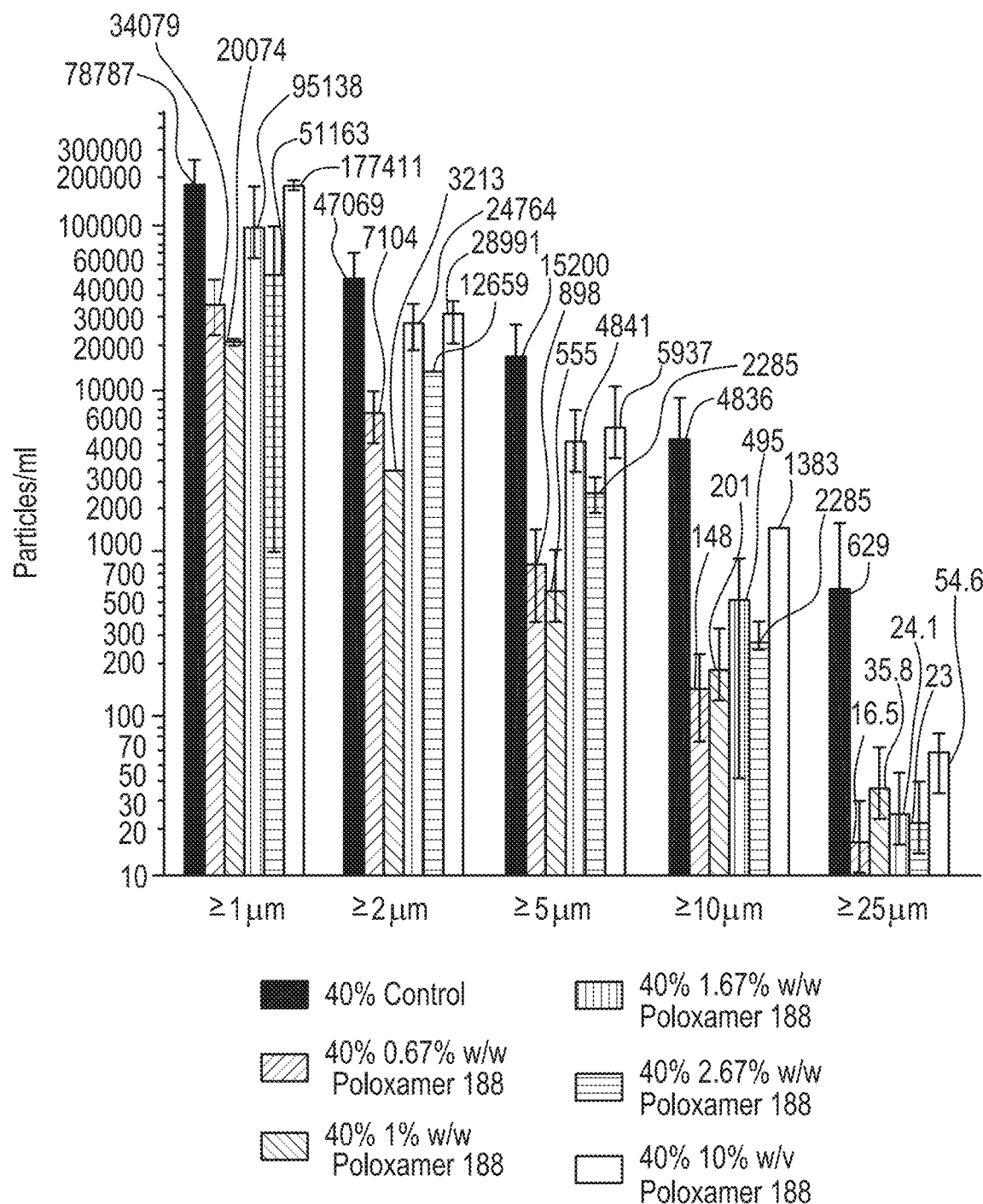

FIG. 17C
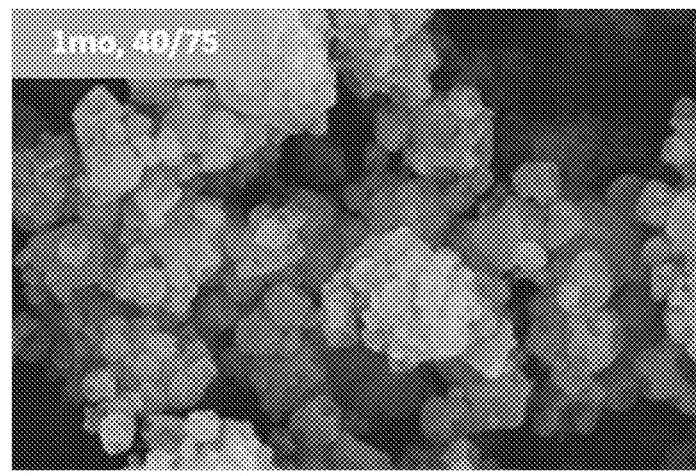
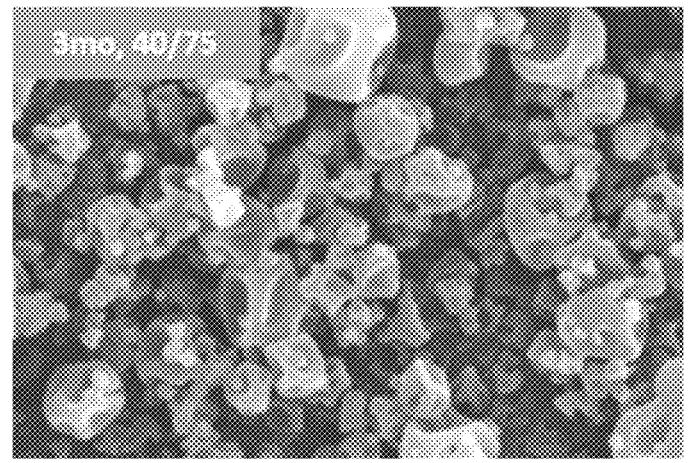
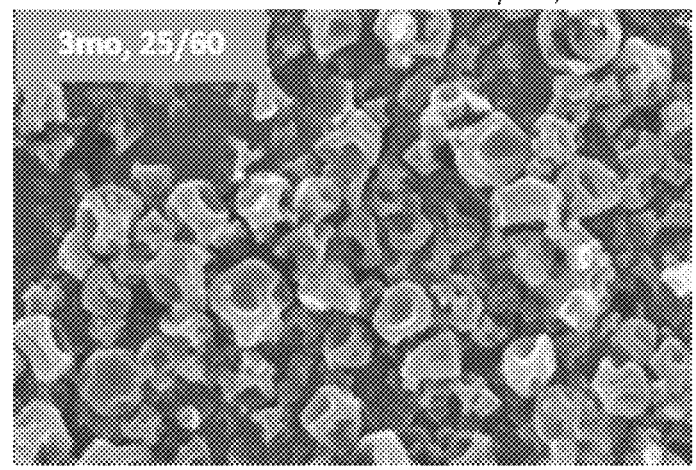

FIG. 18C
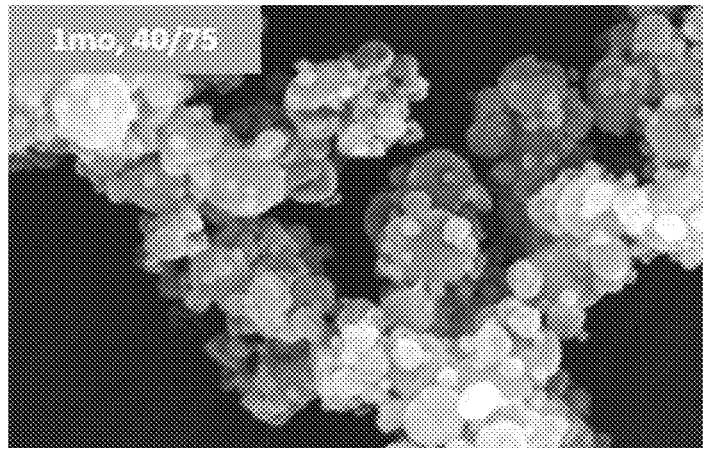
SED 20.0kV WD11mm P.C.50  X5,000  5μm
19-ZS-112 BP 1mo 40,75 R2 5000x    Mar 02, 2020
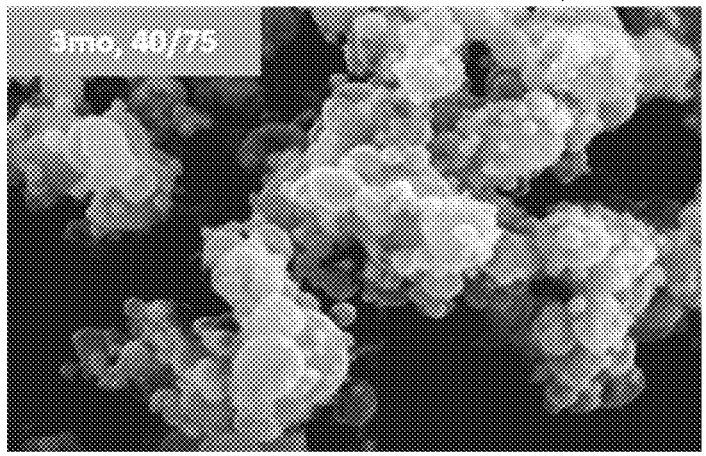
SED 20.0kV WD11mm P.C.50  X5,000  5μm
19-ZS-112BP 40C75RH 3M R2 5000x    May 06, 2020
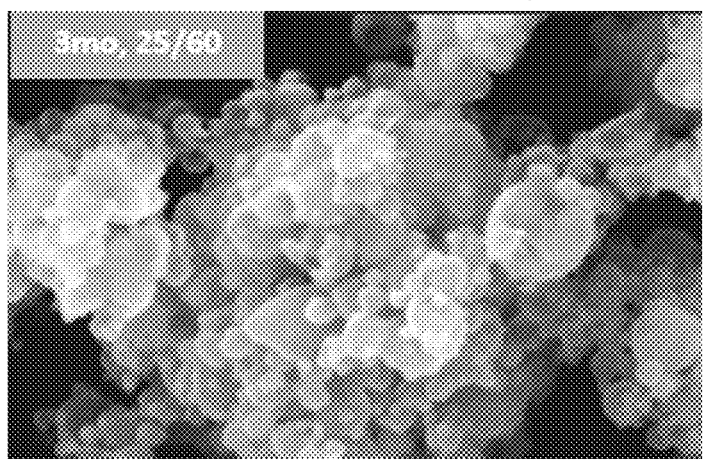
SED 20.0kV WD11mm P.C.50  X5,000  5μm
19-ZS-112BP 25C60RH 3M R1 5000x    May 06, 2020

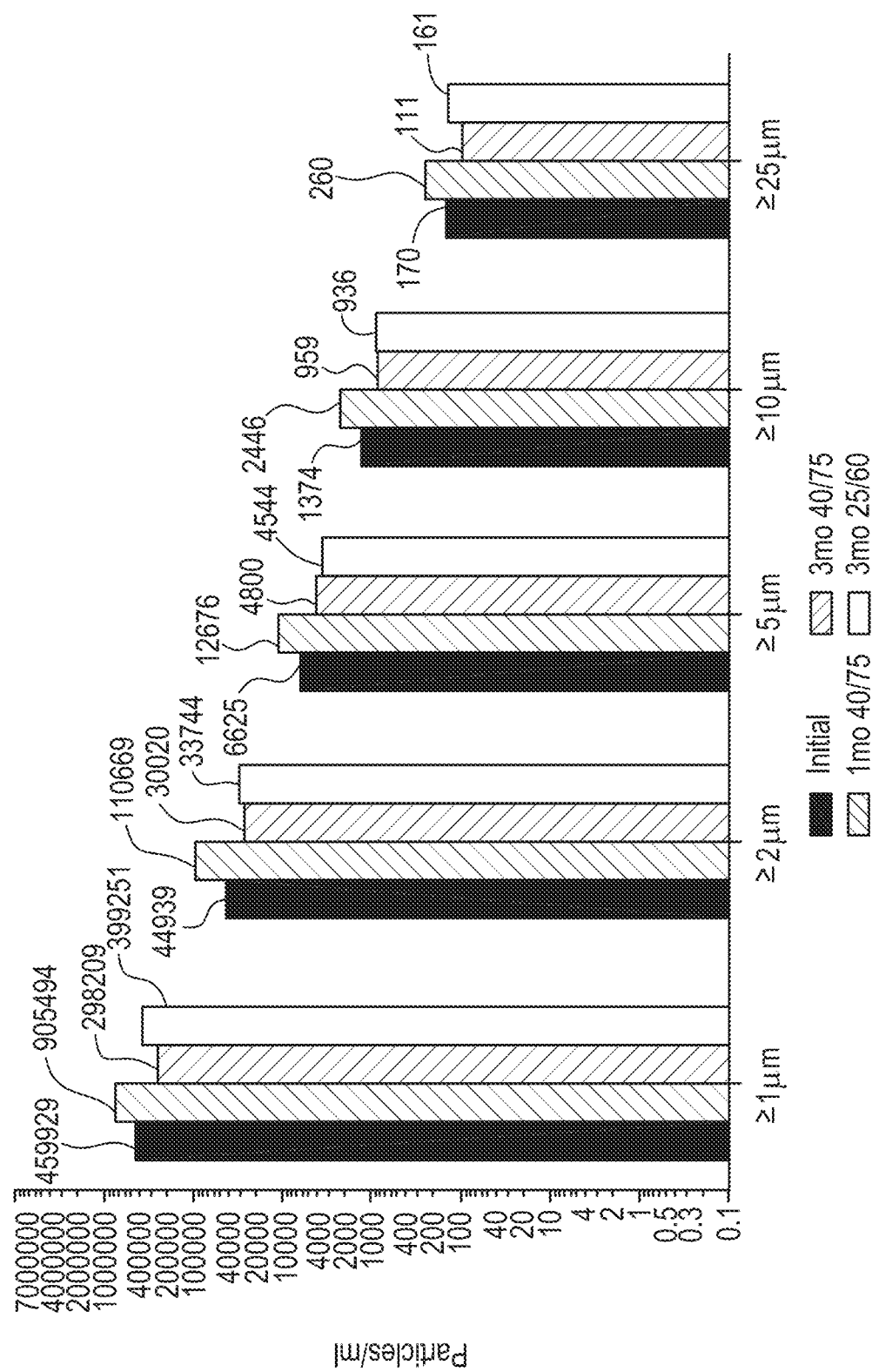

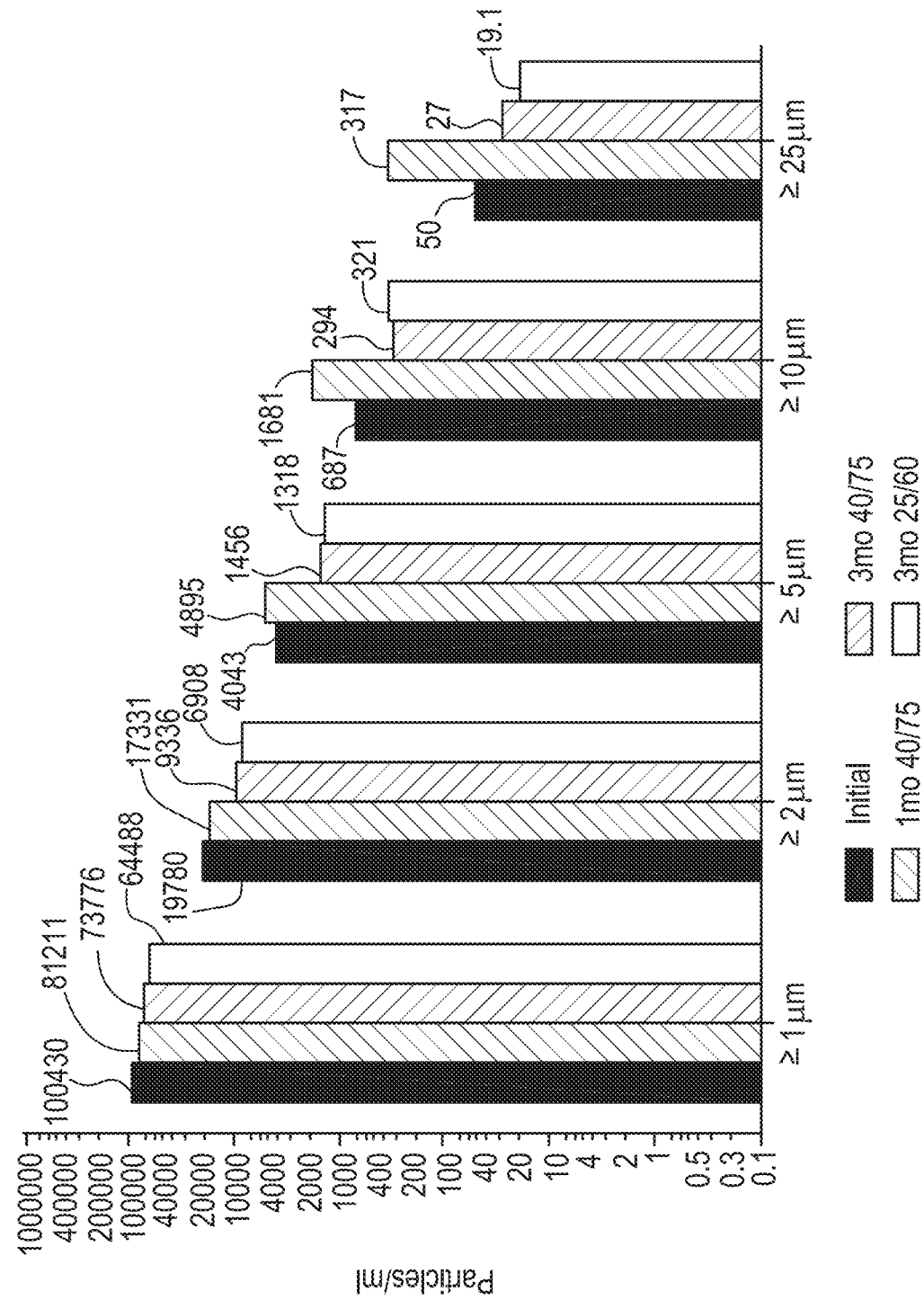

DRY POWDER FORMULATIONS OF THYMIC STROMAL LYMPHOPOIETIN (TSLP)-BINDING ANTIBODIES AND METHODS OF USE THEREOF

CROSS-REFERENCE TO RELATED APPLICATIONS

This application claims benefit under 35 U.S.C. § 119(e) of U.S. Provisional Patent Application No. 62/926,833, filed Oct. 28, 2019, which is incorporated by reference herein in its entirety for all purposes.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 23,350 Byte ASCII (Text) file named "200902-US-NP-SequenceListing.txt," created on Oct. 26, 2020.

FIELD OF THE DISCLOSURE

The present technology relates generally to dry powder formulations of antigen binding fragments derived from antibodies specific for thymic stromal lymphopoietin (TSLP), as well as methods of treating asthma, including mild, moderate and severe asthma, eosinophilic asthma and non/low eosinophilic asthma, using the dry powder formulations via pulmonary delivery. The dry powder formulations include a mixture of leucine and trileucine that result in a formulation particularly suitable for delivering antigen binding fragments derived from anti-TSLP antibodies via inhalation.

BACKGROUND

Asthma affects an estimated 300 million people worldwide, including all age groups, and poses a serious burden on the health care system, and on society through loss of productivity at the workplace and disruption to the family. ("Pocket Guide for Asthma Management and Prevention," Global Initiative for Asthma; 2019). Asthma causes symptoms such as wheezing, shortness of breath, chest tightness and cough that vary over time with their occurrence, frequency and intensity. Symptoms are often associated with bronchoconstriction, airway wall thickening and increased production of mucus. Asthma can have varying degrees of symptoms and be well controlled, or poorly controlled, based on number of attacks and severity.

Thymic stromal lymphopoietin (TSLP), an epithelial cell-derived cytokine produced in response to environmental and pro-inflammatory stimuli, leads to the activation of multiple inflammatory cells and downstream pathways. TSLP is increased in the airways of patients with asthma and correlates with Th2 cytokine and chemokine expression. and disease severity. While TSLP is central to the regulation of Th2 immunity, it may also play a key role in other pathways of inflammation and therefore be relevant to multiple asthma phenotypes.

Delivery of antibodies to TSLP to a patient, in particular via inhalation, would provide an improved method of treatment for asthmatic patients, including those with mild asthma who may require daily, low-dose administration.

BRIEF SUMMARY OF THE DISCLOSURE

In view of the foregoing, in one aspect provided herein is A dry powder formulation comprising a plurality of microparticles, the microparticles comprising: leucine, about 1% to about 10% trileucine by weight and an antigen binding fragment of an anti-thymic stromal lymphopoietin (TSLP) antibody.

In some embodiments, the antigen binding fragment of the anti-thymic stromal lymphopoietin (TSLP) antibody comprises a heavy chain variable domain comprising: a heavy chain CDR1 sequence comprising the amino acid sequence set forth in SEQ ID NO:1, a heavy chain CDR2 sequence comprising the amino acid sequence set forth in SEQ ID NO:2, and a heavy chain CDR3 sequence comprising the amino acid sequence set forth in SEQ ID NO:3, wherein either of heavy chain CDR1, 2 or 3 optionally comprises a single amino acid substitution, and a light chain variable domain comprising, a light chain CDR1 sequence comprising the amino acid sequence set forth in SEQ ID NO:5, a light chain CDR2 sequence comprising the amino acid sequence set forth in SEQ ID NO:6, and a light chain CDR3 sequence comprising the amino acid sequence set forth in SEQ ID NO:7, wherein either of light chain CDR 1, 2 or 3 optionally comprises a single amino acid substitution, wherein the leucine and the trileucine are present at a concentration ratio of leucine:trileucine of about 0.1:1 to about 30:1.

In another aspect, there is provided a method of treating asthma in a patient, comprising administering via inhalation the dry powder formulation of the first aspect.

In another aspect, there is provided a dry powder formulation according to the first aspect, for use in a method of treatment, wherein the formulation is to be administered by inhalation. In some embodiments, the formulation is for use in the treatment of asthma.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The drawings are not necessarily to scale.

FIG. 8B shows the filling of capsules with dry powder formulations described herein.

FIGS. 11A-11D show surface rugosity of microparticles as detected by SEM.

FIG. 14 shows the correlation between fine particle fraction (FPF) and leucine and trileucine wt % values.

FIG. 15A shows the number of sub-visible particles following reconstitution of a formulation comprising 40% (w/w) $Fab_1$ and varying concentrations of polysorbate-80 (PS-80) to a solution concentration of $Fab_1$ of 30 mg/ml (in the Figure "≥" comprises an upper size limit of 200 μm)

FIG. 15B shows the number of sub-visible particles following reconstitution of a formulation comprising 40% (w/w) $Fab_1$ and varying concentrations of PS-80 to a solution concentration of $Fab_1$ of 2.5 mg/ml (in the Figure "≥" comprises an upper size limit of 200 μm)

FIG. 16A shows the number of sub-visible particles following reconstitution of a formulation comprising 40% (w/w) $Fab_1$ and varying concentrations of poloxamer-188 to a solution concentration of $Fab_1$ of 30 mg/ml (in the Figure "≥" comprises an upper size limit of 200 μm)

FIG. 16B shows the number of sub-visible particles following reconstitution of a formulation comprising 40% (w/w) $Fab_1$ and varying concentrations of poloxamer-188 to a solution concentration of $Fab_1$ of 2.5 mg/ml (in the Figure "≥" comprises an upper size limit of 200 μm)

FIG. 17C shows the particle morphology of a formulation comprising 40% (w/w) $Fab_1$ and 1.1% PS-80 following storage for 1 or 3 months at 40° C. and 75% relative humidity (40/75) and for 3 months at 25° C. and 60% relative humidity (25/60)

FIG. 18C shows the particle morphology of a formulation comprising 1% (w/w) $Fab_1$ and 1.1% PS-80 following storage for 1 or 3 months at 40° C. and 75% relative humidity (40/75) and for 3 months at 25° C. and 60% relative humidity (25/60)

FIG. 19A shows the number of sub-visible particles following reconstitution of a formulation comprising 40% $Fab_1$ and 1.1% PS-80 (w/w) to a solution concentration of $Fab_1$ of 30 mg/ml, following storage at 40/75 for 1 or 3 months and 25/60 for 3 months FIG. 19B shows the number of sub-visible particles following reconstitution of a formulation comprising 1% $Fab_1$ and 1.1% PS-80 (w/w) to a solution concentration of $Fab_1$ of 0.75 mg/ml, following storage at 40/75 for 1 or 3 months and 25/60 for 3 months

DETAILED DESCRIPTION

Figure 1:
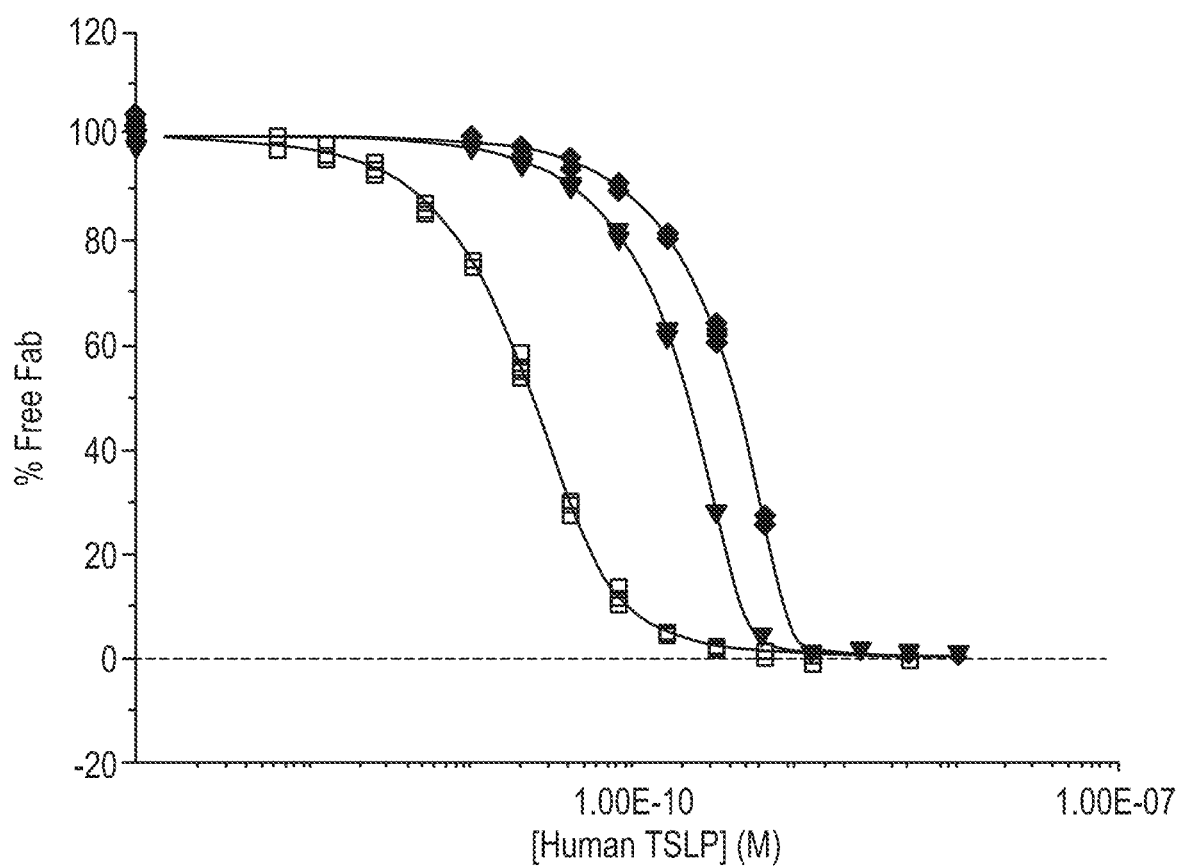
FIG. 1 shows $Fab_1$ binding to hu TSLP as measured by KinExA.

The dry powder formulation described herein addresses an unmet need by enabling the use of anti-TSLP antibody binding fragments for the treatment of asthma in a primary care setting. Subjects suffering from asthma typically manage asthmatic symptoms by self-delivering pharmaceutical compositions, such as long-acting beta agonists and/or glucocorticoids, via inhalation.

Whereas existing biologic medicines, either approved or being clinically investigated, offer a new treatment paradigm for asthma patients, these generally cannot be delivered to subjects by the familiar pulmonary route. Tezepelumab, a next-generation biologic medicine, is a human immunoglobulin G2 (lgG2) monoclonal antibody (mAb) that binds to TSLP, preventing its interaction with the TSLP receptor complex. In a recent phase 2, randomized, double-blind, placebo-controlled trial, asthma subjects who received subcutaneous injections of tezepelumab had lower rates of clinically significant asthma exacerbations than those who received placebo (Corren et al (2017) *NEJM* 377: 936-946).

The invention described herein combines the therapeutic advantages of next-generation biologic medicines, such as tezepelumab, with the administration route more familiar to subjects suffering from asthma. Thus, the invention enables such next-generation therapies to be administered in a primary care setting, thereby extending the availability of these medicines to subjects beyond the reach of specialist care.

In addition, the formulations described herein may be particularly useful for treating patients with less severe asthma who would normally be managed in a primary care setting. For example, patients with a Global Initiative for Asthma (GINA) scale of 3 or less, suitably a GINA scale of 2 or 3, may be particularly amenable for treatment with the formulation described herein. In certain embodiments, patients with a GINA score of 3 are amenable for treatment with the formulation described herein. In certain embodiments, patients with a GINA score of 2 are amenable for treatment with the formulation described herein. Furthermore, by delivering the biologic medicines directly to the lung, side effects associated with systemic administration (such as injection site inflammation) are reduced.

In addition, the formulations provide for the possibility of treating patients with moderate-severe asthma who could be managed in a primary care setting, or for treating patients with moderate-severe asthma with poor access to treatment via specialist care. For example, the formulations may be useful for the treatment of moderate-severe asthma patients with a Global Initiative for Asthma (GINA) scale of 4-5. Suitably, the formulations provide for the possibility of treating moderate-severe asthma that is uncontrolled. Suitably, the formulations provide for the possibility of treating moderate-severe asthma that is uncontrolled on medium dose to high dose ICS:LABA with one or more exacerbations and frequent symptoms.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As described herein, dry powder formulations are provided for the stabilization and delivery of pharmaceutical active agents. Suitably, the dry powder formulations are formulated for pulmonary delivery, including via inhalation via a dry powder inhaler (DPI).

As used herein a "dry powder formulation" refers to a formulation that includes a plurality of solid microparticles in a powder composition that suitably contains less than about 20% moisture, more suitably less than 10% moisture, less than about 5-6% moisture, or less than about 3% moisture. As described herein, dry powder formulations can be utilized for delivery via inhalation to a patient. In other embodiments, the dry powder formulations can be reconstituted and administered in a liquid form, either orally, intravenously, parenterally, etc. As described herein, an advantage of the dry powder formulations provided is the increased throughput for improved manufacturability. A further advantage is that the formulation platform described herein provides for a high compressed bulk density. This means that a greater mass of powder can be packaged per delivery unit (e.g. within a capsule). This means that a high dose of active agent can be delivered per unit delivery to the subject. This surprising advantage may improve patient compliance by lowering the number of unit doses required to be taken. In addition, the high compressed bulk density may enable higher dose of active agent to be delivered, increasing the top-end of administered dose range. This may enable the delivery of active agents at therapeutically effective doses where this was not previously possible.

A "microparticle" as used herein refers to a solid particle having a size mass mean diameter (MMD) of less than 20 μm. Mass mean diameter is a measure of the mean particle size of the microparticles, measured using a suitable method, including for example centrifugal sedimentation, electron microscopy, light scattering, laser diffraction, etc.

The dry powder formulations described herein suitably contain a plurality of microparticles. As used herein "plurality" refers to 2 or more of an item, and suitably refers to 5 or more, 10 or more, 50 or more, 100 or more, 500 or more, 1000 or more, etc.

In embodiments, the dry powder formulations include a plurality of microparticles, the microparticles suitably comprise leucine; about 1% to about 10% trileucine by weight; and the anti-TSLP antibody binding fragment defined herein. Unless otherwise stated, "active agent" refers to an antigen binding fragment derived from an anti-TSLP antibody, as defined herein.

FIG. 7 shows a scanning electron micrograph of microparticles of an exemplary dry powder formulation provided herein. In further embodiments, the dry powder formulations including a plurality or microparticles suitably comprise about 1% to about 25% leucine; about 1% to about 10% trileucine; and the active agent.

As used herein "leucine," whether present as a single amino acid or as an amino acid component of a peptide, refers to the amino acid leucine ($C_6H_{13}NO_2$), which may be a racemic mixture or in either its D- or L-form, as well as modified forms of leucine (i.e., where one or more atoms of leucine have been substituted with another atom or functional group). The chemical structure of leucine is provided below:

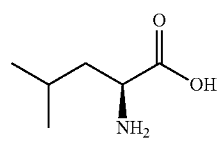

"Trileucine" as utilized herein refers to the chemical compound in which three leucine molecules are linked together in a peptide, as leucine-leucine-leucine (Leu-Leu-Leu), $C_{18}H_{35}N_3O_4$. The chemical structure of trileucine is provided below:

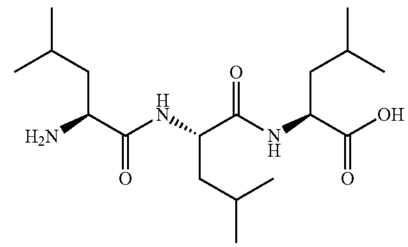 [SMILES: CC(C)C[C@H](NC(=O)[C@H](CC(C)C)NC(=O)[C@@H](N)CC(C)C)C(=O)O]

The amounts of leucine and trileucine provided herein, unless otherwise stated, are provided as weight percentages (wt %) of the formulations. As the dry powder formulations contain substantially little if any water, the weight components of the dry powder formulations are thus dry weight percentages of the final formulations.

In embodiments of the formulation comprising leucine; trileucine; and the antigen binding fragment, the leucine and trileucine are kept at a desired ratio range that provides the improved compressed bulk density characteristics described herein, as well as providing the desired microparticle characteristics that allow for improved storage and delivery. In embodiments, the weight ratio of leucine and trileucine in the microparticles, i.e., leucine:trileucine, is about 0.1:1 to about 30:1. In further embodiments, the leucine and the trileucine are present at a weight ratio of leucine:trileucine of about 0.1:1 to about 25:1, about 0.5:1 to about 20:1, about 1:1 to about 20:1, about 1:1 to about 15:1, about 1:1 to about 12:1, about 1:1 to about 10:1, about 1:1 to about 7:1, about 1:1 to about 6:1, or about 1:1, about 2:1, about 3:1, about 4:1, about 5:1, about 5.1:1, about 5.2:1 about 5.25:1, about 5.3:1, about 5.4:1, about 5.5:1, about 5.75:1 or about 6:1.

Unless otherwise stated, the ratios described herein are expressed as ratios by weight % (w/w—also referred to as a "weight ratio"), that is, weight of leucine:weight of trileucine in the formulations described herein. The ratios are achieved by providing a desired mg/mL concentration of leucine and trileucine in a feedstock, and then drying to remove the feedstock solvent resulting in an atomized microparticle where the starting concentration ratio (expressed in mg/mL), is maintained as a final ratio of leucine: trileucine by weight.

Exemplary weight percentages for leucine and trileucine that can be utilized in the dry powder formulations to achieve these ratios are described herein. Suitably, the dry powder formulations comprise about 5% to about 15% leucine and about 1% to about 5% trileucine. In embodiments, the dry powder formulations comprise about 8% to about 11% leucine and about 2% to about 4% trileucine, and in embodiments, the dry powder formulations comprise about 10.5% leucine and about 2% trileucine.

In exemplary embodiments, the dry powder formulations comprise about 1% to about 10% trileucine by weight, more suitably about 1% to about 9%, about 1% to about 8%, about 1% to about 7%, about 1% to about 6%, about 1% to about 5%, about 2% to about 10%, about 2% to about 9%, about 2% to about 8%, about 2% to about 7%, about 2% to about 6%, about 2% to about 5%, about 2% to about 4%, or about 1%, about 1.5%, about 2%, about 2.5%, about 3%, about 3.5%, about 4%, about 4.5%, about 5%, about 5.5%, or about 6%, trileucine, by weight.

In exemplary embodiments, the dry powder formulations comprise about 1% to about 25% leucine by weight, more suitably about 2% to about 20%, about 3% to about 20%, about 4% to about 20%, about 5% to about 20%, about 5% to about 15%, about 7% to about 12%, about 8% to about 11%, about 9% to about 11%, about 10% to about 11%, or about 5%, about 6%, about 7%, about 8%, about 8.5%, about 9%, about 10%, about 10.5%, about 11%, about 11.5%, about 12%, about 12.5% or about 13%, leucine by weight.

In suitable embodiments, the dry powder formulations comprise about 8% to about 11% leucine and about 2% to about 4% trileucine by weight, more suitably about 9% to about 11% leucine, and about 2% to about 3% trileucine by weight. In exemplary embodiments, the dry powder formulations comprise about 10.5% leucine and about 2% trileucine by weight.

As described herein, it has been surprisingly found that the use of the combination of leucine and trileucine in a dry powder formulation allows for the reduction in the overall amount of leucine and trileucine required to prepare microparticles, as compared to dry powder formulations that contain only one of these components, while still providing the desired stability. In certain embodiments, the formulations of the present invention have increased compressed bulk density in comparison to formulations in the art, which may enable the delivery of a higher concentration of an active agent to the lungs of a patient following inhalation. These improved characteristics appear to be related to the incorporation of leucine and trileucine into the microparticles.

An exemplary process of preparing a dry powder formulation, in accordance with embodiments hereof may take place as follows. A liquid feedstock containing the desired final components of the dry powder formulation are atomized using an atomizer, to a fine mist. The mist is then dried as described herein. The atomized droplets contain the dissolved components, initially as a liquid droplet. As the droplet dries, different components of the formulation begin to saturate and precipitate at varying rates. As described herein, a shell begins to form around an outer surface of the microparticles of the dry powder formulations. This shell suitably includes the leucine and trileucine components at an outer surface of the shell. It should be noted that leucine and trileucine become preferentially located at an outer surface of the microparticles, while smaller amounts of leucine and trileucine can also found throughout the microparticles. In embodiments, a higher concentration of leucine and trileucine are suitably found at or near the surface of the microparticles, rather than near the center of the microparticles. In embodiments, the center of the microparticles contain a substantial amount of the active agent, along with other excipient components as described herein, suitably in an amorphous form. As used herein, a "substantial amount" of the active agent means at least about 60% of the active agent (i.e., of the total active agent in the formulation) is located at or near the center of the microparticles, suitably at least about 70%, and more suitably at least about 75%, at least about 80%, at least about 85%, at least about 90%, at least about 95%, and in embodiments about 95%-100%, of the active agent is located at or near the center of the microparticles.

In further embodiments, the microparticles contain leucine and trileucine located substantially throughout the microparticles, but with higher amounts at or near the surface of the microparticles. As used herein "substantially throughout the microparticles" means that the leucine and/or trileucine are located in a gradient from the outer surface of the microparticles toward the center of the microparticles, but suitably with decreasing amounts of the leucine and/or trileucine as you move toward the center, and in embodiments, no leucine or trileucine are found at the center of the microparticles where the active agent is located. In other embodiments, the amounts and leucine and trileucine can be substantially uniform throughout a cross-section of the microparticles.

In embodiments, substantially each of the microparticles of the dry powder formulations comprise leucine and trileucine. That is, suitably at least about 60% of the microparticles contain leucine and trileucine, or at least about 70%, and more suitably at least about 75%, at least about 80%, at least about 85%, at least about 90%, at least about 95%, and in embodiments about 95%-100%, of the microparticles comprise leucine and trileucine. In embodiments each of the microparticles of the dry powder formulations comprise leucine and trileucine.

In additional embodiments, leucine and/or trileucine can be found in the dry powder formulations, but not contained within or associated with a microparticle of the formulation. Thus, in embodiments, free leucine and/or trileucine that is not associated with a microparticle can be found in the dry powder formulations. However, in general, the amount of free leucine and/or trileucine (i.e., not associated with a microparticle) is on the order of less than about 10%, less than about 5%, less than about 1%, and more suitably less than about 0.1% of the total amount of leucine and/or trileucine in the formulations.

In certain embodiments, the dry powder formulations described herein have a compressed bulk density that allows for the delivery of a large amount of active agent. "Compressed bulk density" refers to the mass per unit volume (suitably g/cm$^3$) of a powder when measured under the following conditions. A suitable assay for measuring compressed bulk density (cBD) is described in the examples (see, e.g., Example 6). Suitably, the compressed bulk density (CBD) of the powders is measured using a density analyzer, such as a GeoPyc® Model 1360 density analyzer (Micromeritics, Norcross, GA). Powder samples are suitably prepared in a low humidity environment (<5% RH), before transfer into the density analyzer sample chamber that has been purged with nitrogen gas. The net weight of the powder sample is recorded, and then a compression force of 10-14N, suitably 12N, is applied to the sample by a plunger, at a rate of 250-350 consolidation steps per second, suitably 300 consolidation steps per second. The linear distance travelled by the plunger for each consolidation step is translated into a volume displacement of the powder sample. An average of the measurements from each consolidation step is then transformed into a calculated bulk density value for the dry powder formulation, expressed in g/cm$^3$.

Suitably, the compressed bulk density of a dry powder formulation described herein is at least 0.4 g/cm$^3$, and suitably between about 0.4 g/cm$^3$ to about 1.0 g/cm$^3$, and more suitably about 0.4-0.9 gm/cm$^3$, about 0.4-0.8 gm/cm$^3$, about 0.5-0.8 gm/cm$^3$, about 0.6-0.8 gm/cm$^3$, or about 0.4 gm/cm$^3$, about 0.5 gm/cm$^3$, about 0.6 gm/cm$^3$, about 0.7 gm/cm$^3$, or about 0.8 gm/cm$^3$. In certain embodiments, the compressed bulk density of a dry powder formulation described herein is from about 0.4 gm/cm$^3$ to about 0.9 gm/cm$^3$. In certain embodiments, the compressed bulk density of a dry powder formulation described herein is from about 0.5 gm/cm$^3$ to about 0.8 gm/cm$^3$.

Figure 8A:
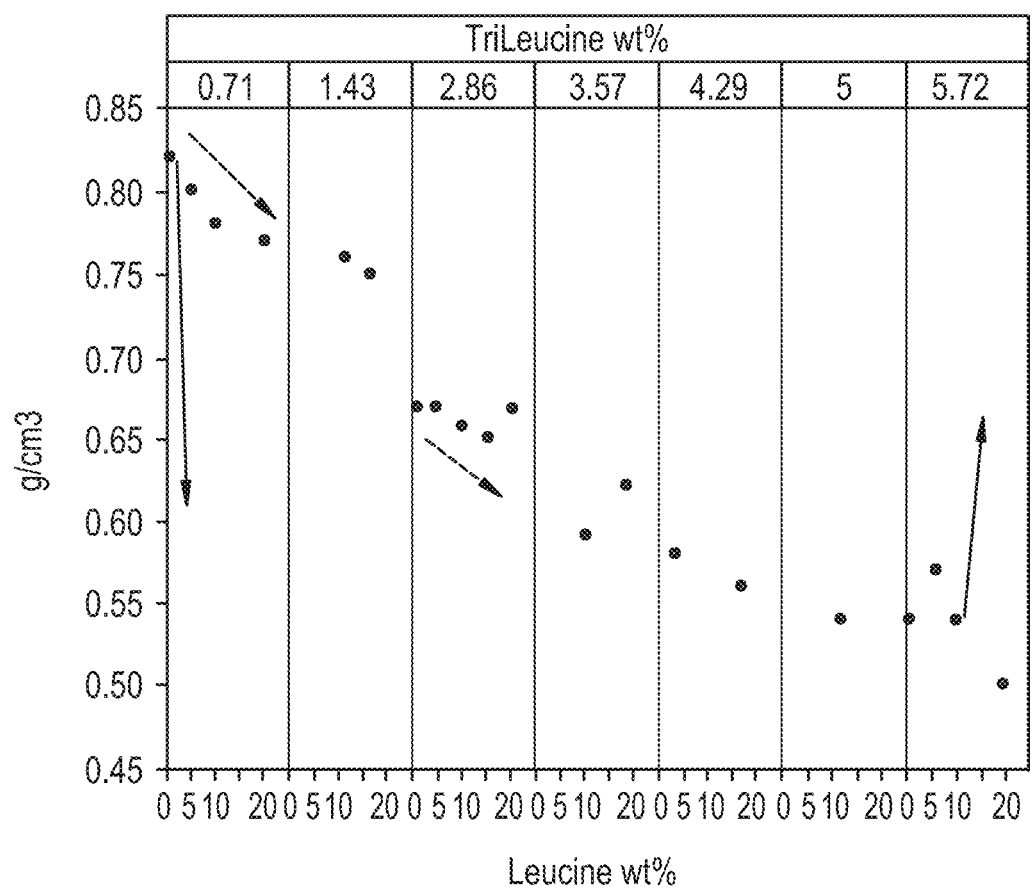
FIG. 8A shows the results of compressed bulk density as a function of leucine and trileucine in the dry powder formulations.

FIG. 8A shows the results of compressed bulk density as a function of leucine and trileucine in the dry powder formulations described herein. Each of the columns represents an amount of trileucine in the formulations. Within each column, the amount of leucine is increased from about 1% to about 20%. As shown, increasing the amount of trileucine results in a lower compressed bulk density, and increasing leucine within each group also reduces the compressed bulk density. To achieve a compressed bulk density of between about 0.5 g/cm$^3$ to about 0.8 g/cm$^3$ the amount of trileucine should be maintained at below 4% by weight.

The formulations described herein comprise an antigen binding fragment of an anti-thymic stromal lymphopoietin (anti-TSLP) antibody. Advantageously, the inventors have found that the formulations described herein enable delivery of the antigen binding fragment via inhalation directly into the lung. Delivery of a therapeutically active antigen binding fragment of an anti-TSLP antibody via inhalation advantageously allows for the use of biologic medicines for the treatment of asthma in a primary care setting.

The sequence of the TSLP polypeptide is provided below:

(SEQ ID NO: 27)
```
Met Phe Pro Phe Ala Leu Leu Tyr Val Leu Ser Val Ser Phe Arg Lys Ile Phe Ile Leu Gln Leu

Val Gly Leu Val Leu Thr Tyr Asp Phe Thr Asn Cys Asp Phe Glu Lys Ile Lys Ala Ala Tyr Leu

Ser Thr Ile Ser Lys Asp Leu Ile Thr Tyr Met Ser Gly Thr Lys Ser Thr Glu Phe Asn Asn Thr

Val Ser Cys Ser Asn Arg Pro His Cys Leu Thr Glu Ile Gln Ser Leu Thr Phe Asn Pro Thr Ala

Gly Cys Ala Ser Leu Ala Lys Glu Met Phe Ala Met Lys Thr Lys Ala Ala Leu Ala Ile Trp Cys

Pro Gly Tyr Ser Glu Thr Gln Ile Asn Ala Thr Gln Ala Met Lys Lys Arg Arg Lys Arg Lys Val

Thr Thr Asn Lys Cys Leu Glu Gln Val Ser Gln Leu Gln Gly Leu Trp Arg Arg Phe Asn Arg

Pro Leu Leu Lys Gln Gln
```

The term "antibody" as used herein refers to a protein comprising at least two heavy chains and two light chains connected by disulfide bonds. The term "antibody" includes naturally occurring antibodies as well as all recombinant forms of antibodies, e.g., humanized antibodies, fully human antibodies and chimeric antibodies. Each heavy chain is usually comprised of a heavy chain variable region (VH) and a heavy chain constant region (CH). Each light chain is usually comprised of a light chain variable region (VL) and a light chain constant region (CL). The term "antibody", however, also includes other types of antibodies such as single domain antibodies, heavy chain antibodies, i.e. antibodies only composed of one or more, in particular two heavy chains, and nanobodies, i.e. antibodies only composed of a single monomeric variable domain.

Antibody binding fragments include (i) Fab fragments, monovalent fragments consisting of the variable region and the first constant domain of each the heavy and the light chain; (ii) F(ab)2 fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)2 fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular. In embodiments, the antibody binding fragment of the invention is selected from is selected from Fab, Fab', F(ab')2, scFv, minibody, or diabody. In certain embodiments, the antibody binding fragment is a Fab. In some embodiments, the anti-TSLP antibody from which the antigen binding fragment is derived is an IgG1.

Sequences of an exemplary Fab of the invention (herein termed $Fab_1$) include:

```
HCDR1 FAB1
                                                      (SEQ ID NO: 1)
Thr Tyr Gly Met His

HCDR2 FAB1
                                                      (SEQ ID NO: 2)
Val Ile Trp Tyr Asp Gly Ser Asn Lys His Tyr Ala Asp Ser Val Lys Gly

HCDR3 FAB1
                                                      (SEQ ID NO: 3)
Ala Pro Gln Trp Glu Leu Val His Glu Ala Phe Asp Ile

HEAVY CHAIN VH FAB1
                                                      (SEQ ID NO: 4)
Gln Met Gln Leu Val Glu Ser Gly Gly Gly Val Val Gln Pro Gly Arg Ser Leu Arg Leu Ser Cys

Ala Ala Ser Gly Phe Thr Phe Arg Thr Tyr Gly Met His Trp Val Arg Gln Ala Pro Gly Lys Gly

Leu Glu Trp Val Ala Val Ile Trp Tyr Asp Gly Ser Asn Lys His Tyr Ala Asp Ser Val Lys Gly

Arg Phe Thr Ile Thr Arg Asp Asn Ser Lys Asn Thr Leu Asn Leu Gln Met Asn Ser Leu Arg

Ala Glu Asp Thr Ala Val Tyr Tyr Cys Ala Arg Ala Pro Gln Trp Glu Leu Val His Glu Ala Phe

Asp Ile Trp Gly Gln Gly Thr Met Val Thr Val Ser Ser

LCDR1 FAB1
                                                      (SEQ ID NO: 5)
Gly Gly Asn Asn Leu Gly Ser Lys Ser Val His

LCDR2 FAB1
```

-continued

LCDR3 FAB1 (SEQ ID NO: 6)
Asp Asp Ser Asp Arg Pro Ser

LCDR3 FAB1 (SEQ ID NO: 7)
Gln Val Trp Asp Ser Ser Ser Asp His Val Val

LIGHT CHAIN VL FAB1 (SEQ ID NO: 8)
Ser Tyr Val Leu Thr Gln Pro Pro Ser Val Ser Val Ala Pro Gly Gln Thr Ala Arg Ile Thr Cys
Gly Gly Asn Asn Leu Gly Ser Lys Ser Val His Trp Tyr Gln Gln Lys Pro Gly Gln Ala Pro Val
Leu Val Val Tyr Asp Asp Ser Asp Arg Pro Ser Trp Ile Pro Glu Arg Phe Ser Gly Ser Asn Ser
Gly Asn Thr Ala Thr Leu Thr Ile Ser Arg Gly Glu Ala Gly Asp Glu Ala Asp Tyr Tyr Cys Gln
Val Trp Asp Ser Ser Ser Asp His Val Val Phe Gly Gly Gly Thr Lys Leu Thr Val Leu

FAB1 VARIABLE HEAVY CHAIN VH (nucleic acid) (SEQ ID NO: 9)

```
cagatgcagt tggttgaatc tggtggcggc gtggtgcagc ctggcagatc tctgagactg      60
tcttgtgccg cctccggctt caccttcaga acctacggaa tgcactgggt ccgacaggcc     120
cctggcaaag gattggaatg ggtcgccgtg atttggtacg acggctccaa caagcactac     180
gccgactccg tgaagggcag attcaccatc accagagaca actccaagaa caccctgaac     240
ctgcagatga actccctgag agccgaggac accgccgtgt actattgtgc tagagcccct     300
cagtgggaac tcgtgcatga ggcctttgac atctggggcc agggaacaat ggtcaccgtc     360
tcctca                                                                 366
```

FAB1 VARIABLE LIGHT CHAIN VL (nucleic acid) (SEQ ID NO: 10)

```
tcatatgttc ttacacaacc accgtcggtt tcggttgctc aggacaaac agctcgaatt        60
acatgcggag gaaacaacct cggatcgaag tcggttcact ggtatcaaca aaagccagga     120
caagctccag ttctcgtggt gtacgatgat tcagatcgac catcatggat cccagagcga     180
ttctcaggat caaactcggg aaatactgcc acgctcacaa tttcacgcgg agaagcggga     240
gatgaagctg attactattg ccaagtgtgg gactcgtcgt cagatcatgt tgttttcgga     300
ggtggaacaa agctcacagt gctc                                             324
```

FAB1 HEAVY CHAIN (polypeptide) (SEQ ID NO: 28)
Gln Met Gln Leu Val Glu Ser Gly Gly Gly Val Val Gln Pro Gly Arg Ser Leu Arg Leu Ser Cys
Ala Ala Ser Gly Phe Thr Phe Arg Thr Tyr Gly Met His Trp Val Arg Gln Ala Pro Gly Lys Gly
Leu Glu Trp Val Ala Val Ile Trp Tyr Asp Gly Ser Asn Lys His Tyr Ala Asp Ser Val Lys Gly
Arg Phe Thr Ile Thr Arg Asp Asn Ser Lys Asn Thr Leu Asn Leu Gln Met Asn Ser Leu Arg
Ala Glu Asp Thr Ala Val Tyr Tyr Cys Ala Arg Ala Pro Gln Trp Glu Leu Val His Glu Ala Phe
Asp Ile Trp Gly Gln Gly Thr Met Val Thr Val Ser Ser Ala Ser Thr Lys Gly Pro Ser Val Phe
Pro Leu Ala Pro Ser Ser Lys Ser Thr Ser Gly Gly Thr Ala Ala Leu Gly Cys Leu Val Lys Asp
Tyr Phe Pro Glu Pro Val Thr Val Ser Trp Asn Ser Gly Ala Leu Thr Ser Gly Val His Thr Phe
Pro Ala Val Leu Gln Ser Ser Gly Leu Tyr Ser Leu Ser Ser Val Val Thr Val Pro Ser Ser Ser
Leu Gly Thr Gln Thr Tyr Ile Cys Asn Val Asn His Lys Pro Ser Asn Thr Lys Val Asp Lys Arg
Val Glu Pro Lys Ser Cys Asp Lys FAB1 LIGHT CHAIN (polypeptide) (SEQ ID NO: 29)
Ser Tyr Val Leu Thr Gln Pro Pro Ser Val Ser Val Ala Pro Gly Gln Thr Ala Arg Ile Thr Cys
Gly Gly Asn Asn Leu Gly Ser Lys Ser Val His Trp Tyr Gln Gln Lys Pro Gly Gln Ala Pro Val
Leu Val Val Tyr Asp Asp Ser Asp Arg Pro Ser Trp Ile Pro Glu Arg Phe Ser Gly Ser Asn Ser

```
Gly Asn Thr Ala Thr Leu Thr Ile Ser Arg Gly Glu Ala Gly Asp Glu Ala Asp Tyr Tyr Cys Gln

Val Trp Asp Ser Ser Ser Asp His Val Val Phe Gly Gly Gly Thr Lys Leu Thr Val Leu Gly Gln

Pro Lys Ala Ala Pro Ser Val Thr Leu Phe Pro Pro Ser Ser Glu Glu Leu Gln Ala Asn Lys Ala

Thr Leu Val Cys Leu Ile Ser Asp Phe Tyr Pro Gly Ala Val Thr Val Ala Trp Lys Ala Asp Ser

Ser Pro Val Lys Ala Gly Val Glu Thr Thr Thr Pro Ser Lys Gln Ser Asn Asn Lys Tyr Ala Ala

Ser Ser Tyr Leu Ser Leu Thr Pro Glu Gln Trp Lys Ser His Arg Ser Tyr Ser Cys Gln Val Thr

His Glu Gly Ser Thr Val Glu Lys Thr Val Ala Pro Thr Glu Cys Ser
```

FAB1 HEAVY CHAIN (nucleic acid)

(SEQ ID NO: 30)

```
cagatgcagt tggttgaatc tggtggcggc gtggtgcagc ctggcagatc tctgagactg      60
tcttgtgccg cctccggctt caccttcaga acctacggaa tgcactgggt ccgacaggcc     120
cctggcaaag gattggaatg ggtcgccgtg atttggtacg acggctccaa caagcactac     180
gccgactccg tgaagggcag attcaccatc accagagaca actccaagaa caccctgaac     240
ctgcagatga actccctgag agccgaggac accgccgtgt actattgtgc tagagcccct     300
cagtgggaac tcgtgcatga ggcctttgac atctggggcc agggaacaat ggtcaccgtc     360
tcctcagcct ccaccaaggg cccatcggtc ttccccctgg cacctcctc caagagcacc     420 tctgggggca cagcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgacagtgc cctccagcag cttgggcacc     600
cagacctaca tctgcaacgt gaatcacaag cccagcaaca ccaaggtgga caagagagtt     660
gagcccaaat cttgtgacaa a                                                681
```

FAB1 LIGHT CHAIN (nucleic acid)

(SEQ ID NO: 31)

```
tcatatgttc ttacacaacc accgtcggtt tcggttgctc caggacaaac agctcgaatt      60
acatgcggag gaaacaacct cggatcgaag tcggttcact ggtatcaaca aaagccagga     120
caagctccag ttctcgtggt gtacgatgat tcagatcgac catcatggat cccagagcga     180
ttctcaggat caaactcggg aaatactgcc acgctcacaa tttcacgcgg agaagcggga     240
gatgaagctg attactattg ccaagtgtgg gactcgtcgt cagatcatgt tgttttcgga     300
ggtggaacaa agctcacagt gctcggtcag cccaaggctg ccccctcggt cactctgttc     360 ccgcccctcct ctgaggagct tcaagccaac aaggccacac tggtgtgtct cataagtgac     420
ttctacccgg gagccgtgac agtggcctgg aaggcagata gcagcccgt caaggcggga     480 gtggagacca ccacaccctc caaacaaagc aacaacaagt acgcggccag cagctatctg     540
agcctgacgc ctgagcagtg gaagtcccac agaagctaca gctgccaggt cacgcatgaa     600
gggagcaccg tggagaagac agtggcccct acagaatgtt ca                         642
```

The dry powder formulations provided herein comprise a plurality of microparticles, the microparticles comprising: leucine; about 1% to about 10% trileucine by weight; and the antigen binding fragment of an anti-thymic stromal lymphopoietin (TSLP) antibody, wherein the leucine and the trileucine are present at a concentration ratio of leucine: trileucine of about 0.1:1 to about 30:1.

In certain embodiments, the antigen binding fragment within the dry powder formulation comprises a. a heavy chain variable domain comprising:
   a heavy chain CDR1 sequence comprising the amino acid sequence set forth in SEQ ID NO:1, a heavy chain CDR2 sequence comprising the amino acid sequence set forth in SEQ ID NO:2, and a heavy chain CDR3 sequence comprising the amino acid sequence set forth in SEQ ID NO:3, wherein either of heavy chain CDR1, 2 or 3 optionally comprises a single amino acid substitution, and b. a light chain variable domain comprising:
   a light chain CDR1 sequence comprising the amino acid sequence set forth in SEQ ID NO:5, a light chain CDR2 sequence comprising the amino acid sequence set forth in SEQ ID NO:6, and a light chain CDR3 sequence comprising the amino acid sequence set forth in SEQ ID NO:7; wherein either of light chain CDR 1, 2 or 3 optionally comprises a single amino acid substitution.

In certain embodiments, the antigen binding fragment within the dry powder formulation comprises a heavy chain variable domain comprising a light chain CDR1 sequence having the amino acid sequence set forth in SEQ ID NO:1, a heavy chain CDR2 sequence having the amino acid sequence set forth in SEQ ID NO:2, and a heavy chain CDR3 sequence having the amino acid sequence set forth in SEQ ID NO:3, and a light chain CDR1 sequence having the amino acid sequence set forth in SEQ ID NO:5, a light chain CDR2 sequence having the amino acid sequence set forth in SEQ ID NO:6, and a light chain CDR3 sequence having the amino acid sequence set forth in SEQ ID NO:7.

In additional embodiments, the antigen binding fragment for use in the dry powder formulations comprises a heavy chain variable domain comprising SEQ ID NO:4; and a light chain variable domain comprising SEQ ID NO:8. In additional embodiments, the antigen binding fragment for use in the dry powder formulations comprises a heavy chain having the sequence set forth in SEQ ID NO:28; and a light chain having the sequence set

```
HCDR2 FAB5
                                                                    (SEQ ID NO: 17)
Val Ile Trp Tyr Asp Gly Ser Asn Lys His Tyr Ala Asp Ser Val Lys Ala

HEAVY CHAIN VH FAB5
                                                                    (SEQ ID NO: 18)
Gln Met Gln Leu Val Glu Ser Gly Gly Val Val Gln Pro Gly Arg Ser Leu Arg

Leu Ser Cys Ala Ala Ser Gly Phe Thr Phe Arg Thr Tyr Gly Met His Trp Val Arg Gln Ala Pro

Gly Lys Gly Leu Glu Trp Val Ala Val Ile Trp Tyr Asp Gly Ser Asn Lys His Tyr Ala Asp Ser

Val Lys Ala Arg Phe Thr Ile Thr Arg Asp Asn Ser Lys Asn Thr Leu Asn Leu Gln Met Asn Ser

Leu Arg Ala Glu Asp Thr Ala Val Tyr Tyr Cys Ala Arg Ala Pro Gln Trp Glu Leu Val His Glu

Ala Phe Asp Ile Trp Gly Gln Gly Thr Met Val Thr Val Ser Ser

LCDR1 FAB6
                                                                    (SEQ ID NO: 19)
Gly Gly Gln Asn Leu Gly Ser Lys Ser Val His

LIGHT CHAIN VL FAB6
                                                                    (SEQ ID NO: 20)
Ser Tyr Val Leu Thr Gln Pro Pro Ser Val Ser Val Ala Pro Gly Gln Thr Ala Arg Ile

Thr Cys Gly Gly Gln Asn Leu Gly Ser Lys Ser Val His Trp Tyr Gln Gln Lys Pro Gly Gln Ala

Pro Val Leu Val Val Tyr Asp Asp Ser Asp Arg Pro Ser Trp Ile Pro Glu Arg Phe Ser Gly Ser

Asn Ser Gly Asn Thr Ala Thr Leu Thr Ile Ser Arg Gly Glu Ala Gly Asp Glu Ala Asp Tyr Tyr

Cys Gln Val Trp Asp Ser Ser Ser Asp His Val Val Phe Gly Gly Gly Thr Lys Leu Thr Val Leu

LCDR1 FAB7
                                                                    (SEQ ID NO: 21)
Gly Gly Asn Gln Leu Gly Ser Lys Ser Val His

LIGHT CHAIN VL FAB7
                                                                    (SEQ ID NO: 22)
Ser Tyr Val Leu Thr Gln Pro Pro Ser Val Ser Val Ala Pro Gly Gln Thr Ala Arg Ile

Thr Cys Gly Gly Asn Gln Leu Gly Ser Lys Ser Val His Trp Tyr Gln Gln Lys Pro Gly Gln Ala

Pro Val Leu Val Val Tyr Asp Asp Ser Asp Arg Pro Ser Trp Ile Pro Glu Arg Phe Ser Gly Ser

Asn Ser Gly Asn Thr Ala Thr Leu Thr Ile Ser Arg Gly Glu Ala Gly Asp Glu Ala Asp Tyr Tyr

Cys Gln Val Trp Asp Ser Ser Ser Asp His Val Val Phe Gly Gly Gly Thr Lys Leu Thr Val Leu

LCDR3 FAB8
                                                                    (SEQ ID NO: 23)
Gln Val Trp Asp Thr Ser Ser Asp His Val Val

LIGHT CHAIN VL FAB8
                                                                    (SEQ ID NO : 24)
Ser Tyr Val Leu Thr Gln Pro Pro Ser Val Ser Val Ala Pro Gly Gln Thr Ala Arg Ile Thr Cys

Gly Gly Asn Asn Leu Gly Ser Lys Ser Val His Trp Tyr Gln Gln Lys Pro Gly Gln Ala Pro Val

Leu Val Val Tyr Asp Asp Ser Asp Arg Pro Ser Trp Ile Pro Glu Arg Phe Ser Gly Ser Asn Ser

Gly Asn Thr Ala Thr Leu Thr Ile Ser Arg Gly Glu Ala Gly Asp Glu Ala Asp Tyr Tyr Cys Gln

Val Trp Asp Thr Ser Ser Asp His Val Val Phe Gly Gly Gly Thr Lys Leu Thr Val Leu

LCDR3 FAB9
                                                                    (SEQ ID NO: 25)
Gln Val Trp Asp Ser Thr Ser Asp His Val Val

LIGHT CHAIN VL FAB9
                                                                    (SEQ ID NO: 26)
Ser Tyr Val Leu Thr Gln Pro Pro Ser Val Ser Val Ala Pro Gly Gln Thr Ala Arg Ile

Thr Cys Gly Gly Asn Asn Leu Gly Ser Lys Ser Val His Trp Tyr Gln Gln Lys Pro Gly Gln Ala

Pro Val Leu Val Val Tyr Asp Asp Ser Asp Arg Pro Ser Trp Ile Pro Glu Arg Phe Ser Gly Ser
```

-continued

```
Asn Ser Gly Asn Thr Ala Thr Leu Thr Ile Ser Arg Gly Glu Ala Gly Asp Glu Ala Asp Tyr Tyr

Cys Gln Val Trp Asp Ser Thr Ser Asp His Val Val Phe Gly Gly Gly Thr Lys Leu Thr Val Leu.
```

In certain embodiments, the heavy variable chain and the light variable chain domains of the antigen binding fragment of the invention comprise any of the combinations of CDR sequences set out in the following table:

|  | VH CDRs 1,2 and 3 | VL CDRs 1, 2 and 3 |
| --- | --- | --- |
| Fab$_1$ | SEQ ID NOs: 1, 2 and 3 | SEQ ID NOs: 5, 6 and 7 |
| Fab$_2$ | SEQ ID NOs: 1, 2 and 3 | SEQ ID NO: 11, 6 and 7 |
| Fab$_3$ | SEQ ID NOs: 1, 2 and 3 | SEQ ID NO: 14, 6 and 7 |
| Fab$_4$ | SEQ ID NO: 1, 15 and 3 | SEQ ID NOs: 5, 6 and 7 |
| Fab$_5$ | SEQ ID NOs: 1, 17 and 3 | SEQ ID NOs: 5, 6 and 7 |
| Fab$_6$ | SEQ ID NOs: 1, 2 and 3 | SEQ ID NOs: 19, 6 and 7 |
| Fab$_7$ | SEQ ID NOs: 1, 2 and 3 | SEQ ID NOs: 19, 6 and 7 |
| Fab$_8$ | SEQ ID NOs: 1, 2 and 3 | SEQ ID NOs: 5, 6 and 23 |
| Fab$_9$ | SEQ ID NOs: 1, 2 and 3 | SEQ ID NOs: 5, 6 and 25 |

The formulation disclosed herein may be administered in combination with an additional active agent for use in treating asthma. Exemplary active agents that can be administered in combination with the dry powder formulation described herein include, but are not limited to, inhaled corticosteroids (ICS), bronchodilators (including long-acting beta agonists (LABA), long-acting anti-muscarinic agonists (LAMA), short-acting beta agonist (SABA), and muscarinic β2-agonists (MABA)), antihistamines, antileukotrienes, PDE-4 inhibitors, janus kinase inhibitors and phosphoinositide 3-kinase inhibitors. In certain embodiments, the additional active agent is combined into the formulation of the invention together with the anti-TSLP antibody binding fragment disclosed herein.

In suitable embodiments, the dry powder formulations described herein further comprise a glass stabilization agent to aid in stabilizing the formulation, and in particular, in stabilizing the active agent. A "glass stabilization agent" refers to an excipient that stabilizes an active agent (suitably a polypeptide) in a dry powder formulation, suitably by substituting for water at the active agent surface during drying, or otherwise impeding the degradation process, and forms an amorphous solid that includes the active agent. Examples of glass stabilization agents include amorphous saccharides, polymeric sugars, buffers, salts, or synthetic polymers (e.g., poly-L-glycolic acid), as well as mixtures of such components. In suitable embodiments, the glass stabilization agent is an amorphous saccharide. In additional embodiments, the glass stabilization agent is a buffer. In still further embodiments, the formulations described herein can include both an amorphous saccharide and a buffer, which together or separately may act as a glass stabilization agent.

Exemplary amorphous saccharides for use in the formulations described herein include, but are not limited to, trehalose, sucrose, raffinose, inulin, dextran, mannitol, and cyclodextrin. Suitably the amorphous saccharide is present at about 30% to about 70% (weight percentage) of the dry powder formulation. In further embodiments, the amorphous saccharide is present at about 30% to about 65%, about 35% to about 65%, about 35% to about 60%, about 40% to about 60%, about 30% to about 50%, or about 30%, about 35%, about 40%, about 45%, about 50%, about 55%, or about 60%. Suitably the amorphous saccharide is trehalose, and is present in the formulations at about 30%-60%, more suitably about 35%-55%, or about 35%, about 40%, about 45% or about 50%, of the weight of the dry powder formulation.

Exemplary buffers that can be included in the dry powder formulations, suitably as glass stabilization agents, include various citrate buffers (such as sodium citrate), a phosphate buffer, a histidine buffer, a glycine buffer, an acetate buffer, and a tartrate buffer, as well as combinations of such buffers. Amounts of the buffers that can be included in the dry powder formulations can range from about 0.1% to about 20%, more suitably about 0.5% to about 15%, about 1% to about 10%, about 2% to about 8%, about 3% to about 7%, or about 1%, about 2%, about 3%, about 4%, about 5%, about 6%, about 7%, about 8%, about 9% or about 10%.

Buffers also provide control of the pH of the dry powder formulations, suitably maintaining a pH of between about pH 5 and about 8, for example, a pH of between about pH 5 to about pH 6, or about pH 5.5 to about pH 6.5, or about pH 6 to about pH 7, or about pH 6.5 to about pH 7.5, or about pH 7 to about pH 8.

In additional embodiments, dry powder formulations are provided that comprise about 30%-50%, trehalose, about 10%-11% leucine, about 1%-3% trileucine, about 8%-9% citrate buffer and an active agent, more suitably about 39% trehalose, about 10.5% leucine, about 2% trileucine, about 8.5% citrate buffer and an active agent.

In additional embodiments, dry powder formulations are provided that consist essentially of about 30%-50% of an amorphous saccharide, leucine, about 1% to about 10% trileucine, about 1% to about 10% of a buffer, and an active agent, wherein the wherein the leucine and the trileucine are present at a concentration ratio of leucine:trileucine of about 0.1:1 to about 30:1. In additional embodiments, dry powder formulations are provided that consist essentially of about 30%-50% of an amorphous saccharide, about 8% to about 11% leucine, about 2% to about 4% trileucine, about 1% to about 10% of a buffer, and an active agent. Additional dry powder formulations are provided that consist essentially of about 35%-45% trehalose, about 9% to about 11% leucine, about 2% to about 3% trileucine, about 2% to about 85 citrate buffer, and an active agent. In further embodiments, the dry powder formulations consist essentially of about 39% trehalose, about 10.5% leucine, about 2% trileucine, about 8.5% citrate buffer, and an active agent.

In compositions and formulations that "consist essentially" of the recited ingredients, such compositions and formulations contain the recited components and those that do not materially affect the basic and novel characteristics of the claimed formulations. Components that do not materially affect the basic and novel characteristics of the claimed formulations are those that do not limit the ability of the leucine and trileucine to stabilize the dry powder formulations. Suitably, compositions and formulations that consist essentially of the recited ingredients specifically exclude other amino acids or tripeptide amino acids, but can include additional sugars, buffers, etc.

In exemplary embodiments, a dry powder formulation is provided that comprises about 30-50%, trehalose, about 10%-11% leucine, about 1%-3% trileucine, about 8%-9% citrate buffer and about 30-50% of anti-TSLP antibody fragment, more suitably about 39% trehalose, about 10.5% leucine, about 2% trileucine, about 8.5% citrate buffer and about 40% of anti-TSLP antibody fragment.

In further exemplary embodiments, a dry powder formulation is provided that consists essentially of about 30-50% trehalose, about 10%-11% leucine, about 1%-3% trileucine, about 8%-9% citrate buffer and about 30-50% of anti-TSLP antibody fragment, more suitably about 39% trehalose, about 10.5% leucine, about 2% trileucine, about 8.5% citrate buffer and about 40% of the active agent.

The microparticles that make up the dry powder formulations described herein suitably have a specified mass median aerodynamic diameter (MMAD) when provided in aerosol form. The microparticles may also have a specified equivalent optical volume mean diameter (oVMD). oVMD may also be referred to as particle size distribution (PSD or pPSD).

As used herein, "mass median aerodynamic diameter" or "MMAD" is a measure of the aerodynamic size of a dispersed microparticle. The aerodynamic diameter is used to describe an aerosolized powder in terms of its settling behavior and is the diameter of a unit density sphere having the same settling velocity, in air, as the microparticle. The aerodynamic diameter encompasses particle shape, density and physical size of a microparticle. As used herein, MMAD refers to the midpoint or median of the aerodynamic particle size distribution of an aerosolized powder determined by cascade impaction, unless otherwise indicated. Suitably the microparticles of the dry powder formulations provided herein have a mass median aerodynamic diameter (MMAD) of about 1 μm to about 10 μm, more suitably about 2 μm to about 8 μm, about 2 μm to about 7 μm, about 2 μm to about 6 μm, about 2 μm to about 5 μm, about 2 μm to about 4 μm, about 3 μm to about 7 μm, about 4 μm to about 7 μm, about 3 μm to about 6 μm, or about 2 μm, about 3 μm, about 4 μm, about 5 μm, about 6 μm, or about 7 μm.

Suitably, the fine particle fraction (the fraction of particles emitted from an inhalation device having an aerodynamic particle diameter of less than 5 μm of the dry powder formulations described herein is ≥50%, more suitably ≥60%. This fine particle fraction (FPF) may contribute to a low device retention of the dry powder formulations of less than 20%, suitably less than 15%, less than 10%, or less than 5%, remaining in a device following delivery to a patient.

In additional embodiments, the microparticles suitably have an equivalent optical volume mean diameter (oVMD) of about 0.5 μm to about 7 μm. Equivalent optical volume mean diameter (oVMD) refers the mean diameter of a sphere that best approximates a specific optical interaction of the microparticle with light, where half of the microparticles are best approximated by an equivalent sphere smaller, and half of the microparticles are best approximated by an equivalent sphere larger than the mean, when measured using a suitable optical technique. In exemplary embodiments, the microparticles have an equivalent optical volume mean diameter (oVMD) of about 0.5 μm to about 6 μm, or about 1 μm to about 5 μm, or about 1 μm to about 4 μm, or about 2 μm to about 4.5 μm, or about 2.5 μm to about 4 μm, or about 2 μm to about 4 μm, or about 2 μm to about 3 μm, or about 2 μm to about 3.5 μm, or about 1 μm, about 1.5 μm, about 2 μm, about 2.5 μm, about 3 μm, about 3.5 μm, about 4 μm, about 4.5 μm, or about 5 μm.

As described herein, a high compressed bulk density allows for the delivery of a larger amount of active agent, utilizing the same delivery volume. Certain biological agents may require delivery payloads of as much as 50 mg/dose, or higher, to effective treatment. As shown illustratively in FIG. 8B, the combination of leucine and trileucine can result in a dry powder formulation that has a higher bulk density, and therefore for the same amount of fill weight, takes up substantially less volume.

Exemplary platform formulations shown in FIG. 8B are provided below. LTC indicates a formulation with no Trileucine (TLeu), but containing leucine, trehalose and citrate buffer; TTC indicates a formulation with no Leucine (Leu), but containing trileucine, trehalose and citrate buffer; TLTC indicates the inclusion of both leucine and trileucine, as well as trehalose and citrate buffer. Cit refers to citrate buffer. Tre refers to trehalose.

TABLE 1

Exemplary Platform Formulations

| Platform | % Tre | % Leu | % TLeu | % Cit |
|---|---|---|---|---|
| LTC | 46 | 45 | 0 | 9 |
| TTC | 81 | 0 | 11.2 | 7.8 |
| TLTC | 79 | 10.5 | 2 | 8.5 |

Capsules (size 3 capsules) of each formulation are shown at the respective fill weights in FIG. 8B. As illustrated, for the TLTC formulation, the combination of trileucine and leucine allows for the filling of a capsule with 100 mg of dry powder formulation, while still maintaining some remaining space in the capsule. The other formulations could not be filled above about 70-80 mg fill weight. This represents the dramatic improvement provided by the use of leucine and trileucine in combination to prepare a formulation with a high compressed bulk density, allowing for a high fill weight.

As described herein, the use of leucine and trileucine in the dry powder formulations also results in microparticles having the desired sizes (MMAD), as well as desirable specific surface area (SSA) and roughness, resulting in microparticles that can flow appropriately and be delivered to the lungs using various inhalation platforms.

Specific surface area (SSA) of the microparticles is defined as the total surface area of the microparticles per unit of mass (suitably with units of $m^2/g$). Methods of measuring SSA are known in the art, and include for example Brunauer-Emmett-Teller (BET) measurements using specific surface area evaluation of materials by nitrogen adsorption measured as a function of relative pressure. The surface area is determined by calculating the amount of adsorbate gas corresponding to a monomolecular layer on the surface of the microparticles. The technique measures external area and any pore area evaluations to determine the total specific surface area. Instruments for measuring BET are known in the art.

In embodiments, the specific surface area (SSA) of the microparticles of the dry powder formulations is about 3 $m^2/g$ to about 8 $m^2/g$. In suitable embodiments, the SSA of the plurality of microparticles is about 3.5 $m^2/g$-7.5 $m^2/g$, or about 4 $m^2/g$-7 $m^2/g$, or about 4.5 m2/g-7 m2/g, or about 5 $m^2/g$-7 $m^2/g$, or about 4.5 $m^2/g$-6 $m^2/g$, or about 5 $m^2/g$-6 $m^2/g$, or about 4 $m^2/g$, about 4.5 $m^2/g$, about 5 $m^2/g$, about 5.5 $m^2/g$, about 6 $m^2/g$, about 6.5 $m^2/g$, or about 7 $m^2/g$.

Figure 9:
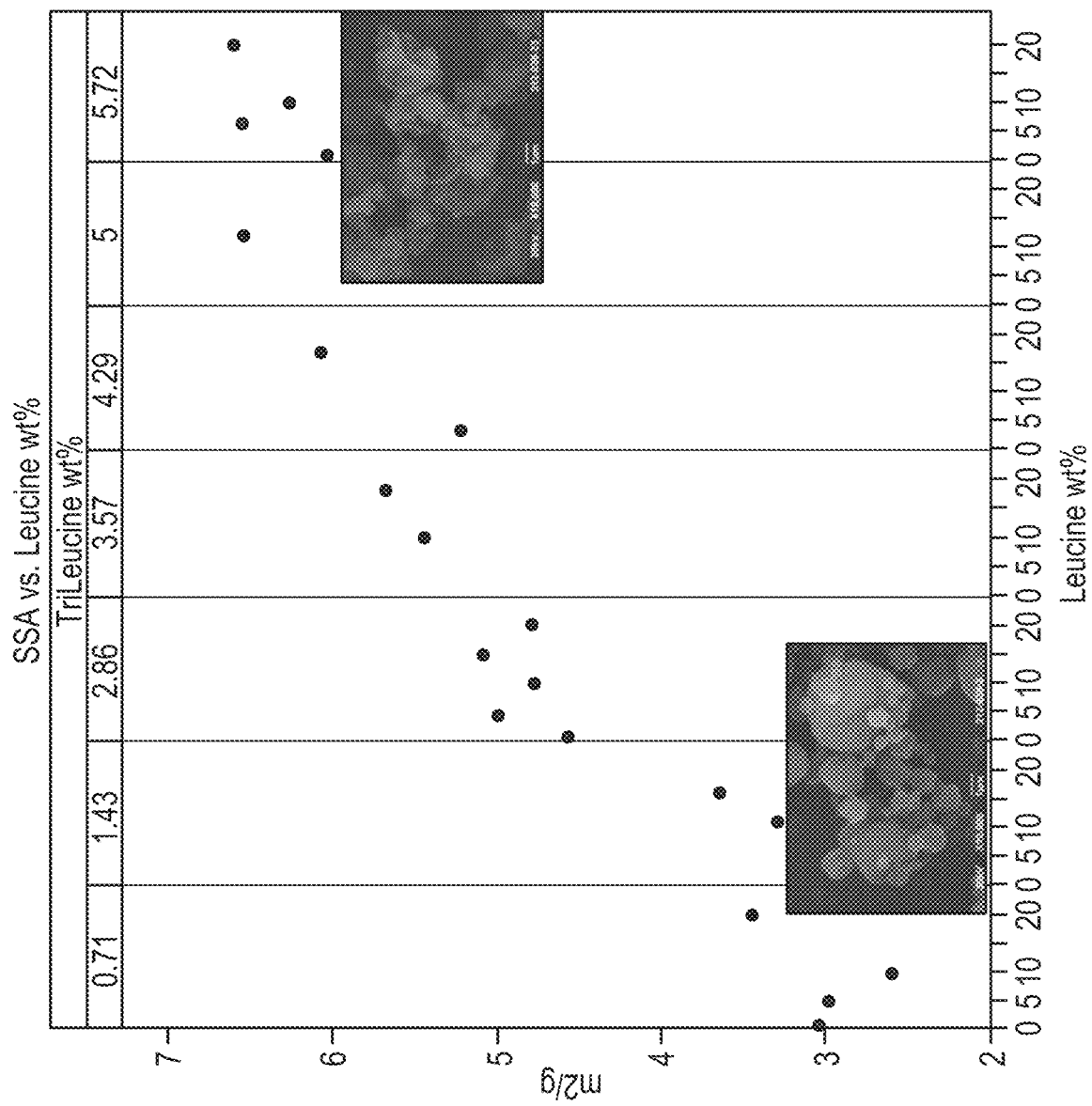
FIG. 9 shows the results of specific surface area measured using BET, in $m^2/g$, for microparticles of dry powder formulations in accordance with embodiments hereof.
Figure 10:
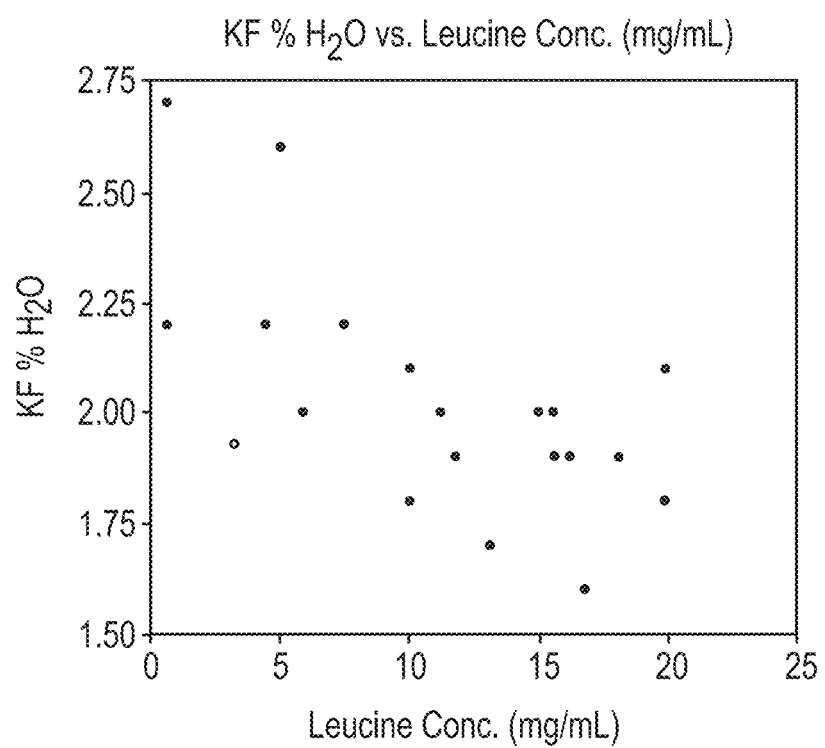
FIG. 10 shows the indirect correlation of moisture content with leucine concentration.

FIG. 9 shows the results of specific surface area measured using BET, in $m^2/g$. Each column within FIG. 9 represents a different amount of trileucine in the formulations. Within each column, the amount of leucine increases from about 1% to about 20%. Inset micrographs demonstrate the physical appearance of the microparticles at low SSA (bottom left) and higher SSA (top right). As shown, at lower wt % trileucine, SSA remains below approximately 5 $m^2/g$, but increases with increasing leucine. Above about 2% trileucine, the SSA increases to greater than 3.0 $m^2/g$, and also increases with increasing percent leucine. SSA values above 5.5 $m^2/g$, and approaching 7.0 $m^2/g$, are achieved with trileucine amounts above about 4%. A desirable range of specific surface area of about 4-7 $m^2/g$ can readily be achieved using between about 1-6% trileucine, and amounts of leucine between about 1-20%. As shown, by utilizing an amount of trileucine below about 6%, the amount of leucine can be kept below 10%, even below 5%, and still maintain a desirable SSA and microparticles with a surface roughness. The micrograph at the top left shows the shape of microparticles of the dry powder formulations described herein, exhibiting a desirable size, specific surface are, and surface roughness.

In certain embodiments, the dry powder formulation has a compressed bulk density of about 0.4-1.0 $g/cm^3$. Suitably, the compressed bulk density of the dry powder formulation is about 0.5-0.8 $g/cm^3$. In embodiments, the compressed bulk density of a dry powder formulation described herein is about 0.4-0.9 $gm/cm^3$, about 0.4-0.8 $gm/cm^3$, about 0.5-0.8 $gm/cm^3$, about 0.6-0.8 $gm/cm^3$, or about 0.4 $gm/cm^3$, about 0.5 $gm/cm^3$, about 0.6 $gm/cm^3$, about 0.7 $gm/cm^3$, or about 0.8 $gm/cm^3$. In certain embodiments, the compressed bulk density of a dry powder formulation described herein is from about 0.4 $gm/cm^3$ to about 0.9 $gm/cm^3$. In certain embodiments, the compressed bulk density of a dry powder formulation described herein is from about 0.5 $gm/cm^3$ to about 0.8 $gm/cm^3$.

The dry powder formulations suitably include a glass stabilization agent as described herein, including an amorphous saccharide or a buffer, or the use of both an amorphous saccharide and a buffer. Exemplary amorphous saccharides include those described herein, including trehalose, sucrose, raffinose, inulin, dextran and cyclodextrin. Suitably the amorphous saccharide is present at about 30% to about 70%, and in embodiments is trehalose, suitably present at about 35%-60, or 35%-55%.

Exemplary buffers for use in the dry powder formulations are described herein, and include a citrate buffer, a phosphate buffer and a tartrate buffer. Suitably the buffer is present at about 1% to about 10%, and in embodiments is a citrate buffer. In certain embodiments, the pH of the citrate buffer is from about pH 5.5 to about pH 6.5, such as about pH 5.5, about pH 5.6, about pH 5.7, about pH 5.8, about pH 5.9, about pH 6.0, about pH 6.1, about pH 6.2, about pH 6.3, about pH 6.4 or about pH 6.5. In certain embodiments, the pH of the citrate buffer is about pH 6.4.

In certain embodiments the dry powder formulations described herein comprise a surfactant. As defined herein, "surfactant" refers to a molecule or compound that reduces particle agglomeration, particle adhesion to the surface of a capsule, container walls or valve components of an inhalable delivery device. It has also been found that a surfactant reduces the formation of sub-visible particles (SVPs) upon reconstitution of the formulation. Removing or reducing the formation of SVPs simplifies the analytical characterization of the formulation, as it removes the burden of tracking the formation of SVPs during manufacturing. The analytical characterization of SVPs may involve the development of orthogonal techniques to identify and quantify SVPs for quality control purposes. Thus, removing SVPs or reducing them to acceptable levels removes the necessity of this characterization step from the manufacturing process, streamlining manufacturing. The removal of SVPs may also make dose ranging more predictable, since the kinetics of drug-release from SVPs is unknown. Furthermore, removing SVPs is likely to increase the amount of active agent available to engage in pharmacological activity post-reconstitution, which may mean not only that a higher delivered dose can be achieved, but a more accurate prediction of the delivered dose can be calculated. A higher delivered dose may also benefit the patient, for example, by potentially reducing the number or frequency of doses that must be delivered for extracting a pharmacological benefit.

A "sub-visible particle" ("SVP") is a particle not visible to the naked eye of from about 1 μm to about 200 μm. The presence of sub-visible particles can be determined by reconstituting a dry powder formulation and the liquid having a cloudy quality. The actual determination of the presence of SVPs can be confirmed using a technique like microflow imaging. Microflow imaging (or MFI), combines microfluidic flow microscopy and high resolution imaging particle analysis to quantify SVP counts. MFI can bin these counts across a particle size range, for example, by binning particles counts in a size range of about 1 to about 200 μm, about 2 μm to about 200 μm, about 5 μm to about 200 μm, about 10 μm to about 200 μm and about 25 μm to about 200 μm. The examples show that the inclusion of a surfactant in the dry powder formulation reduces the presence of SVPs in each particle size range in comparison to a control formulation in which no surfactant is present (e.g. FIG. 15A). Therefore, in certain embodiments, a dry powder formulation disclosed herein comprises a surfactant, wherein upon reconstitution, the number of sub-visible particles in the formulation are decreased. In some embodiments, the number of sub-visible particles are decreased in comparison to an equivalent formulation having no surfactant.

In certain embodiments, the number of SVPs of about 25 μm to about 200 μm in size are decreased to below 30,000 particles per ml, such as 25,000 particles per ml, 20,000 particles per ml, 15,000 particles per ml, 10,000 particles per ml or 5,000 particles per ml. In certain embodiments, the number of SVPs of about 25 μm to about 200 μm in size are decreased to below 1,000 particles per ml. In certain embodiments, the number of SVPs of about 25 μm to about 200 μm in size are decreased to below 1,000 particles per ml. In certain embodiments, the number of SVPs of about 25 μm to about 200 μm in size are decreased to below 100 particles per ml.

In certain embodiments, the number of SVPs of about 10 μm to about 200 μm in size are decreased to below 100,000 particles per ml, such as 90,000 particles per ml, 80,000 particles per ml, 70,000 particles per ml, 60,000 particles per ml, 50,000 particles per ml, 40,000 particles per ml or 30,000 particles per ml. In certain embodiments, the number of SVPs of about 10 μm to about 200 μm in size are decreased to below 10,000 particles per ml. In certain embodiments, the number of SVPs of about 10 μm to about 200 μm in size are decreased to below 1,000 particles per ml. In certain embodiments, the number of SVPs of about 10 μm to about 200 μm in size are decreased to below 100 particles per ml.

In certain embodiments, the number of SVPs of about 5 μm to about 200 μm in size are decreased to below 200,000 particles per ml, such as 180,000 particles per ml, 170,000 particles per ml, 160,000 particles per ml, 150,000 particles per ml or 140,000 particles per ml. In certain embodiments, the number of SVPs of about 5 μm to about 200 μm in size are decreased to below 50,000 particles per ml. In certain embodiments, the number of SVPs of about 5 μm to about 200 μm in size are decreased to below 10,000 particles per ml. In certain embodiments, the number of SVPs of about 5 µm to about 200 µm in size are decreased to below 2,000 particles per ml.

In certain embodiments, the number of SVPs of about 2 µm to about 200 µm in size are decreased to below $1 \times 10^6$ particles per ml, such as $0.8 \times 10^6$ particles per ml, $0.7 \times 10^6$ particles per ml, $0.6 \times 10^6$ particles per ml or $0.5 \times 10^6$ particles per ml. In certain embodiments, the number of SVPs of about 2 µm to about 200 µm in size are decreased to below 100,000 particles per ml. In certain embodiments, the number of SVPs of about 2 µm to about 200 µm in size are decreased to below 50,000 particles per ml. In certain embodiments, the number of SVPs of about 2 µm to about 200 µm in size are decreased to below 10,000 particles per ml.

In certain embodiments, the number of SVPs of about 1 µm to about 200 µm in size are decreased to below $2 \times 10^6$ particles per ml, such as $1.8 \times 10^6$ particles per ml, $1.7 \times 10^6$ particles per ml, $1.6 \times 10^6$ particles per ml or $1.5 \times 10^6$ particles per ml. In certain embodiments, the number of SVPs of about 1 µm to about 200 µm in size are decreased to below 200,000 particles per ml. In certain embodiments, the number of SVPs of about 1 µm to about 200 µm in size are decreased to below 150,000 particles per ml.

In certain embodiments, the number of SVPs of about 25 µm to about 200 µm in size are reduced more than 2-fold, such as more than 3-fold, more than 4-fold, more than 5-fold, more than 6-fold, more than 7-fold, more than 8-fold or more than 9-fold, upon reconstitution, compared to a reference control. In certain embodiments, the number of SVPs of about 25 µm to about 200 µm in size are reduced more than 10-fold upon reconstitution compared to the reference control.

In certain embodiments, the number of SVPs of about 10 µm to about 200 µm in size are reduced more than 2-fold, such as more than 3-fold, more than 4-fold, more than 5-fold, more than 6-fold, more than 7-fold, more than 8-fold or more than 9-fold, upon reconstitution, compared to a reference control. In certain embodiments, the number of SVPs of about 10 µm to about 200 µm in size are reduced more than 10-fold upon reconstitution compared to the reference control.

In certain embodiments, the number of SVPs of about 5 µm to about 200 µm in size are reduced more than 2-fold, such as more than 3-fold, more than 4-fold, more than 5-fold, more than 6-fold, more than 7-fold, more than 8-fold or more than 9-fold, upon reconstitution, compared to a reference control. In certain embodiments, the number of SVPs of about 5 µm to about 200 µm in size are reduced more than 10-fold upon reconstitution compared to the reference control.

In certain embodiments, the number of SVPs of about 2 µm to about 200 µm in size are reduced more than 2-fold, such as more than 3-fold, more than 4-fold, more than 5-fold, more than 6-fold, more than 7-fold, more than 8-fold or more than 9-fold, upon reconstitution, compared to a reference control. In certain embodiments, the number of SVPs of about 2 µm to about 200 µm in size are reduced more than 10-fold upon reconstitution compared to the reference control. In certain embodiments, the number of SVPs of about 2 µm to about 200 µm in size are reduced more than 100-fold upon reconstitution compared to the reference control.

In certain embodiments, the number of SVPs of about 1 µm to about 200 µm in size are reduced more than 2-fold, such as more than 3-fold, more than 4-fold, more than 5-fold, more than 6-fold, more than 7-fold, more than 8-fold or more than 9-fold, upon reconstitution, compared to a reference control. In certain embodiments, the number of SVPs of about 1 µm to about 200 µm in size are reduced more than 10-fold upon reconstitution compared to the reference control.

In certain embodiments the reference control is an equivalent formulation lacking a surfactant. In some embodiments, the formulation is reconstituted in water. In some embodiments, the formulation is reconstituted to an active agent concentration of 30 mg/ml. In some embodiments, the formulation is reconstituted to an active agent concentration of 2.5 mg/ml. In some embodiments, the number of SVPs are determined by microflow imaging (MFI). In certain embodiments, the number of SVPs are determined by microflow imaging (MFI) using a method as defined in the examples.

Exemplary surfactants suitable for use in the dry powder formulations described herein include, but are not limited to, polysorbate-20 (PS-20), polysorbate-40 (PS-40), polysorbate-60 (PS-60), polysorbate-80 (PS-80) and poloxamer-188. In certain embodiments, the formulations described herein comprise PS-80, suitably at a concentration in the range of from about 0.27% by weight to about 2.7% by weight, suitably from about 0.27% by weight to about 1.33% by weight, suitably from about 0.67% by weight to about 1.33% by weight. In certain embodiments, the formulation comprises PS-80 at a concentration in the range of from about 0.3% by weight to about 3% by weight. In certain embodiments, the formulation comprises PS-80 at a concentration in the range of from about 0.3% by weight to about 2.5% by weight. In certain embodiments, the formulation comprises PS-80 at a concentration in the range of from about 0.5% by weight to about 2.5% by weight. In certain embodiments, the formulation comprises PS-80 at a concentration in the range of from about 0.5% by weight to about 2% by weight. In certain embodiments, the formulation comprises PS-80 at a concentration in the range of from about 0.5% by weight to about 1.5% by weight.

In exemplary embodiments, the formulation comprises PS-80 at a concentration in the range of from about 0.67% to about 1.33%.

In exemplary embodiments, the formulation comprises PS-80 at a concentration of about 0.7% (w/w), about 0.8% (w/w), about 0.9% (w/w), about 1.0% (w/w), about 1.1% (w/w), about 1.2% (w/w), or about 1.3% (w/w). In some embodiments, the formulation comprises PS-80 at a concentration of about 1.1% (w/w).

In exemplary embodiments, the composition comprises PS-80 at a concentration of 0.7%±0.35 (w/w), about 0.8%±0.4 (w/w), about 0.9%±0.45 (w/w), about 1.0%±0.5 (w/w), about 1.1%±0.55 (w/w), about 1.2%±0.6 (w/w), about 1.3%±0.65 (w/w), about 1.4%±0.7 (w/w), about 1.5%±0.75 (w/w), about 1.6%±0.8 (w/w) or about 1.7%±0.75 (w/w). In some embodiments, the formulation comprises PS-80 at a concentration of 1.1%±0.55 (w/w).

In certain embodiments, the formulations described herein comprise poloxamer-188, suitably at a concentration in the range of from about 1% by weight to about 10% by weight. In exemplary embodiments, the formulation comprises poloxamer-188 (P188) at a concentration in the range of from about 0.67% to about 2.67%. In certain embodiments, the formulation comprises P188 at a concentration in the range of from about 0.3% by weight to about 3% by weight. In certain embodiments, the formulation comprises P188 at a concentration in the range of from about 0.3% by weight to about 2.5% by weight. In certain embodiments, the formulation comprises P188 at a concentration in the range of from about 0.5% by weight to about 2.5% by weight. In certain embodiments, the formulation comprises P188 at a concentration in the range of from about 0.5% by weight to about 2% by weight. In certain embodiments, the formulation comprises P188 at a concentration in the range of from about 0.5% by weight to about 1.5% by weight.

In exemplary embodiments, the formulation comprises P188 at a concentration in the range of from about 0.67% to about 1.67%.

In exemplary embodiments, the formulation comprises P188 at a concentration of about 0.7% (w/w), about 0.8% (w/w), about 0.9% (w/w), about 1.0% (w/w), about 1.1% (w/w), about 1.2% (w/w), about 1.3% (w/w), about 1.4% (w/w), about 1.5% (w/w), about 1.6% (w/w) or about 1.7% (w/w).

In exemplary embodiments, the dry powder formulation comprises about 39% trehalose, about 10.5% leucine, about 2% trileucine, about 8.5% citrate buffer and the active agent.

Suitable sizes for the microparticles of the dry powder formulations are described herein, and in embodiments, the plurality of microparticles have a mass median aerodynamic diameter (MMAD) of about 2 µm to about 4 µm when provided in an aerosol form. Suitable specific surface areas (SSA) of the microparticles are described herein, and include for example, a specific surface area of about 4-7 $m^2/g$. Suitably, the microparticles have an equivalent optical volume mean diameter (oVMD) of about 1 µm to about 5 µm.

In further embodiments, provided herein is a method of preparing a dry powder formulation. In embodiments, the method suitably comprises preparing a liquid feedstock, comprising leucine, about 0.1 mg/mL to about 6 mg/mL trileucine, the active agent, and suitably further comprising a glass stabilization agent. A glass stabilization agent as described herein can be omitted from the dry powder formulations if desired. The liquid feedstock may also comprise a surfactant. The liquid feedstock is prepared by combining these components in a liquid solvent, to create a feedstock in which each of the components is dissolved. Heating may be added as desired or required to increase the solubility of the various components to form the liquid feedstock. Exemplary liquid solvents include water, including deionized water, as well as dilute solutions of alcohols with water. In embodiments, the active agent is suitably added to the liquid feedstock after the addition and dissolution of the remaining components of the feedstock.

In suitable embodiments of the methods of preparation, the leucine and the trileucine are present at a concentration ratio of leucine:trileucine of about 0.1:1 to about 30:1 in the liquid feedstock. As described herein, when preparing a liquid feedstock, the leucine and trileucine are provided as mg/mL amounts. Thus, in such embodiments, the concentration ratio of leucine:trileucine of about 0.1:1 to about 30:1 in the set volume of the liquid feedstock corresponds to the ratio of leucine:trileucine by weight in the liquid feedstock. In further embodiments, the leucine and the trileucine are present at a concentration ratio of leucine:trileucine of about 0.1:1 to about 25:1, about 0.5:1 to about 20:1, about 1:1 to about 20:1, about 1:1 to about 15:1, about 1:1 to about 12:1, about 1:1 to about 10:1, about 1:1 to about 7:1, about 1:1 to about 6:1, or about 1:1 to about 2:1, about 3:1, about 4:1, about 5:1, about 5:1:1, about 5.2:1 about 5.25:1, about 5.3:1, about 5.4:1, about 5.5:1, about 5.75:1 or about 6:1, in the liquid feedstock.

The liquid feedstock may then be atomized. In certain embodiments, the liquid feedstock is filtered prior to atomizing. In certain embodiments, the liquid feedstock is filtered through a 0.22 micron filter. In certain embodiments, the liquid feedstock comprising leucine and trileucine is filtered prior to the addition of the active agent. In certain embodiments, the liquid feedstock is filtered after the addition of the active agent prior to atomizing. Atomizing refers to converting the liquid feedstock to fine droplets, suitably using a pressurized gas (such as $CO_2$, or an inert gas). Exemplary devices for producing an atomized liquid feedstock are known in the art and include the use of various atomizing nozzles have desired sizes and flow characteristics. Exemplary parameters for the atomizing including an outlet temperature of about 50° C.-90° C., suitably about 60° C.-80° C., or about 70° C.; a feedstock feed rate of about 8-15 ml/min, suitably about 9-14 ml/min, about 10-13 ml/min, or about 12 ml/min; an atomizer gas flow rate of about 9-15 kg/hour (hr. or h), suitably about 10-14 kg/hr, about 12-14 kg/hr, or about 13 kg/hr; and drying gas flow rate of about 60-100 kg/hr, suitably about 60-90 kg/hr, about 70-90 kg/hr, or about 80 kg/hr.

The atomized liquid feedstock may then be dried, suitably under heat and in combination with flowing air to aid in the drying. The result of the drying yields a plurality of microparticles. Drying temperatures typically range from about 50°-100° C., or about 60°-100° C., or about 70°-90° C.; air flow rate can be on the order of about 10-40 $m^3$/hour.

Exemplary glass stabilization agents, including amorphous saccharides and buffers are described herein, as are suitable amounts of the glass stabilization agents. Suitable amounts of leucine and trileucine are provided throughout as well. As the final, dry powder formulation should contain the recited amounts of leucine and trileucine (and other components), such amounts are also used in the liquid feedstock. The result of the drying process following atomization is that any liquid solvent is removed, and thus the full amount of the original dry weight of the components corresponds to the final dry weight of the compounds in the dry powder formulation. Exemplary active agents are also described herein.

The methods of preparing dry powder formulations described herein suitably provide microparticles having the desired physical characteristics noted, including the desired compressed bulk density, specific surface area and sizes. Exemplary sizes are described herein, as are exemplary SSAs, including a specific surface area of less than about 10 $m^2/g$, suitably about 4-7 $m^2/g$. Suitably the methods provide a plurality of microparticles having an equivalent optical volume mean diameter (oVMD) of about 1 µm to about 5 µm, as described herein; a mass median aerodynamic diameter (MMAD) of about 2 µm to about 4 µm when provided in an aerosol form; a compressed bulk density of about 0.4 $g/cm^3$-0.8 $g/cm^3$.

An advantage of the methods of preparing dry powder formulations described herein relates to the high throughput nature of the process. For example, if a flow rate of atomization is set at 20 ml/min, the following throughput in grams/hour, was determined.

TABLE 2

Concentration Implications on Throughput
Concentration Implications on Throughput

| Leucine Content | TriLeucine Content | Max Solids Loading (mg/mL) (Max Solubility limited) | Throughput (g/hr) (at 20 ml/min process liq. flow rate) |
|---|---|---|---|
|  | 20.0% | 25 | 30 |
| 60.0% |  | 33 | 40 |

TABLE 2-continued

Concentration Implications on Throughput
Concentration Implications on Throughput

| Leucine Content | TriLeucine Content | Max Solids Loading (mg/mL) (Max Solubility limited) | Throughput (g/hr) (at 20 ml/min process liq. flow rate) |
|---|---|---|---|
| 45.0% |  | 44 | 53 |
|  | 10.0% | 50 | 60 |
| 30.0% |  | 67 | 80 |
| 10.5% | 2.0% | 190 | 229 |
| 10.0% | 2.5% | 200 | 240 |
| 8.0% | 2.0% | 250 | 300 |

As set forth, using only trileucine in a feedstock, with a maximum trileucine concentration of 5 mg/mL, a max solids loading of 25 mg/mL was reached (related to the maximum solubility). This results in a throughout of 30 g/hour. With only leucine at 60%, with a maximum leucine concentration of 20 mg/mL a max solids loading of 33 mg/mL was reached, and a throughput of 40 g/hour. Additional results for the use of only leucine and trileucine are also shown. In contrast, for the three feedstocks examined that contained both leucine and trileucine, a maximum solids loading of 250 mg/mL and a throughput of 300 g/hour was reached using only 8% leucine and 2% trileucine. This was a surprising and unexpected finding of the advantages of the methods and formulations disclosed herein, in that a dispersible particle can be provided using relatively small amounts of leucine and trileucine, but also allowing for a large amount of throughput. Such high throughput greatly impacts the ability to scale up production of the dry powder formulations described herein where large amounts of the formulations are required.

The methods and formulations described herein allow for the production of capsules, blister packs, etc., and other suitable containers for dry powder formulations. Such containers can be produced with 10-200 mg of dry powder, suitably 10-100 mg, or 25-75 mg or 50 mg or dry powder formulation. Such containers can suitably deliver 0.1-10 mg of a dry powder formulation to a patient's lungs.

In some embodiments, the use of the methods described herein provide dry powder formulations that can reduce the total number of capsules required for use in an inhalation device. For example, the volume required to deliver 50-100 mg of active agent can be reduced from two larger 00 capsules to a single size 3 capsule.

The methods described herein also provide a mechanism for increasing a compressed bulk density and a specific surface area of a dry powder formulation that comprises a plurality of microparticles. As described throughout, by incorporating leucine and trileucine into the dry powder formulation, a compressed bulk density of about 0.4-1.0 g/cm$^3$ (suitably about 0.5-0.8 g/cm$^3$), can readily be achieved. In addition, a specific surface area of about 5-10 m$^2$/g (suitably about 5 m$^2$/g to about 7 m$^2$/g), can also be achieved. In additional embodiments, the sizes of the microparticles can be formed in the ranges described herein, including microparticles with a mass median aerodynamic diameter (MMAD) of about 2 μm to about 4 μm when provided in an aerosol form.

Methods for producing an aerosol form of a dry powder formulation are known in the art and include for example, the use of inhaler devices such as a dry-powder inhaler (DPI) (e.g., a Monodose RS01 DPI by PLASTIAPE (Osnago, Italy)). The dry powder formulations described herein can be dispensed into a gas stream by either a passive or an active inhalation device, and remain suspended in the gas for an amount of time sufficient for at least a portion of the microparticles to be inhaled by the patient, so that a portion of the microparticles reaches the lungs.

Also provided herein are methods of treating a medical condition in a mammalian patient, which include administering to the patient by inhalation (including by dry-powder inhaler) the dry powder formulations as described herein.

Medical conditions that can be treated using the methods described herein include those that effect the nervous system, the endocrine system, the muscular system, the cardiovascular system, the digestive system, the respiratory system (and specifically the lungs), hormone systems, the immune system, the reproductive system, etc.

In embodiments, provided herein is a method of treating a TSLP-related inflammatory condition in a patient. TSLP-related inflammatory conditions may be triggered by allergic reactions or environmental irritants or stimulants. In some embodiments, the TSLP-related inflammatory condition may be asthma, chronic obstructive pulmonary disease, allergic rhinitis, allergic rhinosinusitis, allergic conjunctivitis, atopic dermatitis or eosinophilic esophagitis.

In some embodiments, the TSLP-related inflammatory condition is asthma, and the method of treatment said comprises administering via inhalation a dry powder formulation comprising a therapeutically effective amount of an anti-TSLP antibody or antibody fragment variant, to the patient. In certain embodiments, the patient is an adult. In certain embodiments, the patient is a child or adolescent.

As described herein, suitably the dry powder formulation includes a plurality of microparticles, the microparticles comprising: leucine; about 1% to about 10% trileucine by weight; and the anti-thymic stromal lymphopoietin (anti-TSLP) antibody or antibody variant, wherein the leucine and the trileucine are present at a concentration ratio of leucine:trileucine of about 0.1:1 to about 30:1. The dry powder formulation may comprise a compressed bulk density of about 0.3-1.0 g/cm$^3$. Exemplary components for inclusion in the formulation and amounts thereof are described throughout.

As described herein, the ability to deliver the anti-thymic stromal lymphopoietin (anti-TSLP) antibody or antibody variant via inhalation provides a delivery mechanism more amenable to use in a primary care setting.

In embodiments of the methods of treating asthma, the dry powder formulation is administered frequently and at lower dosages than a systemically administered anti-TSLP medicine. In some embodiments, the formulation may be administered daily. Such embodiments may be more convenient for the subject or patient. Furthermore, such embodiments may reduce side effects that can occur via systemic administration.

Suitably, the antigen binding fragment of the antibody for use in the methods of treatment comprises
a heavy chain variable domain comprising:
  a heavy chain CDR1 sequence comprising the amino acid sequence set forth in SEQ ID NO:1;
  a heavy chain CDR2 sequence comprising the amino acid sequence set forth in SEQ ID NO:2;
  a heavy chain CDR3 sequence comprising the amino acid sequence set forth in SEQ ID NO:3; and
a light chain variable domain comprising:
  a light chain CDR1 sequence comprising the amino acid sequence set forth in SEQ ID NO:5;
  a light chain CDR2 sequence comprising the amino acid sequence set forth in SEQ ID NO:6, and a light chain CDR3 sequence comprising the amino acid sequence set forth in SEQ ID NO:7.

In additional embodiments of the methods of treatment, the antigen binding fragment comprises a heavy chain variable domain comprising SEQ ID NO:4; and a light chain variable domain comprising SEQ ID NO: 8.

In some embodiments, forms of asthma amenable to treatment with the formulation of the invention include mild asthma, moderate asthma, severe asthma, no eosinophilic asthma, low eosinophilic asthma and high eosinophilic asthma. In certain embodiments, the formulations of the invention may be for use in the treatment of mild asthma. In certain embodiments, the formulations of the invention may be for use in the treatment of moderate asthma. In certain embodiments, the formulations of the invention may be for use in the treatment of severe asthma. In certain embodiments, the formulations of the invention may be for use in the treatment of no eosinophilic asthma. In certain embodiments, the formulations of the invention may be for use in the treatment of low eosinophilic asthma. In certain embodiments, the formulations of the invention may be for use in the treatment of high eosinophilic asthma.

The terms "mild asthma" and "moderate asthma" as used herein refer to asthma that has a Global Initiative for Asthma (GINA) scale of 3 or less, suitably a GINA scale of 2 or 3. The GINA scale measures the severity of asthma, based on the following criteria (see "Pocket Guide for Asthma Management and Prevention," Global Initiative for Asthma; 2019).

The term "severe asthma" as used herein refers to asthma that requires high intensity treatment (e.g., GINA Step 4 and Step 5) to maintain good control, or where good control is not achieved despite high intensity treatment (GINA, Global Strategy for Asthma Management and Prevention. Global Initiative for Asthma (GINA) December 2012). The term "severe asthma" also encompasses moderate-severe asthma. Moderate-severe asthmatics suitable for treatment with the formulations described herein may be those uncontrolled on medium dose to high dose ICS:LABA with one or more exacerbations and frequent symptoms. In certain embodiments, severe asthma is further defined as severe asthma with type 2 inflammation characterized by raised blood eosinophils (i.e. a blood eosinophil count of ≥150 cells/4) and/or raised FeNO. (i.e. FeNO≥20 ppb).

The term "FENO" refers to fractional exhaled nitric oxide, which is a biomarker for bronchial or airway inflammation. FENO is produced by airway epithelial cells in response to inflammatory cytokines, such as TSLP, IL-4 and IL-13. FENO levels in healthy adults range from 2 to 30 parts per billion (ppb). An exemplary assay for measuring FENO comprises subjects inhaling to total lung capacity through the NIOX MINO® Airway Inflammation Monitor and then exhaling for 10 seconds at 50 ml/sec (assisted by visual and auditory cues).

The term "high eosinophilic asthma" as used herein refers to an asthma patient having a screening blood eosinophil count of ≥250 cells/4.

Particularly, the formulations provide for the possibility of treating patients with less severe asthma who would normally be managed in a primary care setting. For example, patients with a Global Initiative for Asthma (GINA) scale of 3 or less, suitably a GINA scale of 2 or 3. The GINA scale measures the severity of asthma, based on the following criteria (see ("Pocket Guide for Asthma Management and Prevention," Global Initiative for Asthma; 2019).

daytime asthma symptoms more than twice per week;
night waking due to asthma;
use of an asthma reliever more than twice/week; and
activity limitation due to asthma. A score of zero of these criteria is considered "well controlled." A score of 1-2 of these criteria is considered "partially controlled." A score of 3-4 of these criteria is considered "uncontrolled."

In some embodiments, the formulations provide for the possibility of treating patients with moderate-severe asthma who could be managed in a primary care setting, or for treating patients with moderate-severe asthma with poor access to treatment via specialist care. For example, the formulations may be useful for the treatment of moderate-severe asthma patients with a Global Initiative for Asthma (GINA) scale of 4-5. Suitably, the formulations provide for the possibility of treating moderate-severe asthma that is uncontrolled. Suitably, the formulations provide for the possibility of treating moderate-severe asthma that is uncontrolled on medium dose to high dose ICS:LABA with one or more exacerbations and frequent symptoms.

Additional Exemplary Embodiments

Embodiment 1 is a dry powder formulation comprising a plurality of microparticles, the microparticles comprising: leucine, about 1% to about 10% trileucine by weight and an antigen binding fragment of an anti-thymic stromal lymphopoietin (TSLP) antibody comprising: a. a heavy chain variable domain comprising a heavy chain CDR1 sequence comprising the amino acid sequence set forth in SEQ ID NO:1, a heavy chain CDR2 sequence comprising the amino acid sequence set forth in SEQ ID NO:2; and a heavy chain CDR3 sequence comprising the amino acid sequence set forth in SEQ ID NO:3, wherein either of heavy chain CDR1, 2 or 3 optionally comprises a single amino acid substitution, and b. a heavy chain variable domain comprising a light chain CDR1 sequence comprising the amino acid sequence set forth in SEQ ID NO:5, a light chain CDR2 sequence comprising the amino acid sequence set forth in SEQ ID NO:6, and a light chain CDR3 sequence comprising the amino acid sequence set forth in SEQ ID NO:7, wherein either of light chain CDR 1, 2 or 3 optionally comprises a single amino acid substitution, wherein the leucine and the trileucine are present at a concentration ratio of leucine: trileucine of about 0.1:1 to about 30:1.

Embodiment 2 is a dry powder formulation of embodiment 1, wherein the dry powder formulation has a compressed bulk density of about 0.4-1.0 g/cm3.

Embodiment 3 is a dry powder formulation of any preceding embodiment, further comprising a glass stabilization agent.

Embodiment 4 is a dry powder formulation of embodiment 3, wherein the glass stabilization agent is an amorphous saccharide or a buffer.

Embodiment 5 is a dry powder formulation of embodiment 3, wherein the glass stabilization agent comprises an amorphous saccharide and a buffer.

Embodiment 6 is a dry powder formulation of embodiment 4 or embodiment 5, wherein the amorphous saccharide is selected from the group consisting of trehalose, sucrose, raffinose, inulin, dextran, mannitol, and cyclodextrin.

Embodiment 7 is a dry powder formulation of any one of embodiments 4-6, wherein the buffer is selected from the group consisting of a citrate buffer, a phosphate buffer, a histidine buffer, a glycine buffer, an acetate buffer and a tartrate buffer.

Embodiment 8 is a dry powder formulation of any one of embodiments 4-7, wherein the amorphous saccharide is present at about 30% to about 70% by weight.

Embodiment 9 is a dry powder formulation of any one of embodiments 4-8, wherein the amorphous saccharide is trehalose.

Embodiment 10 is a dry powder formulation of embodiment 9, wherein the trehalose is present at about 30%-65% by weight.

Embodiment 11 is a dry powder formulation of any one of embodiments 4-10, wherein the buffer is present at about 1% to about 10% by weight.

Embodiment 12 is a dry powder formulation of any one of embodiments 1-11, wherein the concentration ratio of leucine:trileucine is from about 1:1 to about 12:1.

Embodiment 13 is a dry powder formulation of any one of embodiments 1-12, wherein the concentration ratio of leucine:trileucine is from about 1:1 to about 7:1.

Embodiment 14 is a dry powder formulation of any one of embodiments 1-13, wherein the concentration ratio of leucine:trileucine is about 5.25:1.

Embodiment 15 is a dry powder formulation of any one of embodiments 1-14, comprising about 1% to about 7% trileucine by weight.

Embodiment 16 is a dry powder formulation of any one of embodiments 1-15, comprising about 8% to about 11% leucine by weight and about 2% to about 4% trileucine by weight.

Embodiment 17 is a dry powder formulation of any one of embodiments 1-16, comprising about 10.5% leucine by weight and about 2% trileucine by weight.

Embodiment 18 is a dry powder formulation of any one of embodiments 1-17, further comprising a surfactant, wherein the surfactant is optionally selected from polysorbate-20 (PS-20), polysorbate-40 (PS-40), polysorbate-60 (PS-60), polysorbate-80 (PS-80) and poloxamer-188.

Embodiment 19 is a dry powder formulation of embodiment 18, wherein the surfactant is PS-80, wherein optionally PS-80 is present at a concentration in the range of from about 0.27% by weight to about 2.7% by weight.

Embodiment 20 is a dry powder formulation of embodiment 18, wherein the surfactant is poloxamer-188, wherein optionally poloxamer-188 is present at a concentration in the range of from about 1% by weight to about 10% by weight.

Embodiment 21 is a dry powder formulation of any one of embodiments 1-20, wherein the plurality of microparticles have an equivalent optical volume mean diameter (oVMD) of about 1 μm to about 5 μm.

Embodiment 22 is a dry powder formulation of any one of embodiments 1-21 wherein the plurality of microparticles have a mass median aerodynamic diameter (MMAD) of about 2 μm to about 4 μm when provided in an aerosol form.

Embodiment 23 is a dry powder formulation of any one of embodiments 2-22, wherein the compressed bulk density is about 0.5 g/cm3 to about 0.8 g/cm3.

Embodiment 24 is a dry powder formulation of any of embodiments 2-23, comprising about 39% trehalose, about 10.5% leucine, about 2% trileucine and about 8.5% citrate buffer.

Embodiment 25 is a dry powder formulation of any of embodiments 1-24, wherein the plurality of microparticles have a specific surface area of less than about 10 m2/g.

Embodiment 26 is a dry powder formulation of embodiment 25, wherein the plurality of microparticles have a specific surface area of from about 4 mg2/g to about 7 m2/g.

Embodiment 27 is a dry powder formulation of any preceding embodiment, wherein the heavy chain variable domain CDR1 comprises the amino acid sequence set forth in SEQ ID NO:1, the heavy chain variable domain CDR2 comprises the amino acid sequence set forth in SEQ ID NO:2, the heavy chain variable domain CDR3 comprises the amino acid sequence set forth in SEQ ID NO:3, the light chain variable domain CDR1 comprises the amino acid sequence set forth in SEQ ID NO:5, the light chain variable domain CDR2 comprises the amino acid sequence set forth in SEQ ID NO:6 and the light chain variable domain CDR3 comprises the amino acid sequence set forth in SEQ ID NO:7.

Embodiment 28 is a dry powder formulation of embodiment 27, wherein the antigen binding fragment comprises a heavy chain variable domain comprising SEQ ID NO:4 and a light chain variable domain comprising SEQ ID NO: 8.

Embodiment 29 is a dry powder formulation of any preceding embodiment, wherein the antigen binding fragment is selected from Fab, Fab', F(ab')2, scFv, minibody, or diabody.

Embodiment 30 is a dry powder formulation of embodiment 29 wherein the antigen binding fragment is a Fab.

Embodiment 31 is a dry powder formulation of embodiment 30, wherein the Fab is human or humanized.

Embodiment 32 is a dry powder formulation of any preceding embodiment, wherein the anti-TSLP antibody from which the antigen binding fragment is derived is an IgG1.

Embodiment 33 is a method of treating asthma in a patient, comprising administering via inhalation the dry powder formulation according to any of embodiments 1-29.

Embodiment 34 is a method of embodiment 33, wherein the asthma is mild asthma.

Embodiment 35 is a method of embodiment 33, wherein the asthma is moderate asthma.

Embodiment 36 is a method of embodiment 33, wherein the asthma is severe asthma.

Embodiment 37 is a method of embodiment 33, wherein the asthma is eosinophilic or non-eosinophilic asthma.

Embodiment 38 is a method of embodiment 33, wherein the asthma is low eosinophilic asthma.

Embodiment 39 is a method of any one of embodiments 33-38, wherein the asthma is characterized by less than three of: daytime asthma symptoms more than twice per week; night waking due to asthma; use of an asthma reliever more than twice/week; and activity limitation due to asthma.

Embodiment 40 is a dry powder formulation according to any one of embodiments 1-32, for use in a method of treatment, wherein the formulation is to be administered by inhalation.

Embodiment 41 is a dry powder formulation for use according to embodiment 37, in a method of treating asthma.

Embodiment 42 is a dry powder formulation for use according to embodiment 38, wherein the asthma is mild asthma.

Embodiment 43 is a dry powder formulation for use according to embodiment 38, wherein the asthma is moderate asthma.

Embodiment 44 is a dry powder formulation for use according to embodiment 38, wherein the asthma is severe asthma.

Embodiment 45 is a dry powder formulation for use according to embodiment 38, wherein the asthma is eosinophilic asthma or non-eosinophilic asthma.

Embodiment 46 is a dry powder formulation for use according to embodiment 38, wherein the asthma is low eosinophilic asthma.

Embodiment 47 is a dry powder formulation for use according to embodiment 38, wherein the asthma is characterized by less than three of: daytime asthma symptoms more than twice per week; night waking due to asthma; use of an asthma reliever more than twice/week; and activity limitation due to asthma.

EXAMPLES

Example 1—Generation of Anti-TSLP FABS

A series of antibody binding fragments (Fab) derived from the anti-TSLP monoclonal antibody "A5" disclosed in WO 2009/035577, which is hereby incorporated by reference in its entirety, were generated using standard molecular biology and cloning techniques. In short, the CDR sequences of A5 were cloned into an IgG1 Fab scaffold, resulting in the Fab fragment herein referred to as Fab$_1$ or Fab$_1$. The VH and VL sequences of Fab$_1$ are disclosed as SEQ ID NOs:4 and 8, respectively.

Variants Fab$_{2-9}$ were also generated from Fab$_1$ comprising mutations in CDR regions. The combination of VH and VL CDRs for each of Fabs1-9 are shown in Table 3.

TABLE 3

CDR sequence of anti-TSLP Fabs$_{1-9}$

| | VH CDRs 1, 2 and 3 | VL CDRs 1, 2 and 3 |
|---|---|---|
| Fab$_1$ | SEQ ID NOs: 1, 2 and 3 | SEQ ID NOs: 5, 6 and 7 |
| Fab$_2$ | SEQ ID NOs: 1, 2 and 3 | SEQ ID NO: 11, 6 and 7 |
| Fab$_3$ | SEQ ID NOs: 1, 2 and 3 | SEQ ID NO: 14, 6 and 7 |
| Fab$_4$ | SEQ ID NO: 1, 15 and 3 | SEQ ID NOs: 5, 6 and 7 |
| Fab$_5$ | SEQ ID NOs: 1, 17 and 3 | SEQ ID NOs: 5, 6 and 7 |
| Fab$_6$ | SEQ ID NOs: 1, 2 and 3 | SEQ ID NOs: 19, 6 and 7 |
| Fab$_7$ | SEQ ID NOs: 1, 2 and 3 | SEQ ID NOs: 19, 6 and 7 |
| Fab$_8$ | SEQ ID NOs: 1, 2 and 3 | SEQ ID NOs: 5, 6 and 23 |
| Fab$_9$ | SEQ ID NOs: 1, 2 and 3 | SEQ ID NOs: 5, 6 and 25 |

The purity, stability and aggregation propensity of Fab$_1$ was analyzed. In brief, 50 mg/mL Fab$_1$ was formulated in 30 mM Sodium citrate, 105 mM trehalose, pH 6.0. Samples were placed in stability chambers at 40° C. and 5° C. for different periods of time. At different time points, samples were tested by relevant analytical techniques, such as high-performance size exclusion chromatography (HP-SEC). An Agilent HPLC system with temperature controlled autosampler, DAD or VWD, and Agilent ChemStation software/OpenLAB ECM CDS from Agilent Technologies (Santa Clara, CA, USA) was used. A guard column, TSKGEL® column (7.9 mm ID, Catalog no. 08543) and TSKGEL® G3000SWxl column (5 µm, 250 Å, and 7.8×300 mm, Catalog no. 08541) from Tosoh Bioscience (Griesheim, Germany) were also used. The mobile phase used was 0.1 M Sodium Phosphate Dibasic Anhydrous, 0.1 M Sodium Sulfate, pH 6.8. The results of the stability and aggregation analysis are shown in Table 4.

TABLE 4

Stability and aggregation of Fab$_1$

| | 5° C. | | | 40° C. | | |
|---|---|---|---|---|---|---|
| Months | % Monomer | % Aggregate | % Fragment | % Monomer | % Aggregate | % Fragment |
| 0.0 | 99.57 | 0.43 | 0.00 | 99.57 | 0.43 | 0.00 |
| 0.2 | | | | 99.56 | 0.44 | 0.00 |
| 0.5 | 99.51 | 0.49 | 0.00 | 99.31 | 0.55 | 0.14 |
| 0.7 | | | | 99.25 | 0.61 | 0.14 |
| 1 | 99.48 | 0.52 | 0.00 | 99.13 | 0.65 | 0.21 |
| 2 | 99.49 | 0.51 | 0.00 | | | |
| 3 | 99.47 | 0.53 | 0.00 | | | |
| Rate (m$^{-1}$) | −0.03 | 0.03 | 0.00 | −0.51 | 0.27 | 0.25 |
| RSQ | 0.6504 | 0.6504 | N/A | 0.9296 | 0.9447 | 0.8943 |

Stability of Fab$_1$ was also tested by differential scanning calorimetry (DSC). A MicroCal Capillary VP DSC from Malvern Panalytical (Malvern, UK) was used for the testing and an Origin 7.0 software (Northampton, MA, USA) was used for data analysis. The Fab$_1$ sample was diluted to 5 mg/mL with the formulation buffer (30 mM Sodium citrate, 105 mM trehalose, pH 6.0). For each individual run, 500 µL of diluted Fab$_1$ sample and reference (formulation buffer) were injected into the DSC sample and reference cells by the autosampler. The solutions were heated from 25° C. to 100° C. at a scanning rate of 95° C./hour. A scan of buffer (filled in both sample and reference cells) was also obtained as a blank for baseline correction of the sample.

The charge profile of Fab$_1$ was also determined by imaging isoelectric focusing (IEF) using an iCE3 analyser. The iCE3 capillary IEF analyser, PrinCE MicroInjector autosampler, MicroInjection coated transfer capillary were all purchased and supplied by Protein Simple. Samples were analysed using FC Cartridge with fluorocarbon-coated capillary and built-in electrolyte tanks (Part #101701, Protein Simple). The autosampler was maintained at 4° C. throughout the analysis. The pI range of Fab1 was determined to be from 8.35 to 8.80.

Example 2—FAB$_1$ Binds to HU and CYNO TSLP with Pm Affinity

Affinity of Fab$_1$ binding to TSLP determined by BIACORE™

The specificity and affinity of Fab$_1$ for recombinant mammalian cell-expressed human and cyno TSLP were determined using a BIACORE™ 8K SPR instrument (GE Healthcare, Little Chalfont, Bucks, UK).

S Series C1 biosensor chips, amine coupling kits, hepes buffered saline-based buffers and regeneration buffers were obtained from GE Healthcare and used according to the manufacturer's instructions. Streptavidin surfaces were prepared using lyophilized streptavidin that was reconstituted with D-PBS. Briefly, streptavidin was diluted to 4 µg mL-1 in 10 mM sodium acetate pH 4.5 and covalently immobilized to three flow cell surfaces of a S Series C1 biosensor chip by standard amine coupling methods. A final streptavidin surface of 170 response units (RUs) was achieved. The amine coupling reagents were also used to prepare a control blank surface, with no immobilized streptavidin, to serve as a reference surface within each flow cell. N-terminally tagged biotinylated TSLP (human and cyno) were then titrated onto each streptavidin surface to enable <100 RUs of Fab1 binding at saturation (Rmax). The low level of analyte binding ensured that mass-transport induced artefacts were minimized, especially when combined with the relatively fast, 50 µL min-1 assay flow-rates used during the kinetics measurement steps. Dilutions (Multi-Cycle Kinetics) of monomerized $Fab_1$ (2-fold dilutions in HBS-EP+ buffer ranging between 1.25 and 20 nM) were injected, at a 50 μL min-1 assay flowrate, for 2 minutes of association and 10 minutes dissociation. Multiple buffer-only injections were made under the same conditions throughout the experiment to allow for double reference processing of the final sensorgram sets.

The chip surface was fully regenerated by flowing two 30 second pulses of 10 mM glycine pH 1.7. Binding affinity and kinetics were determined using 1:1 Langmuir model.

The results shown in Table 5 demonstrate that $Fab_1$ binds to immobilized hu and cyno TSLP with similar affinities (within 2-fold; 46 pM and 88 pM, respectively).

TABLE 5

Affinity of $Fab_1$ for Human and Cynomolgus TSLP using BIAcore

| Analyte | $k_a$ ($M^{-1}s^{-1}$) | $k_d$ ($s^{-1}$) | $K_D$ (pM) |
|---|---|---|---|
| Human TSLP | 2.39E6 | 1.11E-4 | 46.3 |
| cyno TSLP | 1.75E6 | 1.55E-4 | 88.4 |

Binding Affinity Determined by Kinetic Exclusion Assay (KinExA).

The solution phase binding affinity ($K_D$) of $Fab_1$ for human and cyno TSLP was also determined using a KinExA 3200 instrument (Sapidyne Instruments, Boise, Idaho, USA) and the resulting data was processed using the KinExA Pro software version 4.1.11. The KinExA methodology has been reviewed (Darling and Brault, 2004).

$Fab_1$ was pre-mixed with varying concentrations of each of hu and cyno TSLP until equilibrium was reached (at least 12 concentrations of each hu and cyno TSLP were prepared using a 2-fold serial dilution method). The amount of free $Fab_1$ was then measured using the KinExA instrument by capturing free Fab using hu TSLP-coated beads, washing away unbound material and detecting bound $Fab_1$ fluorometrically using a commercial, species-specific antibody (Alexa Fluor 647 labelled mouse anti-Human Heavy and Light chain specific antibody (Jackson Immunoresearch 209-605-088)). The $K_D$ of $Fab_1$ for hu TSLP was extracted by global 1:1 fit to three datasets, derived from hu TSLP titrations into 1000 pM (filled diamonds), 500 pM (inverted filled triangles) or 40 pM (open squares) fixed $Fab_1$ concentration solutions (FIG. 1). The $K_D$ of $Fab_1$ for cyno TSLP was extracted by global 1:1 fit to two datasets, derived from cyno TSLP titrations into 1000 pM (filled diamonds) or 40 pM (open squares) fixed $Fab_1$ concentration solutions (FIG. 2).

Figure 2:
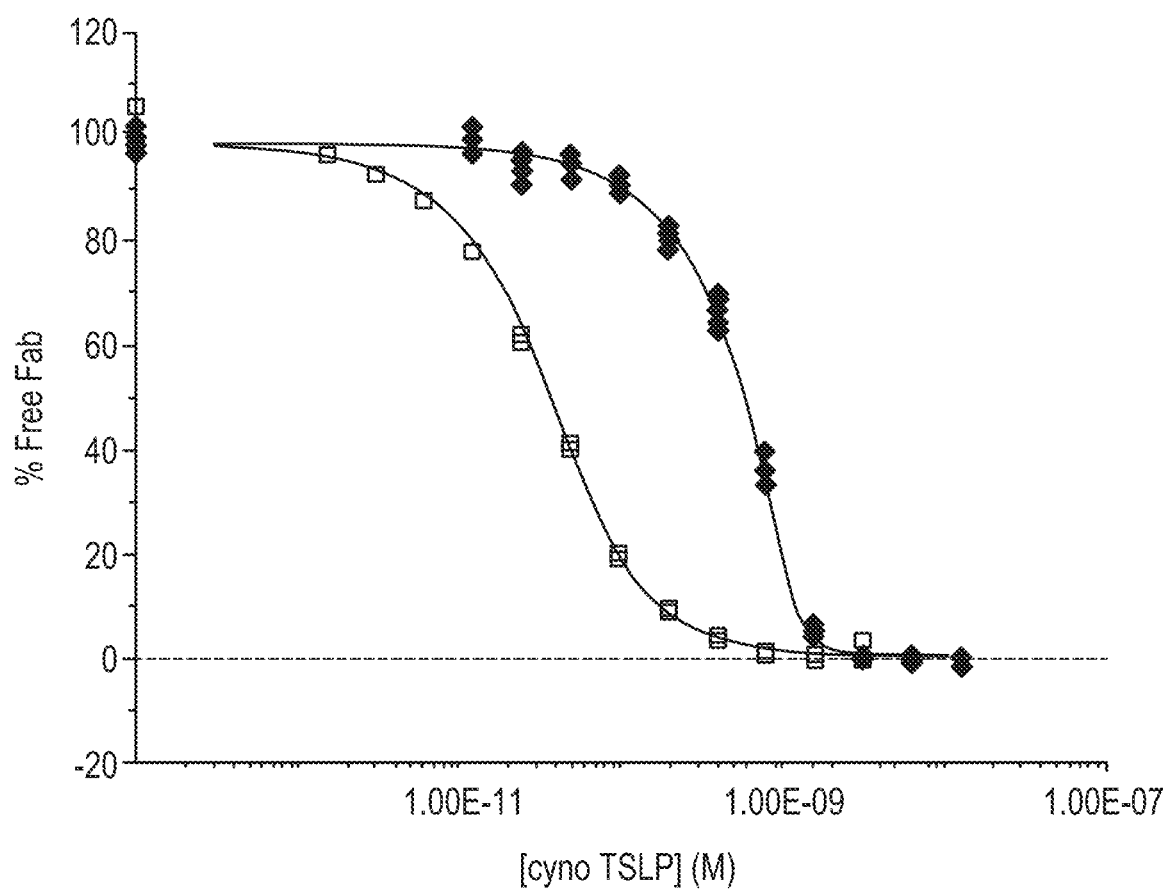
FIG. 2 shows $Fab_1$ binding to cyno TSLP as measured by KinExA.

The amount of free $Fab_1$ detected at each hu and cyno TSLP concentration was plotted against the titrated concentration of TSLP (FIGS. 1 and 2, respectively). The KinExA software was used to calculate the equilibrium dissociation constant (KD). The results shown in Table 6 demonstrate that $Fab_1$ binds to human TSLP with a 1.7-fold higher affinity than it binds to cyno TSLP in free solution.

TABLE 6

Soluble Phase Affinity of $Fab_1$ for hu and cyno TSLP using KinExA

| Ligand | Affinity ($K_D$) pM |
|---|---|
| Human TSLP | 8.0 (95% Conf. Int. 6.27-10.01 pM) |
| cyno TSLP | 13.6 (95% Conf. Int. 9.07-19.22 pM) |

Example 3—Fab1 and Tezepelumab Bind to TSLP with Similar Binding Characteristics The binding characteristics of $Fab_1$ to hu TSLP were directly compared with tezepelumab. Tezepelumab is a human immunoglobulin G2 (lgG2) monoclonal antibody (mAb) that binds to TSLP, preventing its interaction with the TSLP receptor complex. A proof-of-concept study in patients with mild, atopic asthma, demonstrated that tezepelumab inhibited the early and late asthmatic response and suppressed biomarkers of Th2 inflammation following inhaled allergen challenge. Tezepelumab is currently being investigated in the clinic as a specialist care treatment for the treatment of severe asthma.

The in vitro binding potency of $Fab_1$ was determined using a homogeneous fluorescence resonance energy transfer (FRET) Homogeneous Time-Resolved Fluorescence (HTRF®, Cisbio International) based TSLP: mAb-binding assay. Streptavidin cryptate was used for the detection of biotinylated TSLP. In brief, samples of unlabeled $Fab_1$ were titrated into the HTRF assay to compete with DYLIGHT® labelled tezepelumab for binding to biotinylated His-Avi hu TSLP. A competition assay was also preformed using unlabeled tezepelumab and DYLIGHT® labelled tezepelumab as a positive control.

Figure 3:
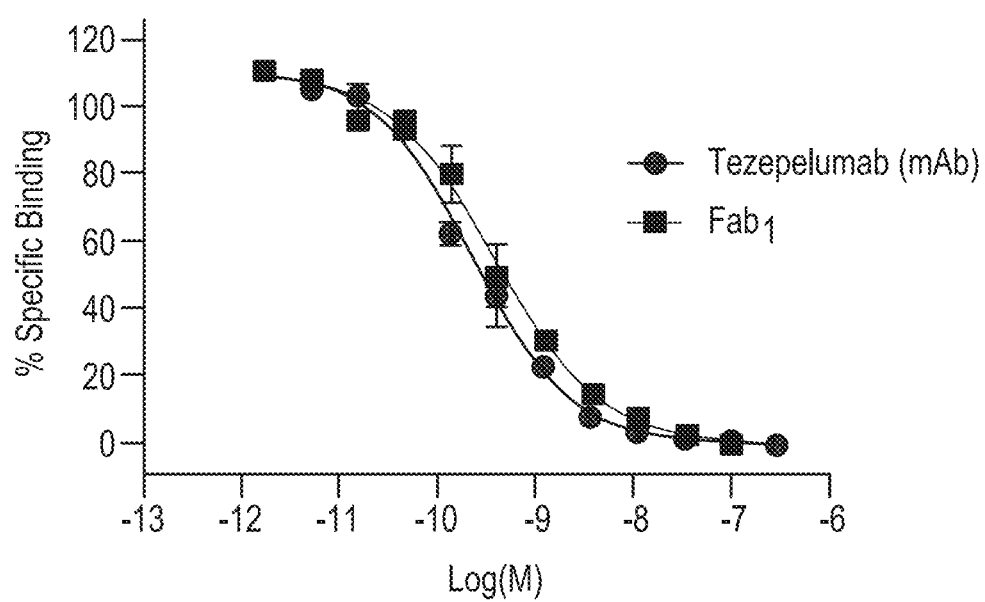
FIG. 3 shows the competitive binding of $Fab_1$ to hu TSLP as measure using the HTRF assay.

The results show that $Fab_1$ competes for binding to huTSLP with tezepelumab and binds to hu TSLP with a similar potency as tezepalumab (IC50: $Fab_1$ —0.38 nM; tezepelumab—0.23 nM—FIG. 3). The HTRF assay was also performed using $Fabs_{2-9}$, which shows that each of these Fabs also compete for binding to hu TSLP with tezepelumab and bind to hu TSLP with a similar potency to tezepelumab (Table 7).

TABLE 7

$IC_{50}$ of $Fabs_{2-9}$ as determined by HTRF assay

| | $IC_{50}$ nM |
|---|---|
| $Fab_2$ | 0.29 |
| $Fab_3$ | 0.24 |
| $Fab_4$ | 0.36 |
| $Fab_5$ | 0.42 |
| $Fab_6$ | 0.32 |
| $Fab_7$ | 0.24 |
| $Fab_8$ | 0.29 |
| $Fab_9$ | 0.29 |

Example 4—$Fab_1$ Neutralizes TSLP Activity in a Peripheral Blood Mononuclear Cell (PBMC) Assay It was next determined whether $Fab_1$ binding to TSLP has functional blocking activity in a primary cell assay by measuring TSLP-induced CCL17 release from PBMCs upon treatment with $Fab_1$.

Blood was obtained from healthy donors under the blood donor program established at MedImmune, Cambridge, UK. Peripheral blood mononuclear cells were isolated by a standard procedure using a ficoll gradient. Briefly, 20 mls of blood diluted with PBS (10 ml blood:30 ml PBS) were layered onto 15 ml ficoll. Tubes were spun at 400 g for 40 mins at room temperature without brake. PBMC layers were collected and cells washed twice with 50 ml PBS. PBMCs were counted using a haemocytometer and trypan blue to exclude dead cells and resuspended in culture media (RPMI with 10% fetal calf serum and 1% penicillin/streptomycin) before plating into a 96-well plate. Cells were stimulated with TSLP (0.5 ng/ml) in the presence of the TSLP-binding antibody fragment Fab$_1$, for 48 h. Assays were also performed using the TSLP-binding antibody tezepelumab, as a positive control. After 48 h, supernatants were removed and assayed for CCL17 production using an R&D duoset ELISA, according to the manufacturer's protocol. Experiments were performed using six donors in three independent experiments.

Figure 4:
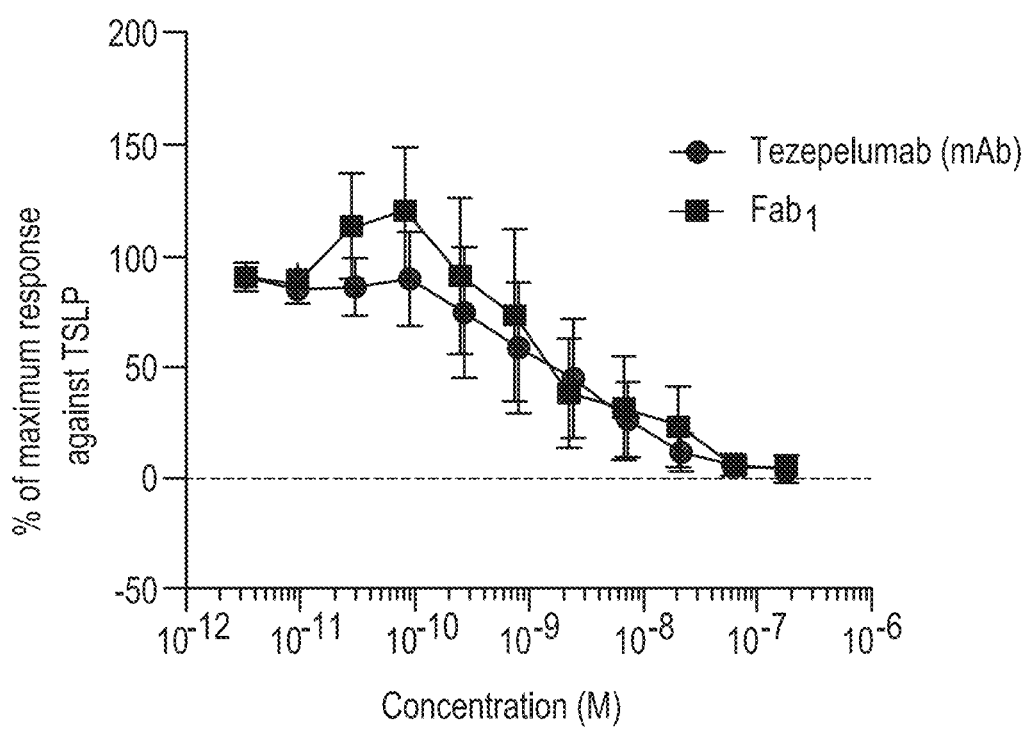
FIG. 4 shows that $Fab_1$ inhibits CCL17 release from PBMCs challenged with TSLP.
Figure 5:
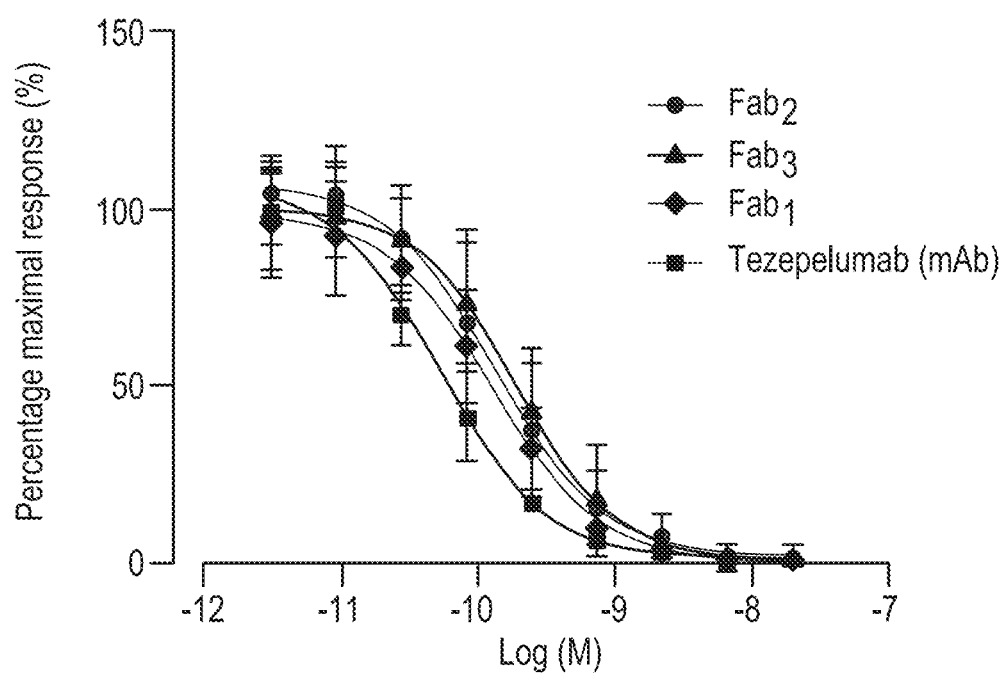
FIG. 5 shows that $Fab_1$, $Fab_2$ and $Fab_3$ inhibit TSLP-induced CCL17 release from PBMCs.

The results show that Fab$_1$ inhibited CCL17 production from PBMCs with an IC$_{50}$ of 1.39 nM (FIG. 4). The assay was repeated using in addition to Fab$_1$, Fab$_2$ and Fab$_3$ (comprising the variable heavy chain and variable light chain sequences as outlined in Table 3) and similar results were obtained (FIG. 5).

Example 5—Determining Maximum Tolerated Dose and Pharmacokinetics Following Fab1 Inhalation in Cynomolgus Monkeys The objective of the study was to determine the maximum tolerated dose (MTD) or maximum feasible dose (MFD) and the pharmacokinetics (PK) of aerosolized Fab$_1$ after inhalation exposure via face mask in Cynomolgus macaques.

Female cynomolgus monkeys received a single 8 min and 20 min inhalation of Fab$_1$ (Groups 1 and 2, three animals per group). The doses delivered to the lung for Group 1 and 2 were 1 and 2 mg/kg based on 25% lung deposition. Group 3 was a repeat dose escalation. One female and one male cynomolgus monkeys were treated as follows: 8 min inhalation daily for the first 2 days, 20 min inhalation daily for 2 days, 60 min inhalation daily for 3 days. Serial blood samples were for collected for Fab$_1$ serum PK and urea concentration. Bronchoalveolar lavage (BAL) samples were collected for Fab$_1$ PK and urea concentration. The Epithelial lining fluid (ELF) was calculated from BAL using the urea concentration as dilution marker. The hybrid immunoaffinity LC-MS/MS method was used to determine Fab$_1$ concentration in serum and BAL sample matrixes. The lower limit of quantitation was 4 ng/mL in serum and 10 ng/mL in BAL. Non-compartmental (NCA) analysis was performed on the individual plasma PK data using Phoenix WinNonlin (version 7.0, Certara, L. P., St Louis, MO.).

Figure 6A:
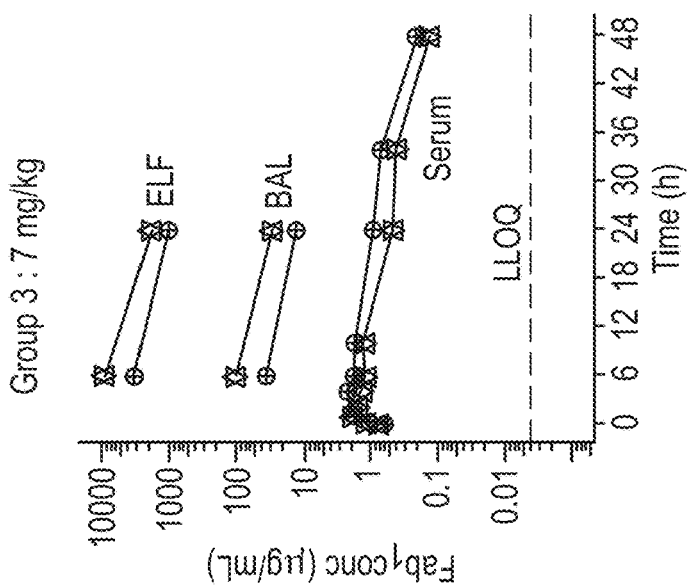
FIGS. 6A-6C show the $Fab_1$ serum, BAL, and ELF PK profiles following the single (Group 1 and 2) and repeat dose escalation (Group 3) inhalation.
Figure 6B:
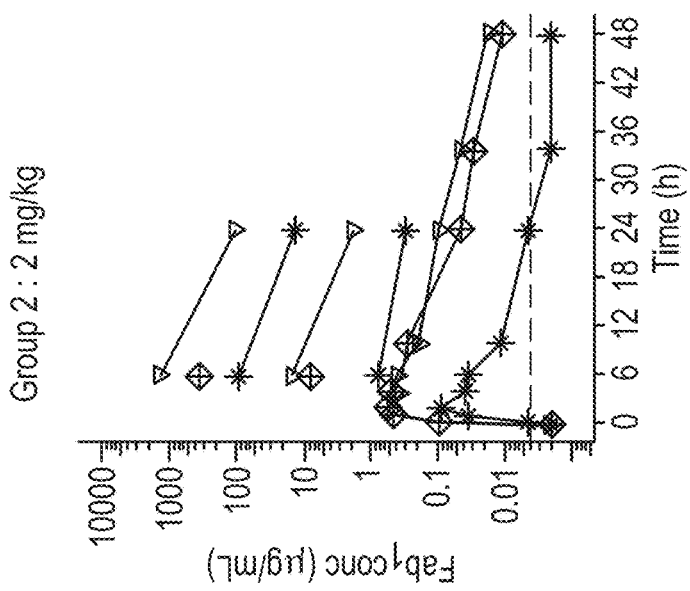
Figure 6C:
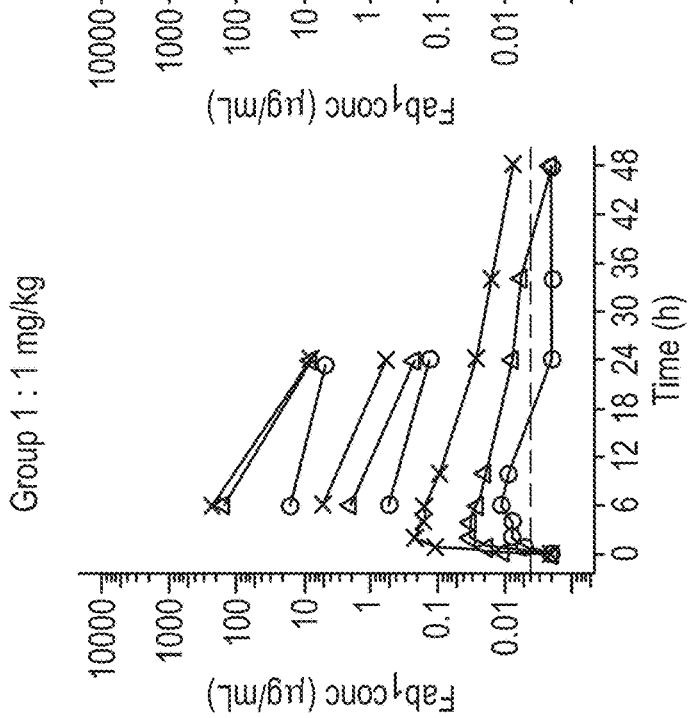
Figure 7:
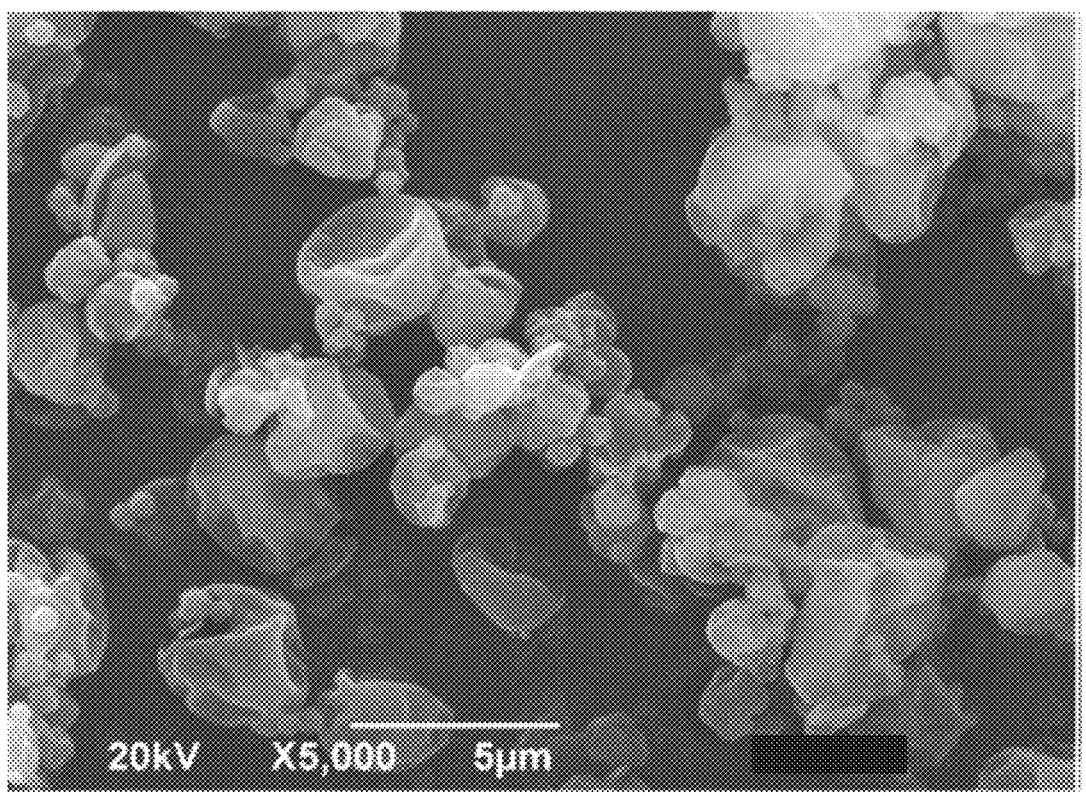
FIG. 7 shows microparticles from a dry powder formulation in accordance with embodiments hereof.

Following the inhalation of Fab$_1$, the serum PK, BAL and ELF concentration increase with dose, and there was high variability in Fab$_1$ concentration (FIGS. 6A-6C). The mean serum terminal half-life of Fab1 ranges between 9.75 to 13.6 h. Serum C$_{max}$ was reached at the median T$_{max}$ of 2 to 4 hr post-inhalation. The concentration of ELF was much higher than serum following inhalation (>2000-fold higher) suggesting that the distribution of Fab$_1$ to serum was low following inhalation dose.

Example 6: Evaluating Physical Characteristics of Spray-Dried Formulations Comprising Leucine and Trileucine The following methods evaluate the impact of trileucine and leucine concentration ratios on particle properties.

In total, 24 powders of varying trileucine, leucine, and trehalose (TLT) wt % were spray-dried on a pilot scale spray dryer using identical process parameters at a total feedstock solids concentration of 10%. Since feedstocks were prepared at a total solids concentration of 10% (100 mg/mL), all wt % values in this study are also identical to concentration values (mg/mL). The range of concentration values for each particle excipient is shown in Table 8.

TABLE 8

Particle Component Composition Ranges

| Component | Minimum Value | Maximum Value |
|---|---|---|
| TriLeucine | 0.71 mg/mL | 5.72 mg/mL |
| Leucine | 0.62 mg/mL | 19.94 mg/mL |
| Trehalose | 65.84 mg/mL | 90.16 mg/mL |
| TriSodium Citrate | 8.5 mg/mL | 8.5 mg/mL |

Each feedstock (Table 9) was prepared by dissolving the excipients in water. Once all excipients were fully dissolved, feedstocks were spray dried, using the following process parameters: outlet temperature, 70° C.; feedstock feed rate, 12 ml/min; atomizer gas flow, 13 kg/hr; and drying gas flow, 80 kg/hr. The parameters were selected to achieve the target particle and aerosol properties for a dry powder formulation intended for inhalation. Each of the 24 formulations were manufactured at an 18 g batch-size to provide sufficient powder for characterization and product performance evaluation. Batches were randomized and produced across two days.

TABLE 9

Feedstock Concentrations for Formulations 1-24

| Run | Trileucine Conc. mg/mL | Leucine Conc. mg/mL | Trehalose Conc. mg/mL | TriSodium Citrate Conc mg/mL | leucine/trileucine concentration ratio |
|---|---|---|---|---|---|
| 1 | 1.43 | 13.08 | 76.99 | 8.5 | 9.1 |
| 2 | 0.71 | 0.62 | 90.16 | 8.5 | 0.9 |
| 3 | 0.71 | 4.98 | 85.80 | 8.5 | 7.0 |
| 4 | 0.71 | 19.94 | 70.85 | 8.5 | 28.1 |
| 5 | 1.43 | 16.20 | 73.87 | 8.5 | 11.3 |
| 6 | 2.86 | 14.95 | 73.69 | 8.5 | 5.2 |
| 7 | 2.86 | 9.97 | 78.67 | 8.5 | 3.5 |
| 8 | 2.86 | 19.94 | 68.70 | 8.5 | 7.0 |
| 9 | 2.86 | 4.36 | 84.28 | 8.5 | 1.5 |
| 10 | 5.72 | 19.94 | 65.84 | 8.5 | 3.5 |
| 11 | 0.71 | 15.58 | 75.21 | 8.5 | 21.9 |
| 12 | 5.72 | 15.58 | 70.20 | 8.5 | 2.7 |
| 13 | 5.00 | 11.84 | 74.66 | 8.5 | 2.4 |
| 14 | 0.71 | 7.48 | 83.31 | 8.5 | 10.5 |
| 15 | 2.86 | 0.62 | 88.02 | 8.5 | 0.2 |
| 16 | 3.57 | 18.07 | 69.86 | 8.5 | 5.1 |
| 17 | 5.72 | 0.62 | 85.16 | 8.5 | 0.1 |
| 18 | 5.72 | 6.23 | 79.55 | 8.5 | 1.1 |
| 19 | 1.43 | 11.22 | 78.85 | 8.5 | 7.0 |
| 20 | 0.71 | 9.97 | 80.82 | 8.5 | 14.0 |
| 21 | 4.29 | 3.12 | 84.10 | 8.5 | 0.7 |
| 22 | 4.29 | 16.82 | 70.39 | 8.5 | 3.9 |
| 23 | 5.72 | 9.97 | 75.81 | 8.5 | 1.7 |
| 24 | 3.57 | 9.97 | 77.96 | 8.5 | 2.8 |

The following physical powder characteristics were tested for all formulations

TABLE 10

Particle Parameters Analyzed

| Analysis/DOE Output | Instrument |
|---|---|
| Residual Moisture Content | Oven KF |
| Primary Particle Size Distribution | Sympatec R |
| Glass Transition Temperature (Tg) | DSC |
| Compressed Bulk Density[1] | GeoPyc |
| SEM Visual Morphology (qualitative) | SEM |
| Specific Surface Area | BET |
| Crystallinity (qualitative) | XRPD |

TABLE 10-continued

| Particle Parameters Analyzed | |
| --- | --- |
| Analysis/DOE Output | Instrument |
| Excipient Surface Coverage on Particle | ToF-SIMS |

[1]Compression force of 300,000 N/m², or 38N if using a 12.7 mm sample chamber.

The compressed bulk density (CBD) of the powders were measured using a GeoPyc® Model 1360 density analyzer (Micromeritics, Norcross, GA.). Powder samples were prepared in a low humidity environment (<5% RH), before transfer into the density analyzer sample chamber that had been purged with nitrogen gas. The net weight of the powder sample was recorded, and then a compression force of 12N was applied to the sample by a plunger, at a rate of 300 consolidation steps per second. The linear distance travelled by the plunger for each consolidation step was translated into a volume displacement of the powder sample. An average of the measurements from each consolidation step was then transformed into a calculated bulk density value, expressed in g/cm³.

The results show that the leucine and trileucine content were found to have a significant impact on particle properties. Trileucine was identified as being the primary factor with the largest impact, while leucine was identified as a secondary factor with also a notable impact. The results are summarized in Table 11.

TABLE 11

| Results of Particle Characterization | |
| --- | --- |
| Analysis/DOE Output | Impact |
| Residual Moisture Content | Correlation of reducing moisture content with increasing Leucine Content (see FIG. 14) |
| Primary Particle Size Distribution | No trend observed with Leucine or TriLeucine |
| Glass Transition Temperature (Tg) | No trend observed with Leucine or TriLeucine |
| Compressed Bulk Density[1] | Primary Negative Correlation with TriLeucine; Secondary Negative Correlation with Leucine. cBD of between 0.45 to 0.85 g/cm³ (FIG. 8A) |
| SEM Visual Morphology | Positive Correlation with TriLeucine and surface roughness/rugosity (FIG. 11A-11D) |
| Specific Surface Area | Primary Positive Correlation with TriLeucine; Secondary Positive Correlation with Leucine The SSA of the formulations is from 2.5 to 6.5 m²/g (FIG. 9) |
| Crystallinity | Greater Crystallinity was achieved at Higher Leucine contents combined with lower TriLeucine contents |
| Excipient Particle Surface Coverage | Greater Surface coverage achieved with increasing TriLeucine and Leucine wt % (50% particle coverage of Trileucine was achieved above 1.4 wt %) |

[1]Compression force of 300,000 N/m², or 38N if using a 12.7 mm sample chamber.

Example 7—Aerosol Performance Characteristics of Leucine/Trileucine Formulations The following example evaluates the aerosol performance of formulations comprising leucine and trileucine in a dry powder inhaler device. The aerosol performance outputs listed in Table 7 were tested on 20 of the 24 formulations listed in Table 4. All product performance characterization was completed using a Monodose RS01 device, with size 3 capsules. Next Generation Impactor (NGI) analysis was performed at a 60 L/min flow rate.

Cascade impaction testing was performed as per USP <601> to measure the aerosol performance of the spray dried formulations when delivered from a dry powder inhaler device. The cascade impactor apparatus used was the Next Generation Impactor (NGI; USP41, Chapter <601>). For the aerosol measurements made in these examples, one Size 3 HPMC capsule containing the spray dried powder formulation was dispersed from the dry powder inhaler device and delivered into the NGI under a vacuum pulled at 60 L/min as per USP methodology. Samples from each stage of the NGI were recovered and assayed for protein content by UV absorption at 280 nm. The main aerosol performance parameters calculated from these measurements were a) Fine Particle Fraction<5 μm (FPF<5 μm), defined as the fraction of powder emitted from the device that is measured to be <5 μm in aerodynamic particle diameter; and b) median mass aerodynamic diameter MMAD.

TABLE 12

| Aerosol Characterization | |
| --- | --- |
| Analysis/DOE Output | Instrument/Technique used |
| Mean mass aerodynamic diameter (MMAD) | NGI |
| % Device Deposition | NGI |
| % FPF <5 um | NGI |

The results of the aerosol analysis are summarized in Table 13.

TABLE 13

Figure 12:
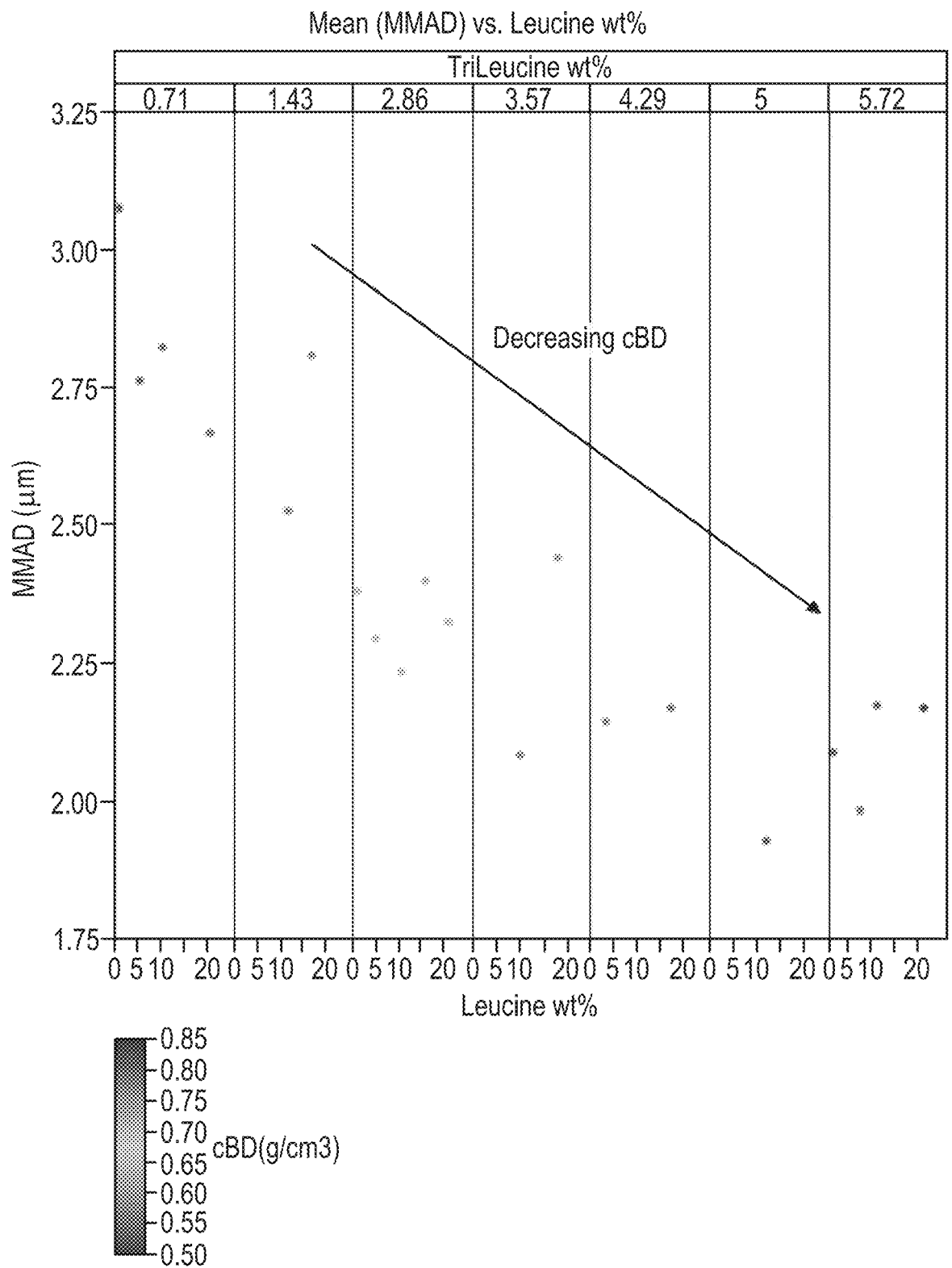
FIG. 12 shows the correlation between median mass aerodynamic diameter (MMAD) and leucine and trileucine wt % values.
Figure 13:
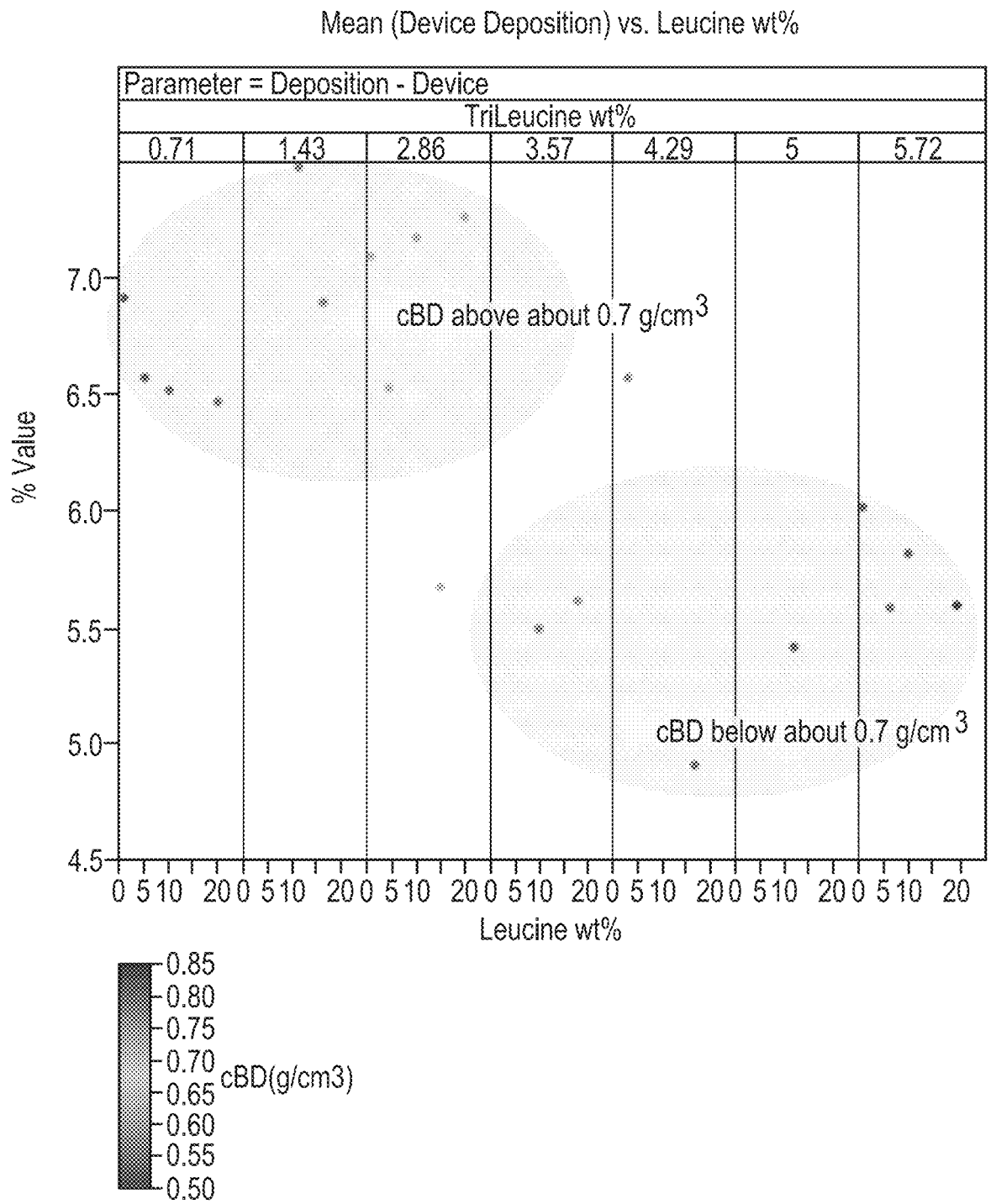
FIG. 13 shows the correlation between device deposition and leucine and trileucine wt % values.
Figure 17A:
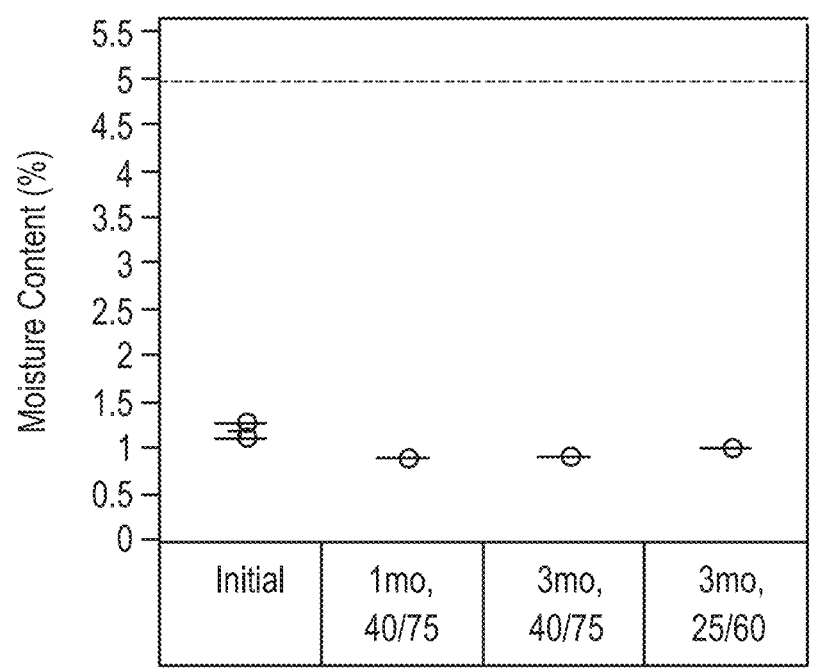
FIG. 17A shows the moisture content % of a formulation comprising 40% (w/w) $Fab_1$ and 1.1% PS-80 following storage for 1 or 3 months at 40° C. and 75% relative humidity (40/75) and for 3 months at 25° C. and 60% relative humidity (25/60)
Figure 17B:
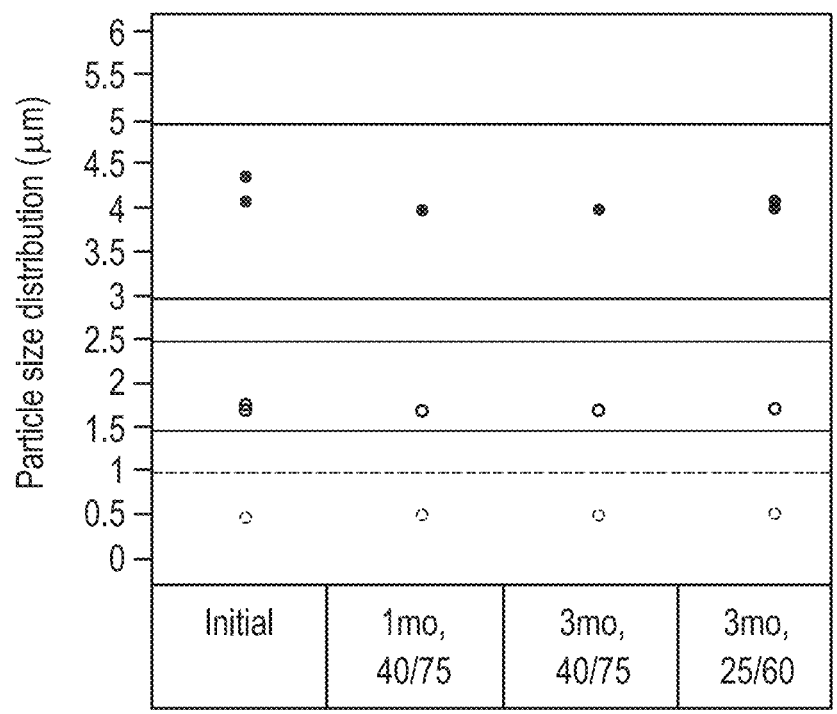
FIG. 17B shows the particle size distribution (PSD) of a formulation comprising 40% (w/w) $Fab_1$ and 1.1% PS-80 following storage for 1 or 3 months at 40° C. and 75% relative humidity (40/75) and for 3 months at 25° C. and 60% relative humidity (25/60)
Figure 18A:
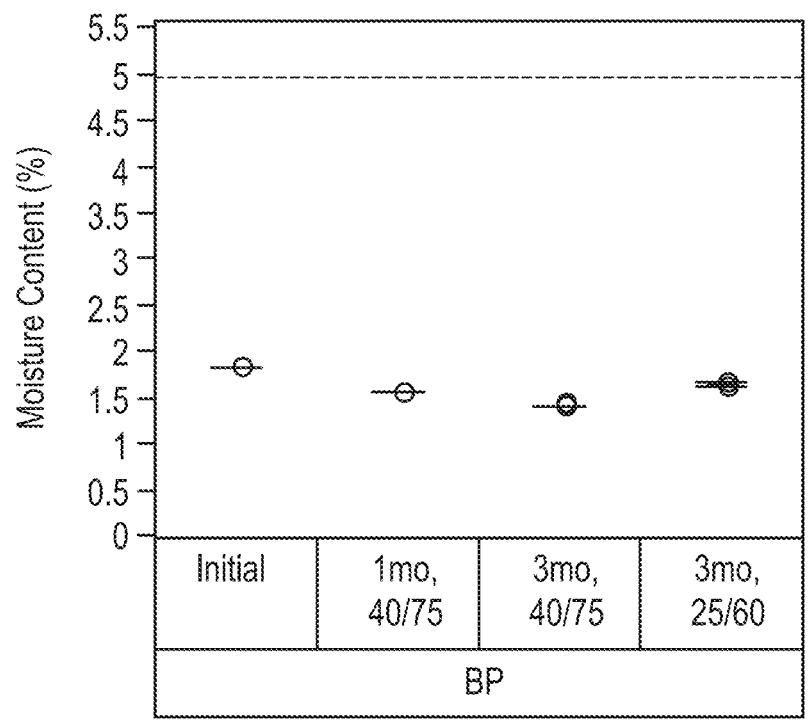
FIG. 18A shows the moisture content % of a formulation comprising 1% (w/w) $Fab_1$ and 1.1% PS-80 following storage for 1 or 3 months at 40° C. and 75% relative humidity (40/75) and for 3 months at 25° C. and 60% relative humidity (25/60)
Figure 18B:
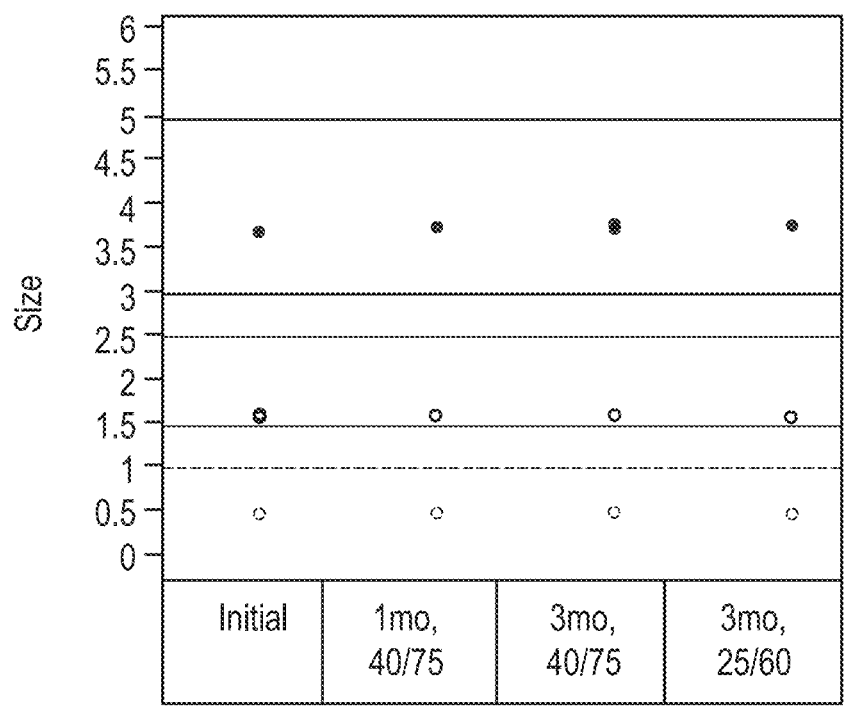
FIG. 18B shows the particle size distribution (PSD) of a formulation comprising 1% (w/w) $Fab_1$ and 1.1% PS-80 following storage for 1 or 3 months at 40° C. and 75% relative humidity (40/75) and for 3 months at 25° C. and 60% relative humidity (25/60)

| Results of Aerosol Characterization | |
| --- | --- |
| Analysis/DOE Output | Impact |
| MMAD (median mass aerodynamic diameter) | Strong Negative Correlation with TriLeucine. A range of MMAD values of from 1.75 to 3.25 μm were achieved (FIG. 12). |
| % Device Deposition | Stepwise correlation with TriLeucine. In general, a trileucine wt % of above 3% resulted in a reduction in device deposition (FIG. 13). |
| % FPF (fine particle fraction) <5 μm | Positive Correlation with TriLeucine Negative Correlation with Leucine. All 20 of the tested formulations had FPFs of >60%, indicating good performance (FIG. 14). |

Example 8—Generating Inhalable Leucine/Trileucine Formulations Comprising an Anti-TSLP Antibody Binding Fragment (Fab)

The characteristics of another formulation comprising a different Fab were tested. An anti-TSLP Fab was used, derived from a human IgG1 monoclonal antibody that specifically binds TSLP (thymic stromal lymphopoetin) (see the sequences set forth in SEQ ID NOS: 1-8 provided herein). Distinct formulations comprising the mass concentrations outlined in Table 14 were generated.

TABLE 14

Compositions of spray dried formulations containing anti-TSLP Fab

| Formulation | Anti-TSLP Fab [% w/w] | Trehalose [% w/w] | Leucine [% w/w] | Trileucine [% w/w] | Citrate, pH 6.0 [% w/w] |
|---|---|---|---|---|---|
| #1 | 1 | 78 | 10.5 | 2 | 8.5 |
| #2 | 12 | 67 | 10.5 | 2 | 8.5 |
| #3 | 40 | 39 | 10.5 | 2 | 8.5 |

The anti-TSLP Fab was initially received in a liquid buffer comprising 105 mM trehalose, 30 mM citrate, pH 6.0. Leucine, trileucine, trehalose and citrate were dissolved into a separate aqueous solution, which was then added to the anti-TSLP Fab solution to create bulk liquid feedstock solutions for spray drying. Table 15 summarizes the feedstock compositions prepared in order to achieve the target powder formulation compositions. The liquid feedstock solutions were then spray dried, using process parameters listed in Table 16. The parameters were selected to achieve the target particle and aerosol properties for a dry powder formulation intended for inhalation.

TABLE 15

Compositions of Liquid Feedstocks for Spray Drying

|  | Formulation #1 | Formulation #2 | Formulation #3 |
|---|---|---|---|
| Anti-TSLP Fab [mg/mL] | 0.75 | 9.0 | 24 |
| Trehalose [mg/mL] | 58.5 | 50.3 | 23.4 |
| Leucine [mg/mL] | 7.9 | 7.9 | 6.3 |
| Trileucine [mg/mL] | 1.5 | 1.5 | 1.2 |
| Citrate pH 6.0 [mg/mL] | 6.4 | 6.4 | 5.1 |
| Total feedstock concentration [mg/mL] | 75 | 75 | 60 |

TABLE 16

Key spray drying process parameters

|  | Formulation #1 | Formulation #2 | Formulation #3 |
|---|---|---|---|
| Outlet temperature (° C.) | 70 | 70 | 70 |
| Feedstock feed rate (mL/min) | 20 | 17 | 3 |
| Atomizer Gas Flow (kg/h) | 13 | 13 | 2.1 |
| Drying gas flow (kg/hr) | 155 | 155 | 59.5 |

Results from powder and aerosol performance characterization of the spray dried formulations are summarized in Table 17. For aerosol performance measurements, all three formulations were tested with 20 mg of spray dried powder filled in a Size 3 HPMC capsule and dispersed from a dry powder inhaler device.

TABLE 17

Powder and aerosol properties of spray dried anti-TSLP Fab-containing formulations

|  | Formulation #1 1% w/w anti-TSLP Fab | Formulation #2 12% w/w anti-TSLP Fab | Formulation #3 40% w/w anti-TSLP Fab |
|---|---|---|---|
| oVMD [µm] (n = 2) | 1.5 (d50) | 1.5 (d50) | 1.9 (d50) |
|  | 3.5 (d90) | 3.5 (d90) | 4.1 (d90) |
| cBD [g/cm$^3$] | 0.72 | 0.70 | 0.58 |
| SSA [m$^2$/g] | 3.5 | 4.12 | 4.6 |
| FPM$_{<5\ \mu m}$ [mg Fab$_1$] (n = 3) | 0.17 | 1.9 | 5.9 |
| FPF$_{<5\ \mu m}$ [%] (n = 3) | 95.1 | 94.3 | 85.4 |
| MMAD (n = 3) | 2.3 | 2.2 | 2.7 |

Of particular note is the success in filling 50 mg of Formulation #3 into a single Size 3 HPMC capsule, attributable to the high bulk density of the powder. The high bulk density (cBD) enabled the delivery of a very high payload from a single capsule (FPM<5 µm of about 14 mg, FPF of 82%, MMAD of 2.4 µm).

In addition, Formulation #3, exhibits a similar cBD (0.58 g/cm3) and SSA (4.6 m2/g) to that of anti-IL-4 Fab Formulation #2 (cBD=0.59 g/cm3, SSA=4.5 m2/g), suggesting that the powder properties translate between pharmaceutical formulations comprising different active ingredients.

Example 9—Powder and Aerosol Properties of Spray Dried Anti-TSLP Formulations at Three Batch Sizes This example provides an analysis of the powder and aerosol properties of the anti-TSLP Fab leucine/trileucine formulations using greater batch sizes to enable non-GLP and GLP inhalation toxicology studies. Scale up requires the use of alternative scale spray dryer equipment, and adjustments to spray drying process parameters, to account for increased heat and mass flow through the system and the need for extended processing runs.

Three batches of a spray dried anti-TSLP Fab formulations were manufactured in increasing batch sizes. The batches comprised: anti-TSLP Fab 40% w/w, trehalose 39% w/w, leucine 10.5% w/w, trileucine 2% w/w, and citrate pH 6.0 8.5% w/w. The process parameters selected for each batch are shown in Table 18.

TABLE 18

Spray dryer process parameters for three anti-TSLP Fab formulation batches of increasing batch size

|  | Batch #1 | Batch #2 | Batch #3 |
|---|---|---|---|
| Feedstock concentration [mg/mL] | 60 | 75 | 75 |
| Outlet temperature (° C.) | 70 | 70 | 70 |
| Feedstock feed rate (mL/min) | 3 | 5 | 12 |
| Atomizer Gas Flow (kg/h) | 2.1 | 2.1 | 13.3 |
| Drying gas flow (kg/hr) | 59.5 | 59.5 | 155 |
| Total batch size* | 8.5 g | 348 g | 1.2 kg |
| Spray dryer | Lab-scale | Lab-scale | Intermediate-scale |
| Days/hours of production | 1 day/1.1 h | 2 days/15.9 h | 2 days/22.4 h |

*Processed powder weight.

Aerosol performance testing of Batch #1 was performed with a powder fill mass of 50 mg in a Size 3 HPMC capsule, while Batches #2 and #3 were tested with a 20 mg fill mass. While there is a slight increase in the oVMD as the batch size increased from batch size 8.5 g to 1.2 kg, a compressed bulk powder density (cBD) of between 0.45 and 0.85 g/cm$^3$ was achieved. The aerosol performance of the powders were also maintained independent of batch size, with a high payload delivery of anti-TSLP Fab from the capsule-based inhaler device. The demonstrates the scalability of the formulation with minimal adjustments to the spray dryer process. The full results of powder characterization and aerosol performance testing are summarized in Table 19.

TABLE 19

Powder properties and aerosol performance for three anti-TSLP Fab batches of increasing batch size

|  | Batch #1 | Batch #2 | Batch #3 |
|---|---|---|---|
| oVMD [µm] (n = 2) | 1.5 (d50) | 1.7 (d50) | 1.9 (d50) |
|  | 3.2 (d90) | 3.8 (d90) | 4.1 (d90) |
| CBD [g/cm$^3$] |  |  | 0.58 |
| SSA [m$^2$/g] |  |  | 4.6 |
| FPM$_{<5\ \mu m}$ [mg anti-TSLP Fab] (n = 3) | 14.3 | 5.6 | 5.9 |
| FPF$_{<5\ \mu m}$ [%] (n = 3) | 81.9 | 83.4 | 85.4 |
| MMAD [µm] (n = 3) | 2.4 | 2.4 | 2.7 |

Example 10 Further Characterization of Leucine/Trileucine Formulations Comprising a Surfactant Additional batches of trileucine/leucine formulations comprising varying amounts of PS-80 were generated. The formulation compositions and process parameters for the generation of each batch are shown in Table 20. Otherwise, formulation generation was as described in example 6.

TABLE 20

Formulation compositions and spray dry process parameters for formulations comprising increasing amounts of PS-80

| Description | 40% FAB$_1$, control (no PS80) | | 40% FAB$_1$, 0.27% w/w PS80 (0.02% w/v PS80) | | 40% FAB$_1$ 0.67% w/w PS80 (0.05% w/v PS80) | | 40% FAB$_1$, 1.33% w/w PS80 (0.10% w/v PS80) | | 40% FAB$_1$, 2.00% w/w PS80 (0.15% w/v PS80) | | 40% FAB$_1$, 2.67% w/w PS80 (0.20% w/v PS80) | |
|---|---|---|---|---|---|---|---|---|---|---|---|---|
| Composition | % w/w | mg/ml | % w/w | mg/ml | % w/w | mg/ml | % w/w | mg/ml | % w/w | mg/ml | % w/w | mg/ml |
| MEDI8630 | 40.00 | 29.60 | 40.00 | 29.60 | 40.00 | 30.00 | 40.00 | 30.00 | 40.00 | 30.00 | 40.00 | 29.20 |
| TriSodium Citrate Anhydrous | 7.75 | 5.74 | 7.75 | 5.74 | 7.75 | 5.81 | 7.75 | 5.81 | 7.75 | 5.81 | 7.75 | 5.66 |
| Citric Acid Anhydrous | 0.75 | 0.56 | 0.75 | 0.56 | 0.75 | 0.56 | 0.75 | 0.56 | 0.75 | 0.56 | 0.75 | 0.55 |
| Trehalose Anhydrous | 39.00 | 28.86 | 38.73 | 28.66 | 38.34 | 28.75 | 37.67 | 28.26 | 37.02 | 27.76 | 36.29 | 26.49 |
| TriLeucine | 2.00 | 1.48 | 2.00 | 1.48 | 2.00 | 1.50 | 2.00 | 1.50 | 2.00 | 1.50 | 2.00 | 1.46 |
| Leucine | 10.50 | 7.77 | 10.50 | 7.77 | 10.50 | 7.88 | 10.50 | 7.88 | 10.50 | 7.88 | 10.50 | 7.67 |
| PS80 | 0.00 | 0.00 | 0.27 | 0.20 | 0.66 | 0.50 | 1.33 | 0.99 | 1.98 | 1.49 | 2.71 | 1.98 |
| Drying gas (slpm) | 850 | | 850 | | 850 | | 850 | | 850 | | 850 | |
| Liq feed rate (ml/min) | 5 | | 5 | | 5 | | 5 | | 5 | | 5 | |
| Atomizer (slpm) | 30 | | 30 | | 30 | | 30 | | 30 | | 30 | |
| Inlet temp (° C.) | 100 | | 100 | | 100 | | 100 | | 100 | | 100 | |
| Outlet temp (° C.) | 70 | | 70 | | 70 | | 70 | | 70 | | 70 | |
| GLR | 7 | | 7 | | 7 | | 7 | | 7 | | 7 | |
| Run time (hr) | 0.68 | | 0.27 | | 0.67 | | 0.67 | | 0.67 | | 0.68 | |

The aerosol properties of the formulations in Table 20 were analyzed using the methods disclosed in Example 7. The results of the analysis are shown in Table 21.

TABLE 21 aerosol performance of formulations comprising PS-80

| Description | % FPF (<5.0 um) | FPM (<5.0 um) (mg) | MMAD (um) |
|---|---|---|---|
| 40% FAB$_1$, control | 78 | 5.5 | 2.55 |
| 40% FAB$_1$, 0.27% w/w PS80 | 77 | 5.9 | 2.56 |
| 40% FAB$_1$, 0.67% w/w PS80 | 70 | 4.4 | 2.68 |
| 40% FAB$_1$, 1.33% w/w PS80 | 75 | 4.5 | 2.7 |
| 40% FAB$_1$, 2.00% w/w PS80 | 82 | 4.2 | 2.27 |
| 40% FAB$_1$, 2.67% w/w PS80 | 68 | 4.0 | 2.63 |

Aggregate content, oVMD, residual moisture content, Tg, cBD and SSA were also measured using the methods described in the preceding examples. Results of the powder property analysis are shown in Table 22.

TABLE 22

Powder properties of dry powder formulations comprising FAB$_1$ and varying (w/w) amounts of PS-80.

| % w/w PS80 | | 0% | 0.27% | 0.67% | 1.33% | 2.00% | 2.67% |
|---|---|---|---|---|---|---|---|
| HP-SEC | % MPP | 99.3 | 99.3 | 99.5 | 99.5 | 99.5 | 99.4 |
| | % Agg | 0.1 | 0.1 | 0.2 | 0.2 | 0.1 | 0.1 |
| oVMD | d10 (μm) | 0.5 | 0.5 | 0.5 | 0.5 | 0.5 | 0.5 |
| | d50 (μm) | 1.8 | 1.8 | 1.8 | 1.7 | 1.2 | 1.5 |
| | d90 (μm) | 4 | 3.9 | 4.0 | 3.9 | 2.9 | 4.6 |
| | Span | 1.9 | 1.9 | 2.0 | 2.0 | 2.1 | 2.7 |
| Residual moisture (%) | | 1.6 | 1.6 | 1.7 | 1.9 | 1.9 | 0.4 |
| Tg | Open (° C.) | 123 | 124 | 121 | 121 | 121 | 124 |
| | Closed (° C.) | 99 | 98 | 96 | 95 | 96 | 115 |
| cBD (g/cm3) | | 0.58 | 0.60 | 0.59 | 0.59 | nm* | 0.55 |
| SSA (m2/g) | | 4.60 | 5.02 | 4.37 | 4.05 | nm | 4.24 |

*nm - not measured

The analysis shows that powder properties are largely equivalent to the control formulation irrespective of % (w/w) amount of PS-80.

The formulations described in Table 22 were next analyzed for the content of sub-visible particles (SVPs). The sub-visible particles (SVP) counts were measured using the micro-flow imaging technology (MFI). MFI combines microfluidic flow microscopy and high resolution imaging particle analysis to quantify SVP counts and bin these counts across a particle size range. Prior to testing, powder samples were dissolved in water, and gently swirled to ensure uniform particle distribution then loaded on Protein Simple MFI 5200 (CA, USA). The results were reported as the counts for different particle sizes (≤1 μm, ≤2 μm, ≤5 μm, ≤10 μm and ≤25 μm) per ml. FIG. 14A shows that inclusion of 0.27% (w/w/) PS-80 in the dry powder formulation reduces the absolute number of SVPs per ml on reconstitution. The reduction in SVPs counts decreases with increasing concentration of PS-80. Significant decreases in SVPs were seen on addition of 0.67% (w/w) PS-80, with a negligible amount of SVPs with a particle diameter of greater than 5 μm. The trend was observed when the formulation was reconstituted to a concentration of 30 mg/ml FAB$_1$ or 2.5 mg/ml FAB$_1$ (FIG. 14B).

Formulation characterization and analysis of SVPs were carried out as described above for a second excipient-containing formulation. In this study, poloxamer 188, as opposed to PS-80, was used as the excipient.

Multiple % w/w amounts of poloxamer 188 were examined. The formulation compositions and process parameters for the generation of each formulation batch were as described in Table 20 for PS-80-containing formulations. The amount of trehalose was modified to compensate for the variable amount of poloxamer 188.

Aggregate content, oVMD, residual moisture content, Tg, cBD and SSA were also measured using the methods described in the preceding examples. Results of the powder property analysis are shown in Table 23.

TABLE 23

Powder properties of dry powder formulations comprising FAB$_1$ and varying (w/w) amounts of Poloxamer-188.

| % w/w P-188 | | 0 | 0.67% | 1% | 1.67% | 2.67% | 10% |
|---|---|---|---|---|---|---|---|
| HP-SEC | % MPP | 99.3 | 99.5 | 99.3 | 99.5 | 99.5 | 99.3 |
| | % Agg | 0.1 | 0.2 | 0.2 | 0.2 | 0.2 | 0.2 |
| oVMD | d10 (μm) | 0.5 | 0.5 | 0.5 | 0.5 | 0.5 | 0.5 |

TABLE 23-continued

Powder properties of dry powder formulations comprising $FAB_1$ and varying (w/w) amounts of Poloxamer-188.

| % w/w P-188 | | 0 | 0.67% | 1% | 1.67% | 2.67% | 10% |
|---|---|---|---|---|---|---|---|
| | d50 (μm) | 1.8 | 1.9 | 1.8 | 1.8 | 1.7 | 1.8 |
| | d90 (μm) | 4.0 | 4.2 | 3.9 | 4.2 | 4.1 | 4.3 |
| | Span | 1.9 | 2.0 | 1.9 | 2.1 | 2.1 | 2.1 |
| Residual moisture (%) | | 1.6 | 1.3 | 1.9 | 1.2 | 1.2 | 1.5 |
| Tg | Open (° C.) | 123 | 122 | 121 | 123 | 123 | 122 |
| | Closed (° C.) | 99 | 102 | 94 | 103 | 103 | 98 |
| cBD (g/cm3) | | 0.58 | 0.60 | 0.57 | 0.67 | 0.75 | nm* |
| SSA (m2/g) | | 4.60 | Nm | 4.71 | Nm | 4.45 | nm |

*nm - not measured

The aerosol properties of the Poloxamer-188 formulations were also analyzed using the methods disclosed in Example 7. The results are shown in Table 24.

TABLE 24 aerosol performance of formulations comprising Poloxamer-188 (P188)

| Description | % FPF (<5.0 um) | FPM (<5.0 um) (mg) | MMAD (um) |
|---|---|---|---|
| 40% $FAB_1$, control | 78 | 5.5 | 2.55 |
| 40% $FAB_1$, 0.67% w/w P188 | 67 | 4.5 | 2.61 |
| 40% $FAB_1$, 1% w/w P188 | 86 | 5.4 | 2.82 |
| 40% $FAB_1$, 1.67% w/w P188 | 66 | 4.2 | 2.76 |
| 40% $FAB_1$, 2.67% w/w P188 | 70 | 4.6 | 2.91 |
| 40% $FAB_1$, 10% w/w P188 | 56 | 3.0 | 3.41 |

The P188 formulations were analyzed for SVP content using the methods described above. FIG. 15A shows that inclusion of 0.67% (w/w) P188 in the dry powder formulation reduces the absolute number of SVPs per ml on reconstitution. The trend was observed when the formulation was reconstituted to a concentration of 30 mg/ml $FAB_1$ (FIG. 15A) or 2.5 mg/ml $FAB_1$ (FIG. 15B).

Example 11 Characterization of Leucine/Trileucine Formulations Comprising 1.1% (w/w) PS-80

In this example the powder properties of a dry powder formulation comprising either 1% or 40% (w/w) $Fab_1$ and 1.1% (w/w/) PS-80 were analysed. The complete formulation compositions are shown in Table 25. Formulations were manufactured as described in Example 6.

TABLE 25

By weight amounts of excipients in dry powder formulations comprising 1.1% (w/w) PS-80 and either 40% (w/w) or 1% (w/w) $Fab_1$.

| | $Fab_1$ 40% (w/w) | $Fab_1$ 1% (w/w) |
|---|---|---|
| Trileucine | 2 | 2 |
| Leucine | 10.5 | 10.5 |
| Trehalose | 37.9 | 76.9 |
| Citrate buffer | 8.5 | 8.5 |

The stability of the formulations were analysed following storage for one or three months at either 40° C. and 75% relative humidity (40/75) or 25° C. and 60% relative humidity (25/60). Particle size distributions, moisture content and surface rugosity were tested. FIGS. 16A and B show that moisture content and particle size distributions remained stable over time for formulations comprising 40% (w/w) $Fab_1$. Figure C shows that the morphology of the particles remains consistent over time. FIGS. 17A and 17B show that moisture content and particle size distributions remained stable over time for formulations comprising 1% (w/w) $Fab_1$. FIG. 17C shows that the morphology of the particles remains consistent over time.

The formation of SVPs on reconstitution following storage at either 40/75 for 1 or 3 months, or 25/60 for 3 months was analysed. Analysis was carried out as described in Example 8. FIG. 18A shows that, on reconstitution of the 40% (w/w) $Fab_1$ formulation to a $Fab_1$ concentration of 30 mg.ml, the amount of SVPs forming under each condition is unchanged. FIG. 18B shows that, on reconstitution of the 1% (w/w) $Fab_1$ formulation to a $Fab_1$ concentration of 0.75 mg/ml, the amount of SVPs forming under each condition is unchanged.

Aerosol characteristics were also test following storage. The results are shown in Tables 26 and 27.

TABLE 26

Aerosol performance of formulations comprising 40% (w/w) $Fab_1$ and 1.1% (w/w) PS-80 immediately following manufacture and after storage for 1 or 3 months at 40/75 or 3 months at 25/60.

| | T = 0 | 1 m 40/75 | 3 m 40/75 | 3 m 25/60 |
|---|---|---|---|---|
| % FPF (<5 um) | 81 | 87 | 77 | 78 |
| FPM (<5 um) (mg) | 5.2 | 5.1 | 4.7 | 5.1 |
| MMAD (μm) | 2.97 | 2.77 | 3.20 | 3.16 |
| DD (%) | 85 | 87 | 82 | 84 |

TABLE 27

Aerosol performance of formulations comprising 1% (w/w) $Fab_1$ and 1.1% (w/w) PS-80 immediately following manufacture and after storage for 1 or 3 months at 40/75 or 3 months at 25/60.

| | T = 0 | 1 m 40/75 | 3 m 40/75 | 3 m 25/60 |
|---|---|---|---|---|
| % FPF (<5 um) | 79 | 79 | 73 | 73 |
| FPM (<5 um) (mg) | 0.12 | 0.11 | 0.11 | 0.1 |
| MMAD (μm) | 3.11 | 3.05 | 3.24 | 3.27 |
| DD (%) | 77 | 83 | 81 | 78 |

The percent delivered dose (DD) was also characterized following storage of each formulation under each condition. The results are shown in Tables 26 and 27.

The potency of $Fab_1$ in each of the formulations described in Table 25 was also tested following storage at 40/75 for 1 or 3 months, or 25/60 for 3 months.

Potency was determined using homogeneous time resolved fluorescence (HTRF). HTRF combines fluorescence resonance energy transfer technology (FRET) with time-resolved measurements (TR). When two fluorophores, a donor and acceptor, are in close proximity to each other, excitation of the donor prompts an energy transfer to the acceptor, thus creating a FRET signal. In this assay, Streptavidin-Europium Cryptate, bound to biotinylated human TSLP, is the donor and a d2 labelled anti-TSLP mAb is the acceptor. $FAB_1$ binds to human TSLP and prevents the binding of the labelled mAb. This in turn increases the distance between the donor and acceptor fluorophores and results in a decrease in FRET signal.

After assessing parallelism between Reference Standard and assay control or between Reference Standard and test samples, a constrained four parameter logistic (4PL) curve fit is performed, and the relative potencies of FAB' assay control and test samples are calculated by dividing the IC50 value of the Reference Standard by the IC50 value of the assay control or each test sample and multiplying by 100%.

Potency levels of $Fab_1$ were between 85 to 110% of the potency of $Fab_1$ immediately reconstituted (i.e., t=0) from the equivalent formulation.

REFERENCES

Darling R J, Brault P A. Assay and Drug Development Technologies. 2004; 2:647-657
Gauvreau G M, O'Byrne P M, Boulet L P, et al. N Engl J Med 2014; 370:2102-10
Tepper, J S, et al Int J Toxicol 2016; 35: 376-92
Rennard, S I, et al J Appl Physiol 1986; 60:532-538

It will be readily apparent to one of ordinary skill in the relevant arts that other suitable modifications and adaptations to the methods and applications described herein can be made without departing from the scope of any of the embodiments. The following examples are included herewith for purposes of illustration only and are not intended to be limiting.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A dry powder formulation comprising a plurality of microparticles, the microparticles comprising:
   a. about 8% to about 11% leucine by weight;
   b. about 2% to about 4% trileucine by weight; and
   c. an antigen binding fragment of an anti-thymic stromal lymphopoietin (TSLP) antibody comprising:
      a heavy chain variable domain comprising:
         i. a heavy chain CDR1 sequence consisting of the amino acid sequence set forth in SEQ ID NO:1;
         ii. a heavy chain CDR2 sequence consisting of the amino acid sequence set forth in SEQ ID NO:2; and
         iii. a heavy chain CDR3 sequence consisting of the amino acid sequence set forth in SEQ ID NO:3, and
      a light chain variable domain comprising:
         i. a light chain CDR1 sequence consisting of the amino acid sequence set forth in SEQ ID NO:5;
         ii. a light chain CDR2 sequence consisting of the amino acid sequence set forth in SEQ ID NO:6, and
         iii. a light chain CDR3 sequence consisting of the amino acid sequence set forth in SEQ ID NO:7.

2. The dry powder formulation of claim 1, wherein the dry powder formulation has a compressed bulk density of about 0.4-1.0 g/cm$^3$.

3. The dry powder formulation of claim 1, further comprising a glass stabilization agent.

4. The dry powder formulation of claim 3, wherein:
   a. the glass stabilization agent is an amorphous saccharide or a buffer; or
   b. the glass stabilization agent comprises an amorphous saccharide and a buffer.

5. The dry powder formulation of claim 4, wherein the amorphous saccharide is selected from the group consisting of trehalose, sucrose, raffinose, inulin, dextran, mannitol, and cyclodextrin.

6. The dry powder formulation of claim 4, wherein the buffer is selected from the group consisting of a citrate buffer, a phosphate buffer, a histidine buffer, a glycine buffer, an acetate buffer and a tartrate buffer.

7. The dry powder formulation of claim 4, wherein the amorphous saccharide is trehalose.

8. The dry powder formulation of claim 1, wherein the formulation comprises about 10.5% leucine by weight and about 2% trileucine by weight.

9. The dry powder formulation of claim 1, wherein the formulation further comprises a surfactant, and wherein the surfactant is selected from polysorbate-20 (PS-20), polysorbate-40 (PS-40), polysorbate-60 (PS-60), polysorbate-80 (PS-80) and poloxamer-188.

10. The dry powder formulation of claim 9, wherein the surfactant is PS-80, and wherein PS-80 is present at a concentration in the range of from about 0.27% by weight to about 2.7% by weight, or from about 0.67% by weight to about 1.33% by weight.

11. The dry powder formulation of claim 10, wherein the PS-80 is present at a concentration of about 1.1% by weight.

12. A dry powder formulation comprising a plurality of microparticles, the microparticles comprising:
   a. about 10.5% leucine by weight;
   b. about 2% trileucine by weight;
   c. from about 1% to about 40% by weight of an antigen binding fragment of an anti-thymic stromal lymphopoietin (TSLP) antibody comprising:
      a heavy chain variable domain comprising:
         i. a heavy chain CDR1 sequence consisting of the amino acid sequence set forth in SEQ ID NO:1;
         ii. a heavy chain CDR2 sequence consisting of the amino acid sequence set forth in SEQ ID NO:2; and
         iii. a heavy chain CDR3 sequence consisting of the amino acid sequence set forth in SEQ ID NO:3, and
      a light chain variable domain comprising:
         i. a light chain CDR1 sequence consisting of the amino acid sequence set forth in SEQ ID NO:5;
         ii. a light chain CDR2 sequence consisting of the amino acid sequence set forth in SEQ ID NO:6, and
         iii. a light chain CDR3 sequence consisting of the amino acid sequence set forth in SEQ ID NO:7;
   d. about 1.1% by weight polysorbate-80;
   e. buffer; and
   f. trehalose in an amount by weight to make up to 100%.

13. The dry powder formulation of claim 1, wherein the
   a. the heavy chain variable domain comprises SEQ ID NO:4; and
   b. the light chain variable domain comprises SEQ ID NO:8.

14. The dry powder formulation of claim 12, wherein:
   a. the heavy chain variable domain comprises SEQ ID NO:4; and
   b. the light chain variable domain comprises SEQ ID NO:8.

15. The dry powder formulation of claim 14, wherein the heavy chain has the sequence set forth in SEQ ID NO:28 and the light chain has the sequence set forth in SEQ ID NO:29.

16. The dry powder formulation of claim 1, wherein the antigen binding fragment is selected from Fab, Fab', F(ab')2, scFv, minibody, or diabody.

17. The dry powder formulation of claim 16, wherein the antigen binding fragment is a Fab.

18. The dry powder formulation of claim 17, wherein the Fab is human or humanized.

19. The dry powder formulation of claim 1, wherein the anti-TSLP antibody from which the antigen binding fragment is derived is an IgG1.

* * * * *

SEQUENCE LISTING

```
<160> NUMBER OF SEQ ID NOS: 31

<210> SEQ ID NO 1
<211> LENGTH: 5
<212> TYPE: PRT
<213> ORGANISM: Homo sapiens
<220> FEATURE:
<221> NAME/KEY: MISC_FEATURE
<223> OTHER INFORMATION: HCDR1 FAB1

<400> SEQUENCE: 1

Thr Tyr Gly Met His
1               5

<210> SEQ ID NO 2
<211> LENGTH: 17
<212> TYPE: PRT
<213> ORGANISM: Homo sapiens
<220> FEATURE:
<221> NAME/KEY: MISC_FEATURE
<223> OTHER INFORMATION: HCDR2 FAB1

<400> SEQUENCE: 2

Val Ile Trp Tyr Asp Gly Ser Asn Lys His Tyr Ala Asp Ser Val Lys
1               5                   10                  15

Gly

<210> SEQ ID NO 3
<211> LENGTH: 13
<212> TYPE: PRT
<213> ORGANISM: Homo sapiens
<220> FEATURE:
<221> NAME/KEY: MISC_FEATURE
<223> OTHER INFORMATION: HCDR3 FAB1

<400> SEQUENCE: 3

Ala Pro Gln Trp Glu Leu Val His Glu Ala Phe Asp Ile
1               5                   10
```

<210> SEQ ID NO 4
<211> LENGTH: 122
<212> TYPE: PRT
<213> ORGANISM: Homo sapiens
<220> FEATURE:
<221> NAME/KEY: MISC_FEATURE
<223> OTHER INFORMATION: HEAVY CHAIN VH FAB1

<400> SEQUENCE: 4

Gln Met Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Thr Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys His Tyr Ala Asp Ser Val
        50                  55                  60

Lys Gly Arg Phe Thr Ile Thr Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Ala Pro Gln Trp Glu Leu Val His Glu Ala Phe Asp Ile Trp
            100                 105                 110

Gly Gln Gly Thr Met Val Thr Val Ser Ser
        115                 120

<210> SEQ ID NO 5
<211> LENGTH: 11
<212> TYPE: PRT
<213> ORGANISM: Homo sapiens
<220> FEATURE:
<221> NAME/KEY: MISC_FEATURE
<223> OTHER INFORMATION: LCDR1 FAB1

<400> SEQUENCE: 5

Gly Gly Asn Asn Leu Gly Ser Lys Ser Val His
1               5                   10

<210> SEQ ID NO 6
<211> LENGTH: 7
<212> TYPE: PRT
<213> ORGANISM: Homo sapiens
<220> FEATURE:
<221> NAME/KEY: MISC_FEATURE
<223> OTHER INFORMATION: LCDR2 FAB1

<400> SEQUENCE: 6

Asp Asp Ser Asp Arg Pro Ser
1               5

<210> SEQ ID NO 7
<211> LENGTH: 11
<212> TYPE: PRT
<213> ORGANISM: Homo sapiens
<220> FEATURE:
<221> NAME/KEY: MISC_FEATURE
<223> OTHER INFORMATION: LCDR3 FAB1

<400> SEQUENCE: 7

Gln Val Trp Asp Ser Ser Ser Asp His Val Val
1               5                   10

<210> SEQ ID NO 8

```
<211> LENGTH: 108
<212> TYPE: PRT
<213> ORGANISM: Homo sapiens
<220> FEATURE:
<221> NAME/KEY: MISC_FEATURE
<223> OTHER INFORMATION: LIGHT CHAIN VL
<220> FEATURE:
<221> NAME/KEY: MISC_FEATURE
<223> OTHER INFORMATION: LIGHT CHAIN VL FAB1

<400> SEQUENCE: 8

Ser Tyr Val Leu Thr Gln Pro Pro Ser Val Ser Val Ala Pro Gly Gln
1               5                   10                  15

Thr Ala Arg Ile Thr Cys Gly Gly Asn Asn Leu Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Trp Ile Pro Glu Arg Phe Ser Gly Ser
    50                  55                  60

Asn Ser Gly Asn Thr Ala Thr Leu Thr Ile Ser Arg Gly Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 9
<211> LENGTH: 366
<212> TYPE: DNA
<213> ORGANISM: Homo sapiens
<220> FEATURE:
<221> NAME/KEY: misc_feature
<223> OTHER INFORMATION: VARIABLE HEAVY CHAIN FAB1

<400> SEQUENCE: 9
cagatgcagt tggttgaatc tggtggcggc gtggtgcagc ctggcagatc tctgagactg      60
tcttgtgccg cctccggctt caccttcaga acctacggaa tgcactgggt ccgacaggcc     120
cctggcaaag gattggaatg ggtcgccgtg atttggtacg acggctccaa caagcactac     180
gccgactccg tgaagggcag attcaccatc accagagaca actccaagaa caccctgaac     240
ctgcagatga actccctgag agccgaggac accgccgtgt actattgtgc tagagccccct     300 cagtgggaac tcgtgcatga ggcctttgac atctggggcc agggaacaat ggtcaccgtc     360
tcctca                                                                 366

<210> SEQ ID NO 10
<211> LENGTH: 324
<212> TYPE: DNA
<213> ORGANISM: Homo sapiens
<220> FEATURE:
<221> NAME/KEY: misc_feature
<223> OTHER INFORMATION: FAB1 VARIABLE LIGHT CHAIN

<400> SEQUENCE: 10
tcatatgttc ttacacaacc accgtcggtt tcggttgctc caggacaaac agctcgaatt      60
acatgcggag gaaacaacct cggatcgaag tcggttcact ggtatcaaca aaagccagga     120
caagctccag ttctcgtggt gtacgatgat tcagatcgac catcatggat cccagagcga     180
ttctcaggat caaactcggg aaatactgcc acgctcacaa tttcacgcgg agaagcggga     240
gatgaagctg attactattg ccaagtgtgg gactcgtcgt cagatcatgt tgttttcgga     300
```
ggtggaacaa agctcacagt gctc                                    324

<210> SEQ ID NO 11
<211> LENGTH: 11
<212> TYPE: PRT
<213> ORGANISM: Homo sapiens
<220> FEATURE:
<221> NAME/KEY: MISC_FEATURE
<223> OTHER INFORMATION: LCDR1 FAB2

<400> SEQUENCE: 11

Gly Gly Asn Asn Ile Gly Ser Lys Ser Val His
1               5                   10

<210> SEQ ID NO 12
<211> LENGTH: 108
<212> TYPE: PRT
<213> ORGANISM: Homo sapiens
<220> FEATURE:
<221> NAME/KEY: MISC_FEATURE
<223> OTHER INFORMATION: LIGHT CHAIN FAB2
<220> FEATURE:
<221> NAME/KEY: MISC_FEATURE
<223> OTHER INFORMATION: LIGHT CHAIN VL FAB2

<400> SEQUENCE: 12

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Trp Ile Pro Glu Arg Phe Ser Gly Ser
    50                  55                  60

Asn Ser Gly Asn Thr Ala Thr Leu Thr Ile Ser Arg Gly Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 13
<211> LENGTH: 11
<212> TYPE: PRT
<213> ORGANISM: Homo sapiens
<220> FEATURE:
<221> NAME/KEY: MISC_FEATURE
<223> OTHER INFORMATION: LCDR1 FAB3

<400> SEQUENCE: 13

Gly Gly Asn Asn Val Gly Ser Lys Ser Val His
1               5                   10

<210> SEQ ID NO 14
<211> LENGTH: 108
<212> TYPE: PRT
<213> ORGANISM: Homo sapiens
<220> FEATURE:
<221> NAME/KEY: MISC_FEATURE
<223> OTHER INFORMATION: LIGHT CHAIN FAB3
<220> FEATURE:
<221> NAME/KEY: MISC_FEATURE
<223> OTHER INFORMATION: LIGHT CHAIN VL FAB3

<400> SEQUENCE: 14

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Val Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Trp Ile Pro Glu Arg Phe Ser Gly Ser
    50                  55                  60

Asn Ser Gly Asn Thr Ala Thr Leu Thr Ile Ser Arg Gly Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105
```

<210> SEQ ID NO 15
<211> LENGTH: 17
<212> TYPE: PRT
<213> ORGANISM: Homo sapiens
<220> FEATURE:
<221> NAME/KEY: MISC_FEATURE
<223> OTHER INFORMATION: HCDR2 FAB4

<400> SEQUENCE: 15

```
Val Ile Trp Tyr Asp Gly Ser Asn Lys His Tyr Ala Glu Ser Val Lys
1               5                   10                  15

Gly
```

<210> SEQ ID NO 16
<211> LENGTH: 122
<212> TYPE: PRT
<213> ORGANISM: Homo sapiens
<220> FEATURE:
<221> NAME/KEY: MISC_FEATURE
<223> OTHER INFORMATION: HEAVY CHAIN FAB4
<220> FEATURE:
<221> NAME/KEY: MISC_FEATURE
<223> OTHER INFORMATION: HEAVY CHAIN VH FAB4

<400> SEQUENCE: 16

```
Gln Met Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Glu Ser Val
    50                  55                  60

Lys Gly Arg Phe Thr Ile Thr Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Ala Pro Gln Trp Glu Leu Val His Glu Ala Phe Asp Ile Trp
            100                 105                 110

Gly Gln Gly Thr Met Val Thr Val Ser Ser
        115                 120
```

<210> SEQ ID NO 17
<211> LENGTH: 17
<212> TYPE: PRT

```
<213> ORGANISM: Homo sapiens
<220> FEATURE:
<221> NAME/KEY: MISC_FEATURE
<223> OTHER INFORMATION: HCDR2 FAB5

<400> SEQUENCE: 17

Val Ile Trp Tyr Asp Gly Ser Asn Lys His Tyr Ala Asp Ser Val Lys
1               5                   10                  15

Ala

<210> SEQ ID NO 18
<211> LENGTH: 122
<212> TYPE: PRT
<213> ORGANISM: Homo sapiens
<220> FEATURE:
<221> NAME/KEY: MISC_FEATURE
<223> OTHER INFORMATION: HEAVY CHAIN FAB5
<220> FEATURE:
<221> NAME/KEY: MISC_FEATURE
<223> OTHER INFORMATION: HEAVY CHAIN VH FAB5

<400> SEQUENCE: 18

Gln Met Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Ala Arg Phe Thr Ile Thr Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Ala Pro Gln Trp Glu Leu Val His Glu Ala Phe Asp Ile Trp
            100                 105                 110

Gly Gln Gly Thr Met Val Thr Val Ser Ser
        115                 120

<210> SEQ ID NO 19
<211> LENGTH: 11
<212> TYPE: PRT
<213> ORGANISM: Homo sapiens
<220> FEATURE:
<221> NAME/KEY: MISC_FEATURE
<223> OTHER INFORMATION: LCDR1 FAB6

<400> SEQUENCE: 19

Gly Gly Gln Asn Leu Gly Ser Lys Ser Val His
1               5                   10

<210> SEQ ID NO 20
<211> LENGTH: 108
<212> TYPE: PRT
<213> ORGANISM: Homo sapiens
<220> FEATURE:
<221> NAME/KEY: MISC_FEATURE
<223> OTHER INFORMATION: LIGHT CHAIN FAB6
<220> FEATURE:
<221> NAME/KEY: MISC_FEATURE
<223> OTHER INFORMATION: LIGHT CHAIN VL FAB6

<400> SEQUENCE: 20

Ser Tyr Val Leu Thr Gln Pro Pro Ser Val Ser Val Ala Pro Gly Gln
```

```
                1               5                  10                  15
              Thr Ala Arg Ile Thr Cys Gly Gly Gln Asn Leu Gly Ser Lys Ser Val
                               20                  25                  30

His Trp Tyr Gln Gln Lys Pro Gly Gln Ala Pro Val Leu Val Val Tyr
                               35                  40                  45

Asp Asp Ser Asp Arg Pro Ser Trp Ile Pro Glu Arg Phe Ser Gly Ser
                       50                  55                  60

Asn Ser Gly Asn Thr Ala Thr Leu Thr Ile Ser Arg Gly Glu Ala Gly
               65                  70                  75                  80

Asp Glu Ala Asp Tyr Tyr Cys Gln Val Trp Asp Ser Ser Asp His
                                   85                  90                  95

Val Val Phe Gly Gly Gly Thr Lys Leu Thr Val Leu
                              100                 105

<210> SEQ ID NO 21
<211> LENGTH: 11
<212> TYPE: PRT
<213> ORGANISM: Homo sapiens
<220> FEATURE:
<221> NAME/KEY: MISC_FEATURE
<223> OTHER INFORMATION: LCDR1 FAB7

<400> SEQUENCE: 21

Gly Gly Asn Gln Leu Gly Ser Lys Ser Val His
1               5                   10

<210> SEQ ID NO 22
<211> LENGTH: 108
<212> TYPE: PRT
<213> ORGANISM: Homo sapiens
<220> FEATURE:
<221> NAME/KEY: MISC_FEATURE
<223> OTHER INFORMATION: LIGHT CHAIN FAB7
<220> FEATURE:
<221> NAME/KEY: MISC_FEATURE
<223> OTHER INFORMATION: LIGHT CHAIN VL FAB7

<400> SEQUENCE: 22

Ser Tyr Val Leu Thr Gln Pro Pro Ser Val Ser Val Ala Pro Gly Gln
              1               5                   10                  15

Thr Ala Arg Ile Thr Cys Gly Gly Asn Gln Leu Gly Ser Lys Ser Val
                               20                  25                  30

His Trp Tyr Gln Gln Lys Pro Gly Gln Ala Pro Val Leu Val Val Tyr
                               35                  40                  45

Asp Asp Ser Asp Arg Pro Ser Trp Ile Pro Glu Arg Phe Ser Gly Ser
                       50                  55                  60

Asn Ser Gly Asn Thr Ala Thr Leu Thr Ile Ser Arg Gly Glu Ala Gly
               65                  70                  75                  80

Asp Glu Ala Asp Tyr Tyr Cys Gln Val Trp Asp Ser Ser Asp His
                                   85                  90                  95

Val Val Phe Gly Gly Gly Thr Lys Leu Thr Val Leu
                              100                 105

<210> SEQ ID NO 23
<211> LENGTH: 11
<212> TYPE: PRT
<213> ORGANISM: Homo sapiens
<220> FEATURE:
<221> NAME/KEY: MISC_FEATURE
<223> OTHER INFORMATION: LCDR3 FAB8

<400> SEQUENCE: 23
```

```
Gln Val Trp Asp Thr Ser Ser Asp His Val Val
1               5                   10
```

<210> SEQ ID NO 24
<211> LENGTH: 108
<212> TYPE: PRT
<213> ORGANISM: Homo sapiens
<220> FEATURE:
<221> NAME/KEY: MISC_FEATURE
<223> OTHER INFORMATION: LIGHT CHAIN FAB8
<220> FEATURE:
<221> NAME/KEY: MISC_FEATURE
<223> OTHER INFORMATION: LIGHT CHAIN VL FAB8

<400> SEQUENCE: 24

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Leu Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Trp Ile Pro Glu Arg Phe Ser Gly Ser
    50                  55                  60

Asn Ser Gly Asn Thr Ala Thr Leu Thr Ile Ser Arg Gly Glu Ala Gly
65                  70                  75                  80

Asp Glu Ala Asp Tyr Tyr Cys Gln Val Trp Asp Thr Ser Ser Asp His
                85                  90                  95

Val Val Phe Gly Gly Gly Thr Lys Leu Thr Val Leu
            100                 105
```

<210> SEQ ID NO 25
<211> LENGTH: 11
<212> TYPE: PRT
<213> ORGANISM: Homo sapiens
<220> FEATURE:
<221> NAME/KEY: MISC_FEATURE
<223> OTHER INFORMATION: LCDR3 FAB9

<400> SEQUENCE: 25

```
Gln Val Trp Asp Ser Thr Ser Asp His Val Val
1               5                   10
```

<210> SEQ ID NO 26
<211> LENGTH: 108
<212> TYPE: PRT
<213> ORGANISM: Homo sapiens
<220> FEATURE:
<221> NAME/KEY: MISC_FEATURE
<223> OTHER INFORMATION: LIGHT CHAIN FAB9
<220> FEATURE:
<221> NAME/KEY: MISC_FEATURE
<223> OTHER INFORMATION: LIGHT CHAIN VL FAB9

<400> SEQUENCE: 26

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Leu Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Trp Ile Pro Glu Arg Phe Ser Gly Ser
    50                  55                  60
```

Asn Ser Gly Asn Thr Ala Thr Leu Thr Ile Ser Arg Gly Glu Ala Gly
65                  70                  75                  80

Asp Glu Ala Asp Tyr Tyr Cys Gln Val Trp Asp Ser Thr Ser Asp His
                85                  90                  95

Val Val Phe Gly Gly Gly Thr Lys Leu Thr Val Leu
            100                 105

<210> SEQ ID NO 27
<211> LENGTH: 159
<212> TYPE: PRT
<213> ORGANISM: homo sapiens

<400> SEQUENCE: 27

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
                20                  25                  30

Asn Cys Asp Phe Glu Lys Ile Lys Ala Ala Tyr Leu Ser Thr Ile Ser
            35                  40                  45

Lys Asp Leu Ile Thr Tyr Met Ser Gly Thr Lys Ser Thr Glu Phe Asn
50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
130                 135                 140

Gln Gly Leu Trp Arg Arg Phe Asn Arg Pro Leu Leu Lys Gln Gln
145                 150                 155

<210> SEQ ID NO 28
<211> LENGTH: 227
<212> TYPE: PRT
<213> ORGANISM: Homo Sapiens

<400> SEQUENCE: 28

Gln Met Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Thr Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys His Tyr Ala Asp Ser Val
50                  55                  60

Lys Gly Arg Phe Thr Ile Thr Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Ala Pro Gln Trp Glu Leu Val His Glu Ala Phe Asp Ile Trp
            100                 105                 110

Gly Gln Gly Thr Met Val Thr Val Ser Ser Ala Ser Thr Lys Gly Pro
        115                 120                 125

```
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys
225

<210> SEQ ID NO 29
<211> LENGTH: 214
<212> TYPE: PRT
<213> ORGANISM: Homo Sapiens

<400> SEQUENCE: 29

Ser Tyr Val Leu Thr Gln Pro Pro Ser Val Ser Val Ala Pro Gly Gln
1               5                   10                  15

Thr Ala Arg Ile Thr Cys Gly Gly Asn Asn Leu Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Trp Ile Pro Glu Arg Phe Ser Gly Ser
50                  55                  60

Asn Ser Gly Asn Thr Ala Thr Leu Thr Ile Ser Arg Gly Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
210

<210> SEQ ID NO 30
<211> LENGTH: 681
<212> TYPE: DNA
<213> ORGANISM: Homo sapiens

<400> SEQUENCE: 30
```

-continued

```
cagatgcagt tggttgaatc tggtggcggc gtggtgcagc ctggcagatc tctgagactg    60
tcttgtgccg cctccggctt caccttcaga acctacggaa tgcactgggt ccgacaggcc   120
cctggcaaag gattggaatg ggtcgccgtg atttggtacg acggctccaa caagcactac   180
gccgactccg tgaagggcag attcaccatc accagagaca actccaagaa caccctgaac   240
ctgcagatga actccctgag agccgaggac accgccgtgt actattgtgc tagagcccct   300
cagtgggaac tcgtgcatga ggcctttgac atctggggcc agggaacaat ggtcaccgtc   360
tcctcagcct ccaccaaggg cccatcggtc ttccccctgg caccctcctc caagagcacc   420
tctgggggca gcggccct gggctgcctg gtcaaggact acttccccga accggtgacg   480
gtgtcgtgga actcaggcgc cctgaccagc ggcgtgcaca ccttccggc tgtcctacag   540 tcctcaggac tctactccct cagcagcgtg gtgacagtgc cctccagcag cttgggcacc   600
cagacctaca tctgcaacgt gaatcacaag cccagcaaca ccaaggtgga caagagagtt   660
gagcccaaat cttgtgacaa a                                             681
```

<210> SEQ ID NO 31
<211> LENGTH: 642
<212> TYPE: DNA
<213> ORGANISM: Homo sapiens

<400> SEQUENCE: 31

```
tcatatgttc ttacacaacc accgtcggtt tcggttgctc caggacaaac agctcgaatt    60
acatgcggag gaaacaacct cggatcgaag tcggttcact ggtatcaaca aaagccagga   120
caagctccag ttctcgtggt gtacgatgat tcagatcgac catcatggat cccagagcga   180
ttctcaggat caaactcggg aaatactgcc acgctcacaa tttcacgcgg agaagcggga   240
gatgaagctg attactattg ccaagtgtgg gactcgtcgt cagatcatgt tgttttcgga   300
ggtggaacaa agctcacagt gctcggtcag cccaaggctg ccccctcggt cactctgttc   360
ccgccctcct ctgaggagct tcaagccaac aaggccacac tggtgtgtct cataagtgac   420
ttctacccgg gagccgtgac agtggcctgg aaggcagata gcagcccgt caaggcggga   480 gtggagacca ccacaccctc caaacaaagc aacaacaagt acgcggccag cagctatctg   540
agcctgacgc ctgagcagtg gaagtcccac agaagctaca gctgccaggt cacgcatgaa   600
gggagcaccg tggagaagac agtggcccct acagaatgtt ca                     642
```